United States Patent
Marchionni et al.

(10) Patent No.: US 6,232,061 B1
(45) Date of Patent: May 15, 2001

(54) HOMOLOGY CLONING

(75) Inventors: Mark Andrew Marchionni, Arlington; Carl D. Johnson, Cambridge, both of MA (US)

(73) Assignee: Cambridge Neuroscience, Inc., Norwood, MA (US)

(*) Notice: Subject to any disclaimer, the term of this patent is extended or adjusted under 35 U.S.C. 154(b) by 0 days.

(21) Appl. No.: 07/861,458

(22) Filed: Apr. 1, 1992

(51) Int. Cl.[7] .............................. C12Q 1/68; C12P 19/34
(52) U.S. Cl. ................................ 435/6; 435/91.2; 436/94
(58) Field of Search ....................... 435/6, 91.2; 436/94; 935/78

(56) References Cited

U.S. PATENT DOCUMENTS

| | | | |
|---|---|---|---|
| 4,851,330 | 7/1989 | Kohne et al. | 435/6 |
| 4,965,188 | 10/1990 | Mullis et al. | 435/91.2 |
| 5,087,558 | * 2/1992 | Webster | 435/5 |

FOREIGN PATENT DOCUMENTS

PCT/US93/03102  6/1993  (WO).

OTHER PUBLICATIONS

Thomas, W. K. et al. 1990. "Mode and Tempo of Molecular Evolution in the Nematode Caenorhabditis: Cytochrome Oxidase II and Calmodulin Sequences," *Genetics* 128:269.

Felsenstein, J. 1985. "Confidence Limits on Phylogenies: An Approach Using the Bootstrap," *Evolution* 39(4):783.

Dibb, N. J. et al. 1989. "Sequence Analysis of the Complete *Caenorhabditis elegans* Myosin Heavy Chain Gene Family," *J. Mol. Biol.* 205:603.

van der Voorn, L. et al. 1990. "Characterization of a G–Protein β–Subunit Gene from the Nematode *Caenorhabditis elegans*," *J. Mol. Biol.* 213:17.

Huang, X. –Y. et al. 1989. "Genomic Organization of the Glyceraldhyde–3–Phosphate Dehyrdogenase Gene Family of *Caenorhabditis elegans*," *J. Mol. Biol.* 206:411.

Cox, G. N., et al. "*Haemonchus contortus*: Evidence that the 3A3 Collagen Gene is a Member of an Evolutionarily Conserved Family Nematode Cuticle Collagens," *Experimental Parasitology* 70:175.

Bürglin, T. R. et al. 1989. "*Caenorhabditis elegans* has scores of Homoebox–Containing Genes," *Nature* 341:239.

Finney, M. et al.1988. "The *C. elegans* Cell Lineage and Differentiation Gene *unc–86* Encodes a Protein with with a Homeodomain and Extended Similarity to Transcription Factors," *Cell* 55:757.

Herr, W., et al. 1988. "The POU Domain: A Large Conserved Region in the Mammalian *pit–1*, *oct–1*, *oct–2*, and *Caenorhabditis elegans unc–86*," Gene Products. *Gene & Development* 2:1513.

Candido, E. P. M. et al. 1989. "Structure, Organization and Expression of the 16–kDa Heat Shock Gene Family of *Caenorhabditis elegans*," *Genome* 31:690.

Schaller, D. et al. 1990. "Cloning and Analysis of Three New Homebox Genes from the Nematode *Caenorhabditis elegans*," *Nucleic Acids. Res.* 18(8):2033.

Johnson, J. E. et al. 1990. "Two Rat Homologues of *Drosophila achaete–scute* Specifically Expressed in Neurol Precursors," *Nature* 346:858.

Mathews, L. S. et al. 1991. "Expressed Cloning of an Activin Receptor, a Predicted Transmembrane Serine Kinase," *Cell* 65:973.

Georgi, L. L. et al. 1990. "*daf*–1, a *C. elegans* Gene Controlling Dauer Larva Development, Encodes a Novel Receptor Protein Kinase," *Cell* 61:635.

Goddard, J. M. et al. 1986. "Isolation and Characterization of *Caenorhabditis elegans* DNA Sequences Homolgous to the *v–abl* Oncogene," *PNAS* 83:2172.

Heschl, M. F. P. et al. 1990. "Functional Elements and Domains Inferred from Sequence Comparisons of a Heat Shock Gene in Two Nematodes," *J. Mol. Evol.* 31:3.

Kingston, I. B., et al. 1989. "Comparison of Collagen Gene Sequences in *Ascaris suum* and *Caenorhabditis elegans*," *Mol. and Biochem. Parasitology* 37:137.

McGinnis, W. et al. 1984. "A Conserved DNA sequence in Homoeotic Genes of the *Drosophila* Antennapedia and Bithorax Complexes," *Nature* 308:428.

Shepard, J. C. W. et al. 1984. "Fly and Frog Homoeo Domains Show Homologies with Yeast Mating Type Regulatory Proteins," *Nature* 310:70.

Fields, C. 1988. "Domain Organization and Intron Positions in *Caenorhabditis elegans* Collagen Genes: The 54–bp Module Hypothesis Revisited," *J. Mol. Evol.* 28:55.

Chalfie, M. et al. 1990. "The Identification and Suppression of Inherited Neurodegeneration in *Caenorhabditis elegans*," *Nature* 345:410.

Liebert, F. et al. 1989. "Selective Amplification and Cloning of Four New Members of the G Protein–Coupled Receptor Family," *Science* 244:569.

Buck, L. et al. 1991. "A Novel Multigene Family May Encode Odorant Receptors: A Molecular Basis for Odor Recognition," *Cell* 65:175.

Maisonpierre, P.C. et al. 1990. "Neurotrophin–3: A Neurotropic Factor Related to NGF and BDNF," *Science* 247:1446.

(List continued on next page.)

Primary Examiner—Kenneth R. Horlick
(74) Attorney, Agent, or Firm—Peter F. Corless; Edwards & Angell, LLP

(57) ABSTRACT

A long-distance homology cloning method which involves a multi-oligonucleotide, multi-step and iterative strategy designed to identify DNA sequences that code for evolutionary conserved amino acid sequences.

39 Claims, 50 Drawing Sheets

OTHER PUBLICATIONS

Touchot, N. et al. 1987. "Four Additional Members of the *ras* Gene Superfamily Isolated by an Oligonucleotide Strategy: Molecular Cloning of YPT–Related cDNAs from a Rat Brain Library," *PNAS USA* 84:8210.

Jones, K.R. et al. 1990. "Molecular Cloning of a Human Gene that is a Member of the Nerve Growth Factor Family," *PNAS USA* 87:8060.

Van Tol, H.H.M. et al. 1991. "Cloning of the Gene for a Human Dopamine $D_4$ Receptor with High Affinity for the Antipsychotic Clozapine," *Nature* 350:610.

Sunahara, R.K. et al. 1991. "Cloning of the Gene for a Human Dopamine $H_5$ Receptor with Higher Affinity for Dopamine than $D_1$." *Nature* 350:614.

Okimoto, R. et al. 1992. "The Mitochondrial Genomes of Two Nematodes, *Caenorhabditis elegans* and *Ascaris suum*," *Genetics* 130:471.

Heschl, M.F.P. et al. 1989. "Characterization of the hsp70 Multigene Family of *Caenorhabditis elegans*," *DNA* 8(4):233.

Sharp, Jama, vol. 260, No. 20, Issued Nov./25/88, pp. 3035–3041.

Litman et al., Nucleic Acids Research, vol. 10, No. 11, Issued 1982, pp. 3371–3380.

Gum et al., J. Biol. Chem., vol. 266, No. 33 Issued Nov./25/91, pp. 22733–22738.

Kindt et al., Eur. J. Immunol., vol. 15, Issued 1985, pp. 535–540.

Ellis et al., Cell, vol. 44, Issued Mar./28/86, pp. 817–829.

Wilson et al., J. Clin. Microbiol., vol. 26, No. 12, Issued Dec./88, pp. 2484–2488.

* cited by examiner

| FIG. 4A |
|---------|
| FIG. 4B |
| FIG. 4C |

FIG. 4 ced-4 cDKA of Caenorhabditis elegans

```
GAATTCCGAAATCGAATGCGGCGCTTTGAGCGACACGAGGCTCATCCACGACTTTGAACCACGTGACGCTTATTTAGAAGGCAAAA  100
   I  P  E  I  E  C  R  A  L  S  T  R  H  T  R  L  I  H  D  F  E  P  R  D  A  L  T  Y  L  E  G  K  N

CATTTCACAGAGATCATTCTGAACTTATCAGTAAATGTCAACTCGCCTCGAGAGGATCGGCCATTTTCTTCGAATCTATCGACGTTCAAGCTTCTGAA  200
   I  F  T  E  D  H  S  E  L  I  S  K  M  S  T  R  L  E  R  I  A  N  F  L  R  I  Y  R  R  Q  A  S  E

CTTGGACCACTCATCGACTTTTCAACTACACAATCAAGTCACCTTGCTGATTTCCTCGAAGACTACATCGATTTTGCGATAAATGAGCCAGATCTAC  300
   L  G  P  L  I  D  F  F  N  Y  N  N  Q  S  H  L  A  D  F  L  E  D  Y  I  D  F  A  I  N  E  P  D  L  L

TTCGTCCAGTAGTGATTGATTCCCGACAATATGCTCGATAGGAACTATTGCTTGGGAATGTTCCAAAACAATGACATGTTCTATATTCGAGA  400
   R  P  V  V  I  A  P  Q  F  S  R  Q  H  L  D  R  K  L  L  G  N  V  P  K  Q  M  T  C  Y  I  R  E

GTATCACGTGGATCGAGTGATCAAAAGCTCGACGAGATGTGTTAGACTCCTTTTCTGTTTCTACACGGCCGAGCTGGATCCGGAAATCAGTA  500
   Y  H  V  D  R  V  I  K  K  L  D  E  M  C  D  L  D  S  F  F  L  H  G  R  A  G  S  G  K  S  V
```

FIG. 4A
PRIOR ART

```
ATTGGATCAAGCTCTTTGAAATCTGACCAACTTATTGGAATAAATTATGATTCAATCGTTTGGCTCGTTCAAAGATAGTGGAACAGCTCCAAAATCTACAT 600
 I  A  S  Q  A  L  S  K  S  D  Q  L  I  G  I  N  Y  D  S  I  V  W  L  K  D  S  G  T  A  P  K  S  T  F

TCGATTTATTACGGATATATTTGCTGATGCTAAAAAGGCGAAGACGATCTTCTCAATTCCCATCGGTGGAGCATGTCACGTCAGTGTACTCAAAGGAT 700
 D  L  F  T  D  I  L  L  M  L  K  S  E  D  D  L  N  F  P  S  V  E  H  V  T  S  V  V  L  K  R  M

GATCTGCAACGACTCATTGATCGTCCAAATACTTTATTCGTATTTGATGACGTAGTTCAAGAGAACAATTCGTTGGGCTCAGGAGCTACGTCTTCGA 800
 I  C  N  A  L  I  D  R  P  N  T  L  F  V  F  D  D  V  V  Q  E  E  T  I  R  W  A  Q  E  L  R  L  R

TGTCTTGTAACTACTCGTGACGTGGAAATATCAATGCTGCTTCTCAAACATGGACATCATTGAGTGACATCATTGAAATCGATGATGTTATGATT 900
 C  L  V  T  T  R  D  V  E  I  S  N  A  A  S  Q  T  C  E  F  I  E  V  T  S  L  E  I  D  E  C  Y  D  F

TTCTAGAAGCTTATGGAAATGCCATGCCTGTTGGAGAAAAGAAGAAGATGTTCTTAATAAACAATGAACTAAGCAGTGGAAATCCAGCAACGCTTAT 1000
 L  E  A  Y  G  N  P  M  P  V  G  E  K  E  E  D  V  L  N  K  T  I  E  L  S  S  G  N  P  A  T  L  M

GATGTTTTCAAGTCTTGTGAACCGAAACATTTGAAAAATGGCACAGCTTAATACAAATTGGAAGTCGAAGATTAGTCGGAAGTCGGTTGTTGATGTATCACC 1100
 M  F  F  K  S  C  E  P  K  T  F  E  K  M  A  Q  L  N  N  K  L  E  S  R  G  L  V  G  V  E  C  I  T

CCTTACTCGTACAAGTCACTCGCAAGTCATGGCTTCTTCAAGATGTGTTGAAGTTTGCTCAAGATGAGGATCGAAGTGCTCTTGCAGTTGTGATGCCTC 1200
 P  Y  S  Y  K  S  L  A  M  A  L  Q  R  C  V  E  V  L  S  D  E  D  R  S  A  L  A  F  A  V  V  M  P  P

CTGGGAGTTGATATACCCGTCACTGTCAAGCTATGGTCATGTGTTATTCCAGTTGATATTTGTTCAAATGAAGAAGAACAATTGGGGGATCGGTT 1300
 G  V  D  I  P  V  K  L  W  S  C  V  I  P  V  D  I  C  S  N  E  E  E  Q  L  D  D  E  V  A  D  R  L

GAAAGACTCAGCAACGTGGAGCTCTTCAGTGGAAAACGAATGCCGTTTGACATTCAAATTGATCATATTATTCATATGTTCTTGAAACACGTC 1400
 K  R  L  S  K  R  G  A  L  L  S  G  K  R  M  P  V  L  T  F  K  I  D  H  I  I  H  M  F  L  K  H  V
```

FIG.4B
PRIOR ART

```
GTTGATGACAACTATCGCCAATGGAATCTCAATTCTCGAGCAGCGTCTCTTGAATAGGAAACATAATGTATCAGTACGGAGCCACATATACCAT  1500
 V  D  D  N  Y  R  Q  W  N  L  N  S  R  A  A  S  L  E  *                                       
     V  D  D  N  Y  R  Q  W  N  L  N  S  R  A  A  V  S  L  N  R  K  H  N  V  S  V  P  E  P  H  I  P  S
```
(approximate — see figure)

FIG. 4C
PRIOR ART

Partial deg-1 cDNA clone of Caenorhabditis elegans

FIG. 6B
PRIOR ART (SEQ ID No: 4)

| FIG. 8A |
|---|
| FIG. 8B |
| FIG. 8C |
| FIG. 8D |
| FIG. 8E |

FIG. 8 ced-4 gene of Caenorhabditis briggsae

```
GAACATTCAAGCATGGAGAGAGGATGTAATTGTTTGGTGCAAACATTCATGCGAAACTCGATATTGTCATTGAAAAGGTTCATAGGTTTGA     100

AAGGGATCAATGTATGTTTTTAGTAAGAATTTATCGGACTCAATTAAAAATTACAGGGATGGGATTCACGCCAATTAACAGCAACTACCGAGGATTT     200

GGAAGAAGGACGTGTGATCATTACCAACTAAGGGAAAGATAAACTGTATAAATATAATAATGCTCACTTCTCACCTATTATTGTGCCCATTTGCCAA     300
```

FIG. 8A

```
TATTTCTAATTTCAAATCTACCTCCCTGTACAATGGATCACCAATGAAATAGATTTATCTTTCTCAAAATTGTATTTGAATATTCGTGTGTCGAAT       400

GCACTATGATCGTATTTATTGAGCTAGTTTTTTTTTCATGTCAATGGTTCATTTATAGATGCTTTGTGAAATCGAATGTCGAGCTTTGAATGCAGCACAC   500
                                                 M  L  C  E  I  E  C  R  A  L  N  A  A  H

ACAATGCTCATCCAGGACTTCGAACCACGAGATGCGCTAACCTATTTGGAAGGCGAAAAATTTCACAGAGACCATTCTGATCTCATCAGTAATATGC      600
 T  M  L  I  Q  D  F  E  P  R  D  A  L  T  Y  L  E  G  E  K  I  F  T  E  D  H  S  D  L  I  S  N  M  P

CAACTCGTCTGAAAGAATTGCGAATTTCCTTCGAGCTTATGCGACGGCAAGCGTCGGAATTGGCTCCGCTCATTGACTTTTTCGAATACAATAATCAAA    700
 T  R  L  E  R  I  A  N  F  L  R  A  Y  R  R  Q  A  S  E  L  A  P  L  I  D  F  F  E  Y  N  N  Q  N

TCATCTGAAGGACTTTCTTGATGAGTATCTCTGGTTTGCTACACATCAACCCGATAAACTACGACCTGTTGTGCTAGTTCCAAAATTTTCAAGGCAAATG  800
 H  L  K  D  F  L  D  E  Y  L  W  F  A  T  H  Q  P  D  K  L  R  P  V  V  L  V  P  K  F  S  R  Q  M

CTTGATCGTAAACTTCTACTGGGTAACGTTCCGAAACAAATGAACTGCTTCAGTAGAGAATTCCACGTGGATCGAGTAGACGAAATGT              900
 L  D  R  K  L  L  L  G  N  V  P  K  Q  M  N  C  F  S  R  E  F  H  V  D  R  V  I  E  K  L  D  E  M  C

GTGATTTGGgtaagttgtccgagggaaactgatcttcagtttcagttttcaagcctggtcgattagtatttgattttcgagAGTCTTTTTCCTG        1000
 D  L                                                                                E  S  F  F  L TTTCTTCACGGACGCTCTGGATCAGGAAATCCGTCACGAAGCACTGTCGAAATCAGATCAACTCATTGGAATgtaagattttgaaactgtt            1100
 F  L  H  G  R  S  G  S  G  K  S  V  I  A  S  Q  A  L  S  K  S  D  Q  L  I  G  I
```

FIG. 8B

```
tctgaataagcgaaataagacactacgactttaaaaggaatcataagatgatatctcgcagtgaaaagcaaatattcagcacacaaaattttaaatt    1200
cagaaattaggaatcaaacatatcttcaagttttttgtaatccaagaaaaggactcaattaaataatctaaattctgtcagcattctcttttctaatat    1300
cttttatttattcaactattatttaagaccattttattcaactattattttaagAAACTACGATTCTGTCGTG    1400
                                                       N Y D S V V
TGGCTCAAGATAGGCGAACAACGGCGAAAGCCACATTCGATTTATTCACAGATCTACTGCTGATGCTCAAgtgagtctctaatcttgtccagtgaaaaaa    1500
W L K D S G T T P K A T F D L F T D L L L M L K
gacacaagcactgcacaaattcgagattatttcgcagaatatttttctcttgcactgtcgtgtttaaagacgagcccgtgtgtgagcgaca    1600
cggatgactcgcacacatgcccgacttcattaaccgtgtcttcttcaagAAGTGAAGACGACCTGCTCAATTTTCCGTCGAACACGTTACATCTGT    1700
                                                 S E D D L L N F P S V E H V T S V
TGTGCTGAAGAGAATGgtgagtctttcaaagattgctgagtctttgactgtatgtgacaaaaataaatggggtcttgactacgttagatcaatttacaccaatg    1800
V L K R M
ttgattgttgagttaaaaattcaattttttcaaATTGCGAACGCTCTCATTGACCGGCCAAATACTTTGTTCGTTCTTGATGATGGTTCAAGAAGACA    1900
                                  I A N A L I D R P N T L F V L D D V V Q E D T
CAATCCGTTGGGCTCAGGAACTTCGCTTGCTGTTTGATCACCACCAGAGATGTTGAAATTCAAATGCAGCTTCACCGGAATGCGAATTTATAGAAGT    2000
I R W A Q E L R L R C L I T T R D V E I S N A A S P E C E F I E V
```

FIG. 8C

```
CACACCGTTGGAAAGTTATGAATGCTTCGAATTGTTGGAATCATATGGCATGCCGGTGCTGTATTGAGAGAGACGAGGATATCTTACACAAACCATT   2100
 T  P  L  E  S  Y  E  C  F  F  E  L  L  E  S  Y  G  M  P  V  P  A  I  E  R  D  E  D  I  L  H  K  T  I

GATCTAACGAGCGGAAATCCAGCAGCTCTCATGATGATTTTCAAGTCATGCGAACCGAAAACATTCGAGACGAAgtgagtagtaatattaactcgtttc  2200
 D  L  T  S  G  N  P  A  A  L  M  M  I  F  K  S  C  E  P  K  T  F  E  K ccgaaaaaaaaagaatttccgtttcgtttggccgtaaagacaaaatgtctcttccgtttgacgtcagtttttcagcagaaacgggatggaac  2300 agttgattttttcagttttccggaagactttcgaagattctcttccattccgtttccatagaaaaaattttaaattttgttttcctcttgccggaaataa  2400 tttaactcactaaaaaaaaggttttttcatctcaatataccacctaaagaatgcccaaaaaaaaatacattttttcagGATGGCCCAGCTGAACAGTAAACTG  2500
                                                                                M  A  Q  L  N  S  K  L GAAACTCGTGGATTATCTGCAATTGAATGTATCACTCCCTACTGTTATAAGTCACTATCTAGTTCTCCAACGATGTGCGAAGTTCTTTCGGATGAAG  2600
 E  T  R  G  L  S  A  I  E  C  I  T  P  Y  C  Y  K  S  L  S  S  S  L  Q  R  C  V  E  V  L  S  D  E  D ATCGCAGCGCTTTGGCTTTTGCTGTTATCATGCCTCCAGGAATAGACATTCCTGTCAAATATGGTCTGCGTCATTCCAGTGGATATATGTTCCAACGA  2700
 R  S  A  L  A  F  A  V  I  M  P  P  G  I  D  I  P  V  K  I  W  S  C  V  I  P  V  D  I  C  S  N  E AGAAGATCAGTAGATGACGAAGTGGCGGATCGGGTTGAAGAGATTAAGCAAgtaagatgctgttcggtattatgaatctctctaacactgatttacag  2800
 E  D  Q  L  D  D  E  V  A  D  R  L  K  R  L  S  K AAGAGGAGCTCGCTCAGTGGAAAACGGTTCCCCGTTTTGACCTATAAAATAGATCATGTCATTCATTCTATTCCTGAAGCACGTGGTTGATGTTCAGACG  2900
 R  G  A  L  L  S  G  K  R  S  P  V  L  T  Y  K  I  D  H  V  I  H  L  F  L  K  H  V  V  D  V  Q  T ATTGCAgtaagtaatactcatagagaaaattttatttcagaaatcaaaaactctcaattaactaattcagtcccttataaaatttgtgttcagcg  3000
 I  A
```

FIG. 8D

```
aaagttccataaattaatctttttcacagAATGGAATCTCGATTCTTGAACAACGTCTTCATGAGCTTGGAAATAACAACACGGCTACACCAGAAAGAC    3100
                              N  G  I  S  I  L  E  Q  R  L  H  E  L  G  N  N  N  T  P  T  P  E  R  H ATATGCCATCAAATTCCGTCGTACATCTGCTGGTGACATGTTTCCAAAAGTGGAAGATTCTGTTATACGCCCAGAGATTATTCAAAATTCATGCAAAT    3200
 M  P  S  K  F  R  R  T  S  A  G  D  M  F  P  K  V  E  D  S  V  I  R  P  E  D  Y  S  K  F  M  Q  I CCATCGGACTTTCTATGATTCCCTAAAGAAGTTCACATCCCAATAGCTGTATAAGAATTTCTATGCCTGTAATTCTTCCATATAATTATTCGCATGT    3300
 H  R  T  F  Y  D  S  L  K  K  F  T  S  Q  *

AATATTTCTCCTATTCAGTATTTATTTGAGCACTTTCTGACTGTATTTGTTTACCCAACCCCCTCCCCTTTAAGCTTTTTTTATTGTACGGATGA    3400

TAATCAGAATTTGTTGTTGATACTCAGAATCATAGnTCACAGGTTGATTTCTCTTAAATCGTTCCCCATCTGAATCCAAATTTGTTTCTTACTATAA    3500

ATATTATTGCATATGATCGTGTAGCTTTGTGCATTATGGTTGTTGTGATCTCTTATTCAAATATTATTTGTGCTTTAAAACAGCTAA    3600

TTTGATTATCCAGTTATGCAGTAGTTTCGAGAAGACCCCAACTTTATAAGTAATCACCACTGTGATACAGCTTCGAAAATGCGGTTCCTATCGTCTG    3700

CTGTCATTTCTACATTTGGCATCCTTTCCATATTATTGAAATGATATCCACCATTGGTTTGGTTTACGCCGTTTGGTCAATGGATTTCTCGGGCTAGAAGAGCTACATT    3800

ACATATTGTTCGTTGTATTTCTCGTTCCACAGCAACGGATATTTTTTAGTGGTTTACGCCGTCATCTTTCGTCGTGAGTTACAAGGAAGGAGGTTCTAAGCTTTTTCA    3900

CAACGAACATAATCTTCTGCTGACCTATCAACCAAGAGCTTACACACACGGTCATCTTTCGTCGTGAGTTACAAGGAAGGAGGTTCTAAGCTTTTTCA    4000

TCAAACATTTCCAGCCTGATCCACCGACACCATGCGGATTCTCGAAAAATCCAACTGAATCATGTACTGATTCGGAGTTTCGTCAAGCCCGT    4093

(SEQIDNo:5)
```

FIG. 8E ced-4 cDNA of Caenorhabditis briggsae

```
ATTGGCTCCGCTCATTGACTTTTCGAATACAATAATCAAATCATCTGAAGGACTTTCTTGATGAGTATCTGCTACACATCAACCCGATAAA  300
 L  A  P  L  I  D  F  F  E  Y  N  N  Q  N  H  L  K  D  F  L  D  E  Y  L  W  F  A  T  H  Q  P  D  K

CTACGACCTGTTGTGCTAGTTCCAAATTTCAAGGCAAATGCTTGATCGTAAACTTCTACTGGGTAACGTTCCGAAACAAATGACTGCTTCAGTAGAG  400
 L  R  P  V  V  L  V  P  K  F  S  R  Q  M  L  D  R  K  L  L  G  N  V  P  K  Q  M  N  C  F  S  R  E

AATTCCACGTGGATGCAGTGATCGAGTAGAAGTTAGACGAAATGTGTGATTGGAGTCTTTTTCCGTTCTTCACGGACGCTCTGGATCAGGAAATCCGT  500
 F  H  V  D  R  V  I  E  K  L  D  E  M  C  D  L  E  S  F  F  L  F  L  H  G  R  S  G  D  Q  E  I  R

CATCGGCGTCACAAGCACTGTCGAAATCAGATCAACTCATTGGAATAAACTACGATTCTGTCGTGGGCTCAAAGATAGGGACAACGCCGAAGCCACA  600
 I  A  S  Q  A  L  S  K  S  D  Q  L  I  G  I  N  Y  D  S  V  V  L  K  D  S  G  T  T  P  K  A  T

TTCGATTTATTCACAGATCTGCTGCTGAAAGTCGAAGACCACCTGCTCAATTTCCCGTCCGTCGAACACGTTACATCTGTTGTGCTGAAGAGA  700
 F  D  L  F  T  D  L  L  M  L  K  S  E  D  D  L  L  N  F  P  S  V  E  H  V  T  S  V  V  L  K  R  M

TGATTGCGAACGCTCTCATTGACCGGCCAAATACTTTGTTCTTGATGATGGTTCAAGAGACACAATTCGGTCAGGAACTTCGCCTTCG  800
 I  A  N  A  L  I  D  R  P  N  T  L  F  V  L  D  D  V  V  Q  E  D  T  I  R  W  A  Q  E  L  R  L  R

CTGTTTGATCACCAGAGATGTTGAAATTTCAAATGCAGCTTCACCGGAATGCAGGAATTTATAGAAGTCACACGGTTGGAAAGTTATGAATGCTTCGAA  900
 C  L  I  T  T  R  D  V  E  I  S  N  A  A  S  P  E  C  E  F  I  E  V  T  P  L  E  S  Y  E  C  F  E

TTGTTGGAATCATATGGCATGCCGGTGCCTGCTATTGAGAGAGACGAGGATATCTTACACAAACCATTGATCTAACGAGGGAAATCCAGCAGCTCTCA  1000
 L  L  E  S  Y  G  M  P  V  P  A  I  E  R  D  E  D  I  L  H  K  T  I  D  L  T  S  G  N  P  A  A  L  M
```

FIG. 9B

```
TGATGATTTCAAGTGCATCATGGCAGAACCGAAACATTCGAGAAGATGGCCCAGCTAAACTCGTGGATTATCTCGAATGAATGTATCAC 1100
 M  I  F  K  S  C  E  P  K  T  F  E  K  M  A  Q  L  N  S  K  L  E  T  R  G  L  S  A  I  E  C  I  T

TCCCTACTGTTATAAGTCACTACTATCTAGTTCTCTCCAACGATGTGTCGAAGTTCTTTGGCTTTTGCTTTGCTGTTATCATGCCT 1200
 P  Y  C  Y  K  S  L  S  S  S  L  Q  R  C  V  E  V  L  S  D  E  D  R  S  A  L  A  F  A  V  I  M  P

CCAGGAATAGACATTCCTGTCAAAATATGGTCTTGCTGTCATTCCAGTGGATATGTTCCAACGAAGAATCAGTGAAGATGACGATCGGT 1300
 P  G  I  D  I  P  V  K  I  W  S  C  V  I  P  V  D  I  C  S  N  E  E  D  Q  L  D  D  E  V  A  D  R  L

TGAAGAGATTAAGCAAAGAGGAGCTCTGCTCAGTGGGAAAACGGTCCCCGTTTGACCTATAAATAGATCATGTCATTCATCTATTCTGAAGCACGT 1400
 K  R  L  S  K  R  G  A  L  L  S  G  K  R  S  P  V  L  T  Y  K  I  D  H  V  I  H  L  F  L  K  H  V

GGTTGATGTTCAGACGATTGCAAATGGAATCTCGATTCTTGAACAGTCTTCATGAGCTTCATGAGCTTCATGAGCTACACCAGAAGACATATGCCA 1500
 V  D  V  Q  T  I  A  N  G  I  S  I  L  E  Q  R  L  H  E  L  G  N  N  N  T  P  T  E  R  H  M  P

TCAAATTCGTTGATCTGCTGGTGACATGTTTCCAAAGTGGAAGATTCTGTATACGCCCAAGAATTATTCAAATTCATGCAAATCCATCGCA 1600
 S  K  F  R  R  T  S  A  G  D  M  F  P  K  V  E  D  S  V  I  R  P  E  D  Y  S  K  F  M  Q  I  H  R  T

CTTTCTATGATTCCCTAAAGAAGTTCACATCCCAATAG
 F  Y  D  S  L  K  K  F  T  S  Q  *       (SEQIDNo:6)
```

FIG. 9C

OLIGOMER DATA SET FOR PROGRAMMED CELL DEATH HOMOLOGUE CLONING

| Oligo | | Sequence | Description .. |
|---|---|---|---|

! Oligomers used in obtaining the disclosed invention.

| | | | |
|---|---|---|---|
| 397 | 0 | CGAATTCGGATCCGARCAYGTNACNTCNGT | (SEQIDNo:7) |
| 398 | 0 | CGAATTCGGATCCGTNCARGARGARACNAT | (SEQIDNo:8) |
| 399 | 0 | CGAATTCGGATCCGTNGCNGGRTTNCCRCT | (SEQIDNo:9) |
| 484 | 0 | CATCGATGGATCCTTYTTYCTNTTYCTNCAYGG | (SEQIDNo:10) |
| 485 | 0 | CGAATTCGGATCCACNGANGTNACRTGYTCNAC | (SEQIDNo:11) |
| 489 | 0 | CGAATTCGGATCCTTYTCRAANGTYTTNGGYTC | (SEQIDNo:12) |
| 501 | 0 | CGAATTCGGATCCTTYTCRAANGTYTTNGGYTC | (SEQIDNo:13) |
| 502 | 0 | CATCGATGGATCCACNGANGTNACRTGYTCNAC | (SEQIDNo:14) |
| 511 | 0 | CATCGATGGATCCGTNTGGCTNAARGAYAGYGG | (SEQIDNo:15) |
| 512 | 0 | CGAATTCGGATCCTCRAGNGTYTTNGGYTCRCA | (SEQIDNo:16) |
| 513 | 0 | ACNATHAGRTGGGCNCARGA | (SEQIDNo:17) |
| 514 | 0 | ACNATHCGNTGGGCNCARGA | (SEQIDNo:18) |
| 517 | 0 | CATCGATGGATCCGGNAAYGTNCCNAARCARAT | (SEQIDNo:19) |
| 518 | 0 | CGAATTCGGATCCATNCCRTTNGCDATNGTYTG | (SEQIDNo:20) |
| 519 | 0 | GAYGAYGTNGTNCARGARGA | (SEQIDNo:21) |
| 520 | 0 | CGAATTCGGATCCATRTCNACNGGDATNACRCA | (SEQIDNo:22) |
| 526 | 0 | TGYGARCCNAARACNTTYGA | (SEQIDNo:23) |
| 570 | 0 | CGAATTCGGATCCTGNGCCCANCGDATNGTYTC | (SEQIDNo:24) |
| 571 | 0 | CGAATTCGGATCCTGNGCCCAYCTDATNGTYTC | (SEQIDNo:25) |
| 572 | 0 | CATCGATGGATCCACNMGNGAYGTNGARATHTC | (SEQIDNo:26) |
| 573 | 0 | CATCGATGGATCCACNMGNGAYGTNGARATHAG | (SEQIDNo:27) |
| 574 | 0 | ACACTGCAGTCRAANGTYTTNGGYTCRCA | (SEQIDNo:28) |
| 575 | 0 | ACACTGCAGAYTTYGARCCNCGNGAYGC | (SEQIDNo:29) |
| 576 | 0 | ACACTGCAGAYGAYGTNGTNCARGARGA | (SEQIDNo:30) |
| 577 | 0 | ACACTGCAGTNTGGYTNAARGAYAGYGG | (SEQIDNo:31) |
| 586 | 0 | ATACTCGAGCCACCATGCTTTGTGAAATCGAATG | (SEQIDNo:32) |
| 587 | 0 | ACTCTCGAGCTATTGGGATGTGAACTTCTTTAG | (SEQIDNo:33) |
| 624 | 0 | AACACTGCAGTNTGGYTNAARGAYTCNGG | (SEQIDNo:34) |
| 625 | 0 | AACACTCCAGTCYTCYTGNACNACRTCRTC | (SEQIDNo:35) |
| 627 | 0 | AACACTCCAGATYTCNAGRTCYCTNGTNGT | (SEQIDNo:36) |

| FIG. 11A |
|----------|
| FIG. 11B |

Partial mec-4 cdna of Caenorhabditis elegans

```
GGAATGGGATGGAATGGAAGAGATATGACAATTGAGAATTACGATTGGAAGCAACTACTGGAATGATGAAGAATGTCAATCAGAG   100
 E  W  D  G  M  E  E  Y  D  N  E  H  Y  E  N  Y  D  V  E  A  T  T  G  M  M  E  E  C  Q  S  E

AGAACAAATTCGACGAGCCGACGGGATTTGACGATGACCGATGTATTTGCGCTTTCGATAGATCAACTCATGATGCGTGGCCCTGTTTCTGAACGGAACCT   200
 R  T  N  S  T  S  P  T  G  F  D  D  D  R  C  I  A  F  D  R  S  T  H  D  A  W  P  C  F  L  N  G  T  W

GGGAAACCACCGAATGTGATACTTGCAATGAACATGCTTCTGCACCAAAGATAACAAACTGCGAAGGGCATAGATCCCATGTATTTGTGCTCATC   300
 E  T  T  E  C  D  T  C  N  E  H  A  F  C  T  K  D  N  K  T  A  K  G  H  R  S  P  C  I  C  A  P  S

TAGATTCGTGTAGCATACAACGGAAAGACGCCACCAATTGAAATTTGGACATATCTTCAAGGAGGAACTCCAACTTCCTTGAAGCT   400
 R  F  C  V  A  Y  N  G  K  T  P  P  I  E  I  W  T  Y  L  Q  G  G  T  P  T  E  D  P  N  F  L  E  A

ATGGGATTTCAGGGAATGACAGATGAAGTTGCACTGTTTGCAATGGCTACCTTGTCAATGCAAGATAGGGAAC   500
 M  G  F  Q  G  M  T  D  E  V  A  I  V  T  K  A  K  E  N  I  M  F  A  M  A  T  L  S  M  Q  D  R  E  R

GGCTAAGTACTACAAAAGGGAACTTGTCCACAAGTGCTCGTTTAACGGAAAAGCGTGTATATCGAAGCAGATTTTCTGACTCATATTGACCCTGCGTT   600
 L  S  T  T  K  R  E  L  V  H  K  C  S  F  N  G  K  A  C  D  I  E  A  D  F  L  T  H  I  D  P  A  F

TGGTTCGTGCTTTACTTCAATCATAATCGAACAGTAACTTGACTAGTATTCGAGCAGGTCCATGTACGGATTACGTATGCTGGTTTATGTAAACGCG   700
 G  S  C  F  T  F  N  H  N  R  T  V  N  L  T  S  I  R  A  G  P  M  Y  G  L  R  M  L  V  Y  V  N  A
```

FIG. 11A  PRIOR ART

```
TCTGACTATATGCCAACCACGGAGCCACAGGCGTTCGTTTGACTATTCATGACAAAGAGATTTCCCATTTCCTGATACGTTCGTTATTCTGCTCCAA    800
 S D Y M P T T E A T G V R L T I H D K E D F P F P D T F G Y S A P T
CTGGATATGTATCCTCATTTGGATTACGATTGCGAAAGATGTCACGTTTGCCAGCACCTTATGGAGATTGTGTGCCAAACATCGGACTATAT        900
 G Y V S S F G L R L R K M S R L P A P Y G D C V P D G K T S D Y I
TTACAGCAATTATGAATATTCGGTAGAGGGCTGCTACGTTCTGCTTCCAACACTCGTCTGCTGAAGAGTGCAGATGTGGAGATCCACGTTTCCAGTC   1000
 Y S N Y E Y S V E G C Y R S C F Q Q L V L K E C R C G D P R F P V
CCTGAAAATGCACGGCATTGCGATGCAGCAGACCCTATTGCAAGAAATGTCTTGACGCCAGATGAATGACTTGGGAGGCCTACACGGATCTTTCCGTT  1100
 P E N A R H C D A D P I A R K C L D A R M N D L G G L H G S F R C
GCAGATGCCAACAACCATGCGGCAGTCAATCTACTCCGTTACATACTCCGTTACATACTCGTTATCTTTGCAAATTCAACTAGGATCGTGTAA       1200
 R C Q Q P C R Q S I Y S V T Y S P A K W P S L S L Q I Q L G S C N
TGGTACAGGCGGTAGAGTGTAATAAGCATTATAAAGAGAACGAACCGGAAGTGTTCTACGAGCAGTTGAATTTGAATGTCACTGAATCAGAG        1300
 G T A V E C N K H Y K E N G A H V E V F Y E Q L N F E M L T E S E
GCTTATGGGTTTGTCAACTTGCTAGCCGATTTTGGTGGACAACTCGGTCTTGTTGGCAATATCCTTCCTGTTGCGAATTGGTGTTCCTTTCT       1400
 A Y G F V N L L A D F G G Q L G L W C G I S F L T C C E F V F L F L
TGGAAACTGCCTACATGAGTGCCAACATAACTACTCTCTACAAAGAGGCTGAGAGGCAAGAAATTGGTCTGGATCTTTCTGAATTTG            1500
 E T A Y M S A E H N Y S L Y K K K A E K A K K I A S G S F *
TTTTTTCTTGTTTAAAGTTACCATTGCAATGTTGTCTTAAATAAAATTACATGAGATATAAAAAAAAAAAAAAAAAAAAAAAAAAAAA             1600
(SEQ ID No: 37)
```

FIG. 11B
PRIOR ART mec-4 gene of Panegrellus redivivus

```
GGTACGGCCGATTGTACCTGTAGTGGCCGAATTACCAGCATGGAGTGTGATACAGATGTAACAGCACCGAATCTGAAGAGAAACATGTTTATGGCC  500
         Y  D  C  T  C  S  G  R  I  T  S  M  E  C  D  T  D  V  N  S  T  P  K  S  E  E  E  T  C  L  C  A

GTTTGATCAGATAGGGCGGATGCTTGGCCATGTACCCAAAGATAAATGGGAAGAACACACATGTAAATTTGTGATGAACACATGTCTGTACTATT  600
  F  D  R  D  S  G  D  A  W  P  C  Y  P  K  D  K  W  E  E  H  T  C  K  F  C  D  E  H  N  V  C  T  I

GACGAAAAGCTGGCATACTCCAGTAGCTACGTTATGTCTTGCCAACTATCATTCATTCTGTGTTGCTTCAACAAGATCGGCTATATTGAAGC  700
  D  E  K  A  G  I  P  P  V  A  T  L  C  L  C  Q  T  I  N  P  F  C  V  A  F  N  K  E  S  A  I  L  K  L

TATGGGATACTATGGCGAAGGAAGTAGTCGTCACGAAAGCCAAGGAAATTCATGATTGGAAGCATTGGTTGAAGTTTTAGTTCTCGGCACCGTTTTCTATTATGTTG  800
  W  E  Y  Y  G  S  G  I  H  D  P  K  V  V  E  A  L  G  F  A

TTTTAGAATATGAGGACGAAGTAGCTATCGTCACGAAAGCCAAGGAAAACATTATTTTTGCTATGTCAGCACTTCTCATCAACAAGAACATGTTAT  900
  M  S  D  E  V  A  I  V  T  K  A  K  E  N  I  I  F  A  M  S  A  L  S  I  Q  R  T  M  L  S

CTATCCAAAACATCAACTGATTCAAAAGTGCTCGTTAATGGAATTGTGACATTGCTTGTGACATTGATAAGTAAGTTAACCGATTCGATTCAAGTTCAAGAA  1000
  I  Q  K  H  Q  L  I  Q  K  C  S  F  N  G  I  A  C  D  I  D  K

GGATGTTTAGAGACTTTGAAATCCTAGTAGATCCAACCTTTGGAAATTGCTTCACTTTCAACCACAATCGCACCCAAACATTGAGCAGCATTCGCGCAG  1100
         D  F  E  I  L  V  D  P  T  F  G  N  C  F  T  F  N  H  N  R  T  Q  T  L  S  S  I  R  A  G

GTCCCATGTACGGTTTACGCATGCTTATTTCGTCAATGTATCAGAATTATTTGCCACAACAAGAGCAGTTGGTGTCAGAATTACGATACGACAAAGA  1200
  P  M  Y  G  L  R  M  L  I  F  V  N  S  E  Y  L  P  T  T  E  A  V  G  V  R  I  T  I  H  D  K  E

AGACTATCCATTCCCGGTAATCAATTCTTCCATTAAGTCAACAATGTCTTCATTGTATACATTTAATTTCCCAATGACCTTTCAGGACAC  1300
  D  Y  P  F  P                                                                           D  T
```

FIG.12B

```
ATTTGGCTACAGGGCACCCACTGGTTTATTTCCTCTTTGGCATGAATGACCCGAATGTGCGGCGTATGGCGGATTCCCGATGGG  1400
 F G Y S A P T G F I S S F G M R M T R M S R L R A Y G D C I P D G

TTGACCACCAATTACATTTACAAGGGCTACCGTTACTCGACAGAGTAATAGTTCTATGATTAAGCCAATTGTCCAGTGACTCTTCAATTGAATGCTTTT  1500
 L T T N Y I Y K G Y R Y S T E

AGGGTTGTATCGCACATGTTTCAAGAATTGTACTTAATGACTGTCTTAACCAATAAATCACATTGTCAAGT  1600
 G C Y R T C F Q E L V L N D C G C G D P R F P V L T N K S H C Q V

GTTTGATCCAGCTGCACGTAAATGTCTTGAGCAACGGACAATGACCTGAGCAATGTTCACGGAGTTTCGATGTAGATGCCAGCAGCCGTGTGACCAG  1700
 F D P A A R K C L E Q R T N D L S N V H G S F R C R C Q Q P C D Q

TCTGTGTACACAGTTTCTTATTCCGAAGCGAATTGGCCAAGTACTTCGTTGAATATTTCACTGGGAACTGTGATAAGGGCCGGATTTGTGCAATGAAC  1800
 S V Y T V S Y S E A N W P S T S L N I S L G N C D K G P D L C N E H

ATTACATGTAAACATTGAAATCAGAAGCCTATGGCGTAAGTCACTCCTCTGTTATCACAGTTAATATCATAAGCACTTCAACTTGTCAGATAGTCAAATG  1900
 E N G A M I E V F Y E A L N                       I V K M
 Y M

TTTCGAAGTATTTACAGAATCAGAAGCCTATGGCGTAAGTCACTCCTCTGTTATCACAGTTAATATCATAAGCACTTCAACTTGTCAGATAGTCAAATG  2000
 F E V F T E S E A Y G

CTTGCCGATTTCGGGGCCAACTTGGTCTCTGGTCAGGCGGTAAGCTTCATTACTATGTGGAATTCACATTTCTTGCTCTTGAAATTATCTACATGGTAT  2100
 L A D F G G Q L G L W S G V S F I T M C E F T F L A L E I I Y M V F

TTAATCATCATTACAACATTTACAATGGAAAAACAGCCGAAGCCTTTAAACATTGTATGCCACTCTGAGAGCAAATGGATACG  2200
 N H Y N I Y K R K K Q A E E E N G L *

TGAATTGACATTTAATCAATTAATTCAGTATGTTGTTCAATGAAGGGCATTGTTATTCGGCACAAT    (SEQIDNo:38)
```

FIG.12C

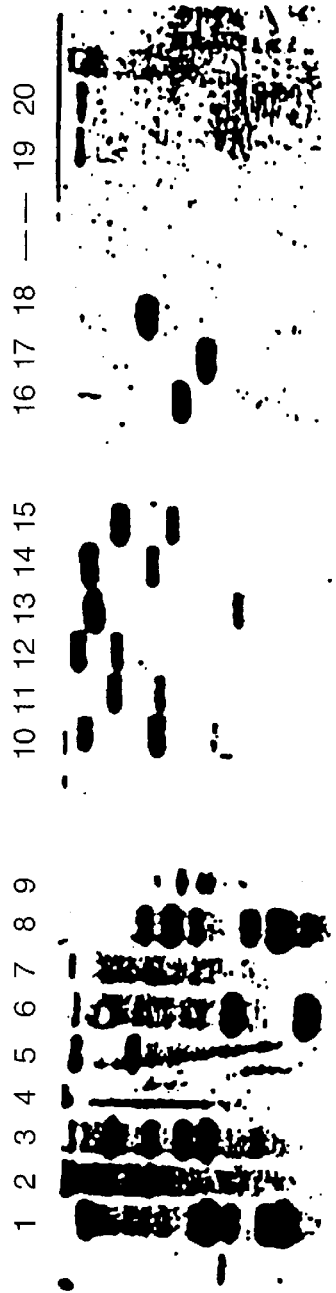

FOUR-BASE RESTRICTION ENZYME ANALYSIS OF HYBRIDIZING CLONES.

CLONES WERE ISOLATED USING RADIOLABELLED FRAGMENTS OF cDNA TO PROBE GENOMIC LIBRARIES (VECTOR = EMBL III) AT REDUCED STRINGENCY. THREE MICROGRAMS OF PHAGE DNA PREPARATIONS WERE DIGESTED TO COMPLETION WITH SELECTED RESTRICTION ENZYMES AND SAMPLES WERE ELECTROPHORESED THROUGH 3% NuSieve- 1% AGAROSE GETS (3 HOURS, 2 V/xm, TRIS-ACETATE-EDTA BUFFER) AND BLOTTED TO NYLON FILTERS. THE FILTERS WERE HYBRIDIZED AND WASHED AT REDUCED STRINGENCY THEN EXPOSED TO FILM WITH AN INTENSIFYING SCREEN. HYBRIDIZING GENOMIC DNA CLONES WERE ISOLATED FROM A C. BRIGGAE LIBRARY USING A C. ELEGANS ced-4 cDNA PROVE, LANES 1-9; A P. REDIVIVUS LIVRARY USING A C. ELEGANS mec-4 PROBE, LANES 10-15; A HUMAN LIBRARY USING A C. ELEGANS ced-4 PROBE, LANES 16-20. ENZYMES USED IN THE EXPERIMENT WERE: Alu I (1, 10, 16), BstNI (2,11,17), DdE I (3,12,18), Hae III (4,13), Hinf I(5,14), Msp I (6,15,19), Sau3AI (7,20), Taq I (8), AND Xho II (9).

| FIG. 14A |
| FIG. 14B |

FIG. 14A

DEGENERIN OLIGOMER DATA SET oligo    sequence

Degenerate PCR primers
330   0  CATCGATGGATCCCCNTTYCCNGAYACNTTYGGNTA! (SEQIDNo:39)
381   0  CGAATTCGGATCCGNACNGGRAAYCTNGGRTC! (SEQIDNo:40)
382   0  CGAATTCGGATCCGNACNGGRAANCGNGGRTC! (SEQIDNo:41)
387   0  GCGAATTCGGATCCTCNGGNACNGGRAANCKNG! (SEQIDNo:42)
389   0  GCATCGATGGATCCCCNTTYCCNGAYACNTTYGG! (SEQIDNo:43)
392   0  GCATCGATGGATCCCCNGAYACNTTYGGNTA! (SEQIDNo:44)
393   0  GCGAATTCGGATCCNACNGGRAAYCTNGGRTC! (SEQIDNo:45)
394   0  GCGAATTCGGATCCNACNGGRAANCGNGGRTC! (SEQIDNo:46)
435   0  GCAATTCGGATCCCCNGAYACNTTYGGNTAYTC! (SEQIDNo:47)
436   0  GCATCGATGGATCCCCNGAYACNTTYGGNTAYAG! (SEQIDNo:48)
437   0  GCGAATTCGGATCCNACNGGRAAYCTNGGRTCNCC! (SEQIDNo:49)
438   0  GCGAATTCGGATCCNACNGGRAANCGNGGRTCNCC! (SEQIDNo:50)
504   0  CATCGATGGATCCGAYGARGTNGCNATHGTNAC! (SEQIDNo:51)
505   0  CATCGATGGATCCATHGTNACNAARGCNAARGA! (SEQIDNo:52)
506   0  CGGATTCGGATCCCCRTACATNGGNCCNGCNCG! (SEQIDNo:53)
507   0  CGAATTCGGATCCCCRTACATNGGNCCNGCYCT! (SEQIDNo:54)
566   0  CGAATTCGGATCCACNTTYGGNTAYTCNGCNCC! (SEQIDNo:55)
567   0  CGAATTCGGATCCACNTTYGGNTAYAGYGCNCC! (SEQIDNo:56)
584   0  CGAATTCGGATCCGNGARTANCCRAGNGTRTC! (SEQIDNo:57)
585   0  CGAATTCGGATCCGNCNCTRTANCCRAANGTRTC! (SEQIDNo:58)
594   0  CATCGATGGATCCTAAAGATACTCTTTGCAATA! (SEQIDNo:59)
595   0  CGAATTCGGATCCTCCAACGTTTGCAACTGTT! (SEQIDNo:60)
628   0  CCGAATTCGGATCCGCNGGNCNATGTAYGG! (SEQIDNo:61)
629   0  AAGGATCCTGCAGGCNGARTANCCRAANGTRTC! (SEQIDNo:62)
630   0  AAGGATCCTGCAGGRCRCTRTANCCRAANGTRTC! (SEQIDNo:63)

Degenerate oligonucleotide probes

| | | |
|---|---|---|
| 262 | 0 | CCNTTYCCNGAYACNTTYGG! (SEQIDNo:64) |
| 410 | 0 | ACNTTYGGNTAYTCNGCNCC! (SEQIDNo:65) |
| 411 | 0 | ACNTTYGGNTAYAGYGCNCC! (SEQIDNo:66) |
| 418 | 0 | TTYCCNGAYACNTTYGGNTA! (SEQIDNo:67) |
| 419 | 0 | CCNGAYACNTTYGGNTAYTC! (SEQIDNo:68) |
| 420 | 0 | CCNGAYACNTTYGGNTAYAG! (SEQIDNo:69) |
| 421 | 0 | GAYACNTTYGGNTAYTCNGC! (SEQIDNo:70) |
| 422 | 0 | GAYACNTTYGGNTAYAGYGC! (SEQIDNo:71) |
| 447 | 0 | ACNGGRAAYCTNGGRTCNCC! (SEQIDNo:72) |
| 448 | 0 | ACNGGRAANCGNGGRTCNCC! (SEQIDNo:73) |
| 490 | 0 | GARCAYTAYAGYCCNGAR! (SEQIDNo:74) |
| 491 | 0 | GARCAYTAYTCNCCNGAR! (SEQIDNo:75) |
| 492 | 0 | TGYTAYAGYGCNCCNACNGG! (SEQIDNo:76) |
| 493 | 0 | TGYTAYTCNGCNCCNACNGG! (SEQIDNo:77) |
| 556 | 0 | GAYGARGTNGCNATHGTNAC! (SEQIDNo:78) |
| 557 | 0 | ATHGTNACNAARGCNAARGA! (SEQIDNo:79) |
| 558 | 0 | CCRTACATNGGNCCNGCNCG! (SEQIDNo:80) |
| 559 | 0 | CCRTACATNGGNCCNGCYCT! (SEQIDNo:81) |
| 560 | 0 | TTYAAYCAYAAYAGRACNCA! (SEQIDNo:82) |
| 561 | 0 | TTYAAYCAYAAYCGNACNCA! (SEQIDNo:83) |
| 565 | 0 | TGYTTYACNTTYAAYCAYAA! (SEQIDNo:84) |
| 582 | 0 | TGYTTYACNTTYAAYCAYAAYAG! (SEQIDNo:85) |
| 583 | 0 | TGYTTYACNTTYAAYCAYAAYCG! (SEQIDNo:86) |
| 631 | 0 | NGCYTCNGTNGTNGGCAT! (SEQIDNo:87) |
| 635 | 0 | GCNCCNTTYCCNGCNATAAC! (SEQIDNo:88) |
| 636 | 0 | TGYAAYCTNAAYCCNTAY! (SEQIDNo:89) |
| 637 | 0 | TGYAAYTTYAAYCCNTAY! (SEQIDNo:90) |

FIG.14B

DEVELOPMENT OF PROBES AND PRIMERS

OBJECTIVE: FIND THE SPECIFIC SETS OF PCR PRIMERS THAT CAN AMPLIFY APPROPRIATE TARGET SEQUENCES IN DISTANT NEMATODES.
BACKTRANSLATE OF: :Areal.Pep ProPheProAspThrPheGlyTyrSerAlaPro

CCNTTYCCNGAYACNTTYGGNTAYWSNGCNCCN (SEQIDNo:140)

| PROBES (20mers) | DEGENERACY | RESULTS |
|---|---|---|
| 262 | 512 | - |
| 418 | 512 | - |
| 419, 420 | 512, 512 | + |
| 421, 411 | 512, 256 | + |
| 410, 411 | 1024, 512 | + |

PRIMERS

392

435 (S: TCY)

436 (S: AGN)

FIG.15

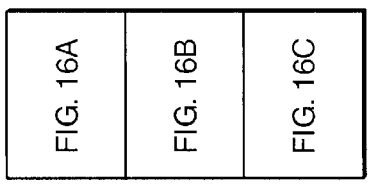

FIG. 16A

PCR product of deg-3 gene of Panegrellus redivivus

```
                                                                                        100
TTTGGGTATTCGGCCACCGACAGgCTTTGTTCCAGTTTTGGGTTGAAaCGGTAAGCAATTACACTTGTTAACCTTTCGAAAAAGGGTTTCAGAAG
 F  G  Y  S  A  P  T  G  F  V  S  S  F  G  L  K  T                                    K  V
                                                                                        200
TGTTGCATCGACTAAACGAACCATATGGCATGTGTAGTACTACCTTTCGGCCAGAGGGTACATTTATGCGAACATTACTCACCTGAGGTAATGTTTTG
 L  H  R  L  N  E  P  Y  G  M  C  S  D  T  F  R  P  E  G  Y  I  Y  A  E  H  Y  S  P  E
                                                                                        300
TTCAATTTGACCTCTTTAACATTGATTTTTgCAGGGTTGTATCGAAACTGTTTCCAACACATGATTCTGACGTGTGGGCTGTGGGCGayCCCmGmT
         G  C  Y  R  N  C  F  Q  H  M  I  L  D  T  C  G  G  D  P  X
                      (SEQIDNo:91)
```

PCR product of deg-3 gene of Ascaris suum

```
TTTGGGTATAGTGCTCCAACAGGCTTTATTTCCTCCTTCGGTCTCAAACGGTAAGTCTTTTGAGAAGAGGGCACTTCGGATnTCGTCGACTTTGTAAT    100
 F  G  Y  S  A  P  T  G  F  I  S  S  F  G  L  K  T

GCGATGGTCCAATCAGACCGATAATCCCATCACTTCGACTAGAATGTATTTGttGCTTTTTgAAGCGTCagstttCAGTGTTGTtCCACAGCTAgCTTC    200

AGTTACTATCAACATGAAGCCAAGAAGCTAATTGTACCTCTTACTCTCCAACTGaTATTACTTTATGTCAGTCTAGAATATTAACTGTATAGAGCCT    300

GCATAATAACCAGTAGAGACTGtwwskgCCATCTCATAACTCCTTCCCACCCACTTCAttGaTTTcCgTTATGCCTATACCGAATCAAACATTT    400 tAAGAAGGTGCTTCATCGCCTCGACGTCTTGCAGCGATACGTTCAGGCCAGAAGGTACATCTATCAGGAACACTACTCACCCGAGTG    500
 K  V  L  H  R  L  D  A  P  Y  G  L  C  S  D  T  F  R  P  E  G  Y  I  Y  Q  E  H  Y  S  P  E

AATTCGAGTTCTTTGATGGCAAAATTCAGAGAAGCCATCGTCTTAGGTACCTAAGTGTGCTCGCTTTCATTTGTGGTATTTGATGAGTCGAAAATTG    600

ACTGCCCAGTTTGTTTCAAACgGTGGCCATTTCTTGTTCGTAACCAGCgCAAACTTTTAAATCTACAAGGCGCTTCTACAGGATTTCATTGCTCATGT    700

TTCGGCTCTCTGAGTGGGGCATTTGCAAACACTGGTTCAAAGGACATTTTTTGGGAAGGGyGAATnTAAACTTCAATATGAGTACAAATTTA    800

AGCAGGTGATACTACAATGGTGCTTTGATATCAATGAGAAAAACCAGGAATTCAGGGTTGTATCGCAACTGTTTCAACATATGGTTCTTGCTCAAT    900
 G  C  Y  R  N  C  F  Q  H  M  V  L  A  Q  C

GCGGCTGTGGCCACCCCGCTTCCCCGTCG
 G  G  D  P  R  F  F  P  V
                                     (SEQIDNo:92)
```

FIG. 16B

PCR product of deg-3 gene of Caenorhabditis elegans

```
TTCGGGTATAGTGCTCCAACTGGATTCATTCTTCATTTGGTCTTAAAACGGTATTTAAATACCCTTGAGAATCTGTTTGCAGAGTTCGATTTCAGAAAG    100
 F  G  Y  S  A  P  T  G  F  I  S  S  F  G  L  K  T                                              K  E

AACTACATCGTCTCAGTGCTCCATGGGGAATTGCAGTGACACATTCCGACCggTTCCATACATTACAACGACACTATTCTCCTGAGTATGTAACAT    200
 L  H  R  L  S  A  P  W  G  N  C  S  D  T  F  R  P  V  P  Y  I  Y  N  E  H  Y  S  P  E

TTCCCATTCTTAATCAAACATTTATATTTTCAGGGTTGCCATGAAATTGTTCCAATTGAAAGTACTTGAAATATGTGGCGATCCTAGGTTCC    300
 G  C  H  R  N  C  F  Q  L  K  V  L  E  I  C  G  G  D  P  R  F  P

CCGGCT                                                    (SEQIDNo:93)
 A
```

FIG. 16C

| FIG. 17A |
| FIG. 17B |
| FIG. 17C |

FIG. 17 deg-3 gene of *Panegrellus redivivus*

```
AATGCAACTTAAATTCGAGCCAGTCCATTCCCTGCTGCTACCGTATGCAATTTGATGCATTCAAGGCCAGTCAGTTGAAGCAGTACGAGGAAATCGA    100
 M  Q  L  K  F  E  P  A  P  F  P  A  A  T  V  C  N  L  N  A  F  K  A  S  Q

ACAGGGTACGTTCGAATGCCAATATATATTTGTCTTTTATTGCCTTTCAGTTCCAAGTCTGGGAGGCGCTATGAATACAATAGACCA              200

AACTCAACTAAATCCGAATTCCATCGTCTCGAAAAAGACACGTAATGTATGAGCCTGTCTACGTAAGATGGGTCTGTAACTTACCTGATGACCAATGTGT  300
                                                    C  V  C  N  L  P  D  D  Q  C  V

GCCACAACGCAACCCCTCACGAAAACACTTCTGTTTGCATGTGTTCGAaGATgCAACAACAGGCGATATTGGCCATGCTATCCAACGACTGTTTGG      400
 P  Q  R  N  P  L  T  K  N  T  S  V  C  M  C  F  E  D  A  T  T  G  D  I  W  P  C  Y  P  T  T  V  W

AATGAAAGGTTTGTACACTCCCATTTTCATTACAAAACTAACTTTTTCCTGTACTCGTACTCGTATTTTTGCTATTTTTACATAATTTTTCTT         500
 N  E  K
```

```
TCGGCCCAGAAGGTACACATTTATGGGAACATTACTCACCTGAGGTAATGTTTGTTCAATTGACCTCTTAACATTGATTTTGCAGGGTGTATCG   1700
 G P E G Y I Y A E H Y S P E                               G C Y R

AAACTGTTCCAACACACTATGATTCTCGACACGTGTGGCTGTGACCCTCGGTTCCCCTTACCTTCTGACAAGGAAAAACCCTGCGACGCCGAAATGCC   1800
 N C F Q H M I L D T C G C G D P R F P L P S D K E K P C D A R N A

CGTGAGGCAACTTGTTAACTAATTGACCACCATCTCCAACATGATTGCCACTGTGTTCAACATGTACGAAAATGTCT   1900
 R E R T C L T N L T T I L G G F H H L Q H D C H C V Q P C T E N V F

TTGAAACGGGTATTCAGACTGCATGGCCTGCAATTAACTTTAATATTGGCGCAGACTGTCCAGCAGTATACCACATATCTAATGATTCAAAAGCTTG   2000
 E T A Y S A A A W P A I N F N I G A D C P A V Y H I S N D S K A C

TGCAGAATATTACCGGTAACTGTGCGTTCCAACAACTTGTCGTTTTAATATGTCTTAATATGTCTTAATGACTAACAGCTATATTGAAA   2100
 A E Y Y R                                             L N T A Y I E I

TCTATTACGAACAACTCAACTTTGAAACATTAAAGAAACTGCTGGTTATACTGTACGTTTATTACATATAGCTTTCCAAGACAAACAAAACCATGTTT   2200
 Y Y E Q L N F E T L K E T A G Y T

TAGCTTGTCAACCTTTTCTCCGATTCGGTGGTAACATTGGTCTCTGTAATTACATGTTGAAGTCGGTGAAGTCTTATGTGAAA   2300
 L V N L F S D F G G N I G L W I G F S V I T M F E V V L C E I

TCATTATTTATCGTACGCATTCGCTTTTAAGCTCTTCATATCTAATTACTACCTTCCCAGGAAAACACACCGCATTTATCAACGAAGCGC   2400
 I I Y I G T H S L F K L F I S K L L P S Q E N N H T A F I N E S A

AGAAAGAATCGCCAAAACGAGAATGAAATGAACTTCCTCCAACGATAATCGAACAAGAGAAGAAGTATCGACTCGACATTCGGAAGCTCAG   2500
 E R I A K T R N K *                                  (SEQIDNo:94)
```

FIG. 17C mec-4 gene of Ascaris suum

```
TTCCAGAACATGAGCGATGAGGTGGCCATTGTAACGAAGGCaAaGGAAAATCTCATATTTGCCATGTCTGAGTGTATCCAAGGCTCAAGGCTATCGGCTCT    100
      M  S  D  E  V  A  I  V  T  K  A  K  E  N  L  I  F  A  M  S  E  L  S  K  A  Q  R  I  A  L  S

CTGCTCAAAAGACAACTCATTCAAAATGTTCATTCAACGgCTGAATGTAACATCGAGAAGTTGGTTCACTCTTCCTtGAATAAGGACTTTTGT            200
   A  Q  K  R  Q  L  I  Q  K  C  S  F  N  G  A  E  C  N  I  E  K tTTTGGATTTCCTTtCAATGAAGCaTATGCAACATAAgCGGAgCGCCATTTATTTCGAATGCATAAArrGAGCAAGTGAGATATTGgAAAGAGCATt        300

TTTATGCTTTTTATCCTGTTGGATGGGATGATCAGCAAGAATTAGACACAAAGTGTCCAAAAgCACGACTTCAAGAAGCAGKGTA                    400

GAGrAGGTGGAATGAGTAGGGATATGTGATCATAACTCTCTTCGCCCTCTGCTCAACGTGCCACTTATTGATCaATACCGTAAAGAAGCATTGTCGTCG      500

ATGCTGGATATGCCACTATTYAGTGTAAAGCCAAATATTTTAAtTTTTTAGTCAGAAAATCAAGCCCTTGAAGCAaCCGAGGAAATAGATAgGAC          600

TCTACCAGCTTCATGCGAATTCTTTATCCTTTCTGTTCAGGATTGTAATTGAATCTAAATAGCTAAATGCTAACCCTTGAGGAAGAGCTCAT             700

TTAGGTCTAGCTCTGACTCCAGTGATATGTCATGTGTAATGACAGGAGAAAACTGCAGCAAGTGGACTCAATTCTATAATAAAGCAGAGATCGAGAG       800

TTCAAATCGGTCGCCATAGACGATGAAGACTCAGTGTAATGATGAAGATTTTGTAACGAAGTTTCTGCACGAGGGCGACATT                       900

ATAAATAGTTGCACGCAAGGATTTATTGTTGAGTTGTGGACGTAAAGCAGACTTCCTTGTTGCCGATCCAACGTTTGCCAACT                      1000
                                                                 D  F  L  V  V  A  D  P  T  F  G  N  C

GTTTCACATTCAACCACACAATCGAACAGAGAATAAAGTAGCATTCGCGCTGGTCCAATGTATGGTTAGGCCCTTAAATCAGCATATTATTGATGAGGAT    1100
 F  T  F  N  H  N  R  T  E  N  K  S  S  I  R  A  G  P  M  Y (SEQIDNo:95)
```

| FIG. 19A |
|----------|
| FIG. 19B |

Partial cDMA of Caenorhabditis remanei ced-4 gene1

```
ACATATTTGAAAGATCAAACATTTTTACGGAAGACCATCTAGACCTCATAAGCTCTATGCCTACTGACCAGAAGGATTGCTCAGTTCTACGAGCTT   100
 T  Y  L  K  D  Q  N  I  F  T  E  D  H  L  D  L  I  S  S  M  P  T  R  P  E  R  I  A  Q  F  L  R  A  Y

ATCGAAACAAGCTTCAGTTGGCACCACTCATCGACTCTTCATTTGTCAGATTTCATTTGTCAGATTTCTTTGAAGAACGCCTAAGTACCGC         200
 I  E  T  S  F  S  G  T  T  H  R  L  L  H  R  L  F  I  C  Q  I  S  F  V  R  F  L  K  N  A  *  V  P

AATTGAGAATCCCGAGTTGTACGGTCGGTATTGATATCTCCATTTTTGGAAAACAAATGCTGGAACGAAACTGTTATTGGGGAACGTTCCGAAACAA  300
 I  E  N  P  E  L  L  R  S  V  L  I  S  P  I  F  G  K  Q  M  L  E  R  K  L  L  L  G  N  V  P  K  Q

ATGGATTGTTACTGTAGAGCATATAACGTTGAAGGGRTTATCGAAAAGTTGAGCGATATGTAATCTCGGTTCTTCTTCTGTTCCTTCATGGTCGAG   400
 M  D  C  Y  C  R  A  Y  N  V  E  G  X  I  E  K  L  S  D  M  C  N  L  G  S  F  F  L  F  L  H  G  R  A

CTGGATCCGGAAAATCGGTGTTATAGCATCTCAAGCGGTTATCAAGATCAACTACTTATTGGCATATGCCGGTTGTCGGTTGTATGGCTAAGGATAGCGG   500
 L  D  P  E  N  R  C  Y  S  I  S  R  G  Y  Q  D  Q  L  L  L  A  Y  A  G  C  R  L  Y  G  *  G  *  G

TACCACATCGAAATCTACATTCGACTTGTTCACAGATCTTCATGTTGAAGAGCGAAGAGATCTTCGAGTTCCCTTCTGTCGAACACTTAACA       600
 T  T  S  K  S  T  F  D  L  F  T  D  L  L  L  M  L  K  S  E  E  D  L  L  K  F  P  S  V  E  H  L  T

TCAGTTGTTCTCAAGCGAATGTTGGCCAGTGCTCTGATTGCTCGATTCGATGATGTAGTTCAAGAGGAGACGATACGCTGGG                 700
 S  V  V  L  K  R  M  L  A  S  A  L  I  E  R  P  N  T  L  F  V  F  D  D  V  V  Q  E  E  T  I  R  W  A
```

FIG. 19A

```
CTCAAGAACTCCGTCTACGATGTCTTGTAACAACTCGAGACGTGGAAATTTCTCATCAACATGGCCTCATCGTTGCTGAGGTTACATCTCTGGA    800
 Q E L R C L V T T R D V E I S N V A S S T C D F V E V T S L E

AGACGACGAGTGCTACGATATGTTGGAAGCATATGGGATGCCTATTGATCAAAGAGAAGAGATATTAAGTAAGCACTGAAGTTGACTAGT    900
 D D E C Y D M L E A Y G M P I D Q R E E D I L S K T L K L T S

GGAAATCCGGCTGCTTTGATGATGGTGTTCAAATCGTGTTGCGAGCCAAAACTTTCGATAAATGGCACAGTCGAACACGTGGACTGT   1000
 G N P A A L M M V F K S C E P K T F D K M A Q L N N K L E T R G L L

TAGGAATAGAATGCGTGACACCGTATTGCTACACTTCAATCTCAAAGGCCCTTCAGGCGATGTGTTGAAGTTCTGTCTGATGAAGACCGTAATGCTCTGGC   1100
 G I E C V T P Y C Y T S I S K A L Q R C V E V L S D E D R N A L A

ACTCGCTGTCATTATGCCGCCTGAAGTCGATATACCCTGCTTGTTATTCCAGTAAATATGTTCAAGAGGCAGAGTTGTAGAT   1200
 L A V I M P P E V D I P L K I W S L V I P V N I C S N E A E L L D

AATGAAGTTGCAGATCGATTGAAACGGTTGACTAAGCGTGGTGCCTTCTTAGTGGGAAACGAGCACGGTTAACATTCAAATCGACCATATCATTC   1300
 N E V A D R L K R L T K R G A L L S G K R A P A L T F K I D H I I H

ACATTTCTTGAAGCATGTGTTGATACTCAAACTATTGCATCAAACTGCTCGAACAGAACCTTCGTGAGATTAACAACACGTAGCTCCC   1400
 I F L K H V V D T Q T I A C G I A M L E Q N L R E I N N V A S P

AGAACGAAATTTACCCCCACATCATCAGAAATTCAGGGCCATATCTGCAAGTGNATGTATCCGATTTCAGATGAACAAGTCATTCGTCTGAAGATTAC   1500
 E R N L P P H Q K F R R I S A S X M Y P I S D E Q V I R P E D Y

CATAAATTTATGATAATTCACAGCCAGTTCTATGAATCGCTTAAGAAGTTTGTTCTTCCTAAATAGCCATGTATATTCATCCTGTATTTGTCTAGA   1600
 H K F M I H S Q F Y E S L K K F V S S * I A M Y I S S C Y F V *

TTATCTGCATGTCT                                                                                    (SEQIDNo:96)
```

Partial cDNA of Caenorhabditis remanei ced-4 gene2

```
CTGCAGAGATTTTGAGCCGCGTATCCGACATATTTAGAAGCTCTAATGATTTTTCTGAAGACCATACCGACCAATCAAGCCATGACTACTCGATGCGG  100
 A  D  F  E  P  R  Y  P  T  Y  L  E  A  L  M  I  F  S  E  D  H  T  D  Q  I  K  M  T  T  R  C  G

AAGATAGCTGAATTTCTCGGTCATACAGAGAAGCAAGCTTCCGAATTGGCTCCATTAATTGAGTTTTTCAATATAATCATCAACTCATCTATCGGAC  200
 R  I  A  E  F  L  R  S  Y  R  R  Q  A  S  E  L  A  P  L  I  E  F  F  K  Y  N  H  Q  T  H  L  S  D

TTTTCGAGAATTACATAGAAGAAGCGATTCACCACCCGAACTGTTAGACTCGAGACTAATTCCATGTTGAGAGACAAAATTGGATGGAAACTTT  300
 F  F  E  M  Y  I  E  E  A  I  H  H  P  E  L  L  D  S  R  L  I  S  M  F  E  R  Q  K  L  D  R  K  L  L

TATCTGGAAATGTTCCCGACAGATGGATGCGTTCTGTGGTGATTACCACGTTAAACAGTTATTGGAAATTGGAGGCTTTGGGGAATTTAGATTCGTT  400
 S  G  N  V  P  R  Q  M  D  A  F  C  R  D  Y  H  V  K  Q  V  I  G  K  L  E  A  L  G  N  L  D  S  F

TTTTCTTTTTCTTCATGGCCGTGCAGGATGCGGAAATCAGTAATTGCACCTCAAGCTCTGTCTAGATCTCGTGATCATCTTTTCGCAGTTATGACTCA  500
 F  L  F  L  H  G  R  A  G  S  G  K  S  V  I  A  P  Q  A  L  S  R  S  D  H  L  F  A  V  S  Y  D  S

GTTGTGTGGGCTTAAGGACAGCGGTACAACAGCGGAAATCTACATTTGACTGTTACTGTCTTTTGTTGATGTTGAAAAGCGAAGACGACCTCCTCAACT  600
 V  V  W  L  K  D  S  G  T  T  A  K  S  T  F  D  L  F  T  X  L  L  L  M  L  K  S  E  D  D  L  L  N  F

TCCCATCAGTGGAACGCGTAACATCAGTGTACTCAAAAGATGTACTCAACGCTTGATGATAGACCAAACACTCTATTCGTCTTTGACGATGTAGT  700
 P  S  V  E  R  V  T  S  V  V  L  K  R  M  I  V  N  A  L  I  D  R  P  N  T  L  F  V  F  D  D  V  V

TCAAGAGGACGATACCATACGTTGGCTCAAGAACTCCGTCTCAAGAACTACCAGGATGTAGAAATATGCAACGTGCCTCATCAACATGTGAA  800
 Q  E  E  T  I  R  W  A  Q  E  L  R  L  R  C  L  V  T  T  R  D  V  E  I  C  N  V  A  S  S  T  C  E

TTCGTGGAAGTTACATCTCTAGAAGACGATGAATCTAGATGATTGATAGAAGGCTTTAGAATGCCTATGCCAACAGGGAGGAGAGAGAAGATATTCTGA  900
 F  V  E  V  T  S  L  E  D  D  E  C  Y  D  L  I  E  A  F  R  M  P  M  P  T  G  E  R  E  E  D  I  L  R

GGAATACGATCAAGTTAACCAGTGGAAGTTCCAGCTGCTTTGATGATGGTTTCAAATCGTGTGAACCAAGACCTTT    (SEQIDNO:97)
 N  T  I  K  L  T  S  G  S  P  A  A  L  M  M  V  F  K  S  C  E  P  K  T  F
```

FIG. 21

| FIG. 21A |
|----------|
| FIG. 21B |
| FIG. 21C |
| FIG. 21D |

Alignment of degenerins

```
                                 1                                                                              80
Pileup.Msf{Celmec4}                      v  n                s   c     t sk   p
Pileup.Msf{Cbrmec4}                      l  t                r   f   y ti n
Pileup.Msf{Premec4}              ...........................................................................
Pileup.Msf{Celdeg1}              ...........................................................................
Pileup.Msf{Predeg3}              ...........................................................................
Consensus                        MNIS-QT-DD G-YV-FSD-R --Q----FQSE FPVPEQFKTT FVNGKLVTVV SDIMSMQNL KNYQHLRDPS EYMSQVYGDP 81                                                                             160
Pileup.Msf{Celmec4}                      t                                    t         v
Pileup.Msf{Cbrmec4}                      n                                    s         m
Pileup.Msf{Premec4}              ...................................................................  t
Pileup.Msf{Celdeg1}              ...........................................................  m
Pileup.Msf{Predeg3}              ...................................................................  ...m
Consensus                        LAYLQE-TKF VTEREYYEDF GYGECFNS-E SEVQVTPNVY YRAVVV-LFL GCMIMLYLNA QSVLDKYNRN EKIVDIQLKF
```

FIG. 21A

```
                                                                              240
                                                                            e        t
                                                                              r      h
                           161                                              g
                                                                              k
Pileup.Msf(Celmec4)        ............ ............ ............ ............ ............
Pileup.Msf(Cbrmec4)        ............ ............ ............ ............ ............
Pileup.Msf(Premec4)                 d   lkd  a  rk. ...i deirr vatletrkal qtsdvett s pasprirr s skstsf pry
Pileup.Msf(Celdeg1)        ............ ............ ............ ............ ............
Pileup.Msf(Predeg3)        p    a v    a    q cvc...... ............ ............ ............
Consensus                  DTAPFPAITL  CNLNPYKASL ATSVDLVKRT LSAFDGAMGK AGGNK-H--E -EPGFARCLC GSQGSSEQED KD-EKEEE--

241                                                          320
                                kv          e                 n.       w ql       q           t
                                r p         k                 s t      s rr       q           t
Pileup.Msf(Celmec4)        ............ ............ ............ ............ ............
Pileup.Msf(Cbrmec4)        ............ ............ ............ ............ ............
Pileup.Msf(Premec4)        adc........ ............ ......csg  ...sm dt  .v  . kse  t t    ds..    d
Pileup.Msf(Celdeg1)        ............ ............ ............ ............ ............
Pileup.Msf(Predeg3)        ............ ............ ............ ....nlpddq cvpqrn ltk ntsvcmc  d a t  i
Consensus                  ETTT-K-FNI  NG-CCMNGME WK-M-TMSIM RITM-K--LE MNMMEEC-SE R-NSTSPTGF DDRCICAFDR STHGDAWPC- 321                                                          400
                                l    t e     a    n    ..... gh sp.    i a . r     k                f
                                l    t e     a    n    ..... sh sp,    i a . k     k                f
Pileup.Msf(Celmec4)        pkdk    eht   kf d  nv   i e ag....  ..ippvatl l qt np     kesailk l e ygs .. ih  kvv
Pileup.Msf(Cbrmec4)        ............ ............ ............ ............ ............
Pileup.Msf(Premec4)        ............ ............ ............ ............ ............
Pileup.Msf(Celdeg1)        pttv nekt  yh sksnt d dpdrppnits lltepkatp l qs h  mkptedvkc  rs ....... nts  eies
Pileup.Msf(Predeg3)        ............ ............ ............ ............ ............
Consensus                  -NGTWE-T-C  DTCNEH-FCT KD-KTA----  --K--R---C -C-P-S-FCV AYNG-TPPIE IWTYLQGGTP TEDPN-LEAM
```

FIG.21B

```
                              401                                                                            480
Pileup.Msf(Celmec4)           q                           m    t                               t       a  s       n
Pileup.Msf(Cbrmec4)           q                           m    t                               t       v  s       ai
Pileup.Msf(Premec4)           an s                        i    sa iq tm iqhq    q      i    k eit    t  n         qt
Pileup.Msf(Celdeg1)           ..........  .. . . .. ..   .. .....  .. ..... ........  ......   ..  .....    .....
Pileup.Msf(Predeg3)           ad r rg  t  t  t  li  lvapet  rq yld    lr   sed lrr hi men     f ds e
Consensus                     GF-GMTDEVA IVTKAKENI- FAMA-LSMQD RERLSTTKRE LVHKCSFNGK ACDIDADFL- HIDP-FG-CF TFNHNRTV-L 481                                                                            560
Pileup.Msf(Celmec4)                                                                                     rk
Pileup.Msf(Cbrmec4)                                                                                     rk
Pileup.Msf(Premec4)           s                      v                                           tr     r
Pileup.Msf(Celdeg1)           ..........  i v l  t   ssss   a ppt                     v  a   ikkkv q              etk
Pileup.Msf(Predeg3)           kns         ln q       a      v qqe                            ktkv h n e  m..sd
Consensus                     TSIRAGPMYG LRMLV-VNAS DYMPTTEATG VRLTIHDKED -PFPDTFGYS APTGFVSSFG LRL--MSRLP APYGDCVPDG 561                                                                            640
Pileup.Msf(Celmec4)              .. sn  v            k  r       na.     a    k        m                  ....
Pileup.Msf(Cbrmec4)              ..msn  v            k  r       ga.     a pa rs       m                  ....
Pileup.Msf(Premec4)           l tn..  kg r t    t  e  n g       ltnk.s qvf a k     q t  snv
Pileup.Msf(Celdeg1)           vv rn  ag  hp  h    nglid  s      gy.    s fnat t   knigsv d   hitqkmdk
Pileup.Msf(Predeg3)           tfgpeg   a e.h p      n  h d t g  l sdkekp  rnare  t  tnltti   h...lqhd
Consensus                     KTSD--YIY- -YEYS-EGCY RSCFQQLVL- -C-CGDPRFP VPE---RHCD A-DP-AR-CL -AR-NDLGG- HGSF----RC
```

FIG.21C

```
                   641                                                                  720
Pileup.Msf(Celmec4)            r     s              q         n.....        k k
Pileup.Msf(Cbrmec4)            s     s              q         n.....        k k
Pileup.Msf(Premec4)                  ts  en    t  n  s    nd...k.g pdl  e  m
Pileup.Msf(Celdeg1) v k s  ei  he    cs        ga..td     d  d....m es eqy rl  a             a   v           i k
Pileup.Msf(Predeg3) h v ten    eta   a   a     ain n gad cpavyhisnd ska aey rl  t  y                 q           i
Consensus           RCQQPC-QSI Y-VTYSPAKW PSLSL-IQLG SC-----G-T AVECN-HY-E NGAMIEVFYE QLNFEMLTES EAYG-VNLLA 721                                                                                            798
Pileup.Msf(Celmec4)              l c              ta..        s      .......         k k                                 (SEQ ID No: 98)
Pileup.Msf(Cbrmec4)              l c              ta..        s      .......         k k                                 (SEQ ID No: 99)
Pileup.Msf(Premec4)            s   m   t  a  i .. vfn h ni           .......qae eengl*...                                (SEQ ID No: 100)
Pileup.Msf(Celdeg1) h  l  f v ym v cv  v m sl     fksr eek    rqstkr dv .......p d krq tv gr ksdafvsi                    (SEQ ID No: 101)
Pileup.Msf(Predeg3) ni i  f v mf v ev  c i .i     igthsl k    isklIpsqe nnhtafin s    er ktrmk *                         (SEQ ID No: 102)
Consensus           DFGGQLGLWC GISFIT-CEF VFL-LE-I-- YMSAEHNY-L Y----KKKK ------AE- A-KIASGSF-                            (SEQ ID No: 103)
```

FIG.21D

CONSENSUS PEPTIDE OF THE DEGENERINS

1   DiQLKFDtAPFPAiTlCNLNpYKaSL        (SEQIDNo:102)

2   RAGPMYGlrm                        (SEQIDNo:103)

3   PFPDTFGYSAPtGFvSSFG               (SEQIDNo:104)

4   GDPrFP                            (SEQIDNo:105)

5   IEVFYEqLNFE                       (SEQIDNo:106)

CONSENSUS PEPTIDES OF MEC-4

| | | |
|---|---|---|
| 1 | CiCAFDR | (SEQ ID No: 107) |
| 2 | FCVAYN | (SEQ ID No: 108) |
| 3 | DEVAIVTKAKENImFAM | (SEQ ID No: 109) |
| 4 | CSFNGkACDID | (SEQ ID No: 110) |
| 5 | CFTFNHNRT | (SEQ ID No: 111) |
| 6 | SIRAGPMYGLRMLVVN | (SEQ ID No: 112) |
| 7 | SDYMPTTEA | (SEQ ID No: 113) |
| 8 | TIHDKEDPFPDTFGYSAPTGFVSSFGLRL | (SEQ ID No: 114) |
| 9 | YGDCVPDG | (SEQ ID No: 115) |
| 10 | EGCYRsCFQ | (SEQ ID No: 116) |
| 11 | RCRCQQPC | (SEQ ID No: 117) |
| 12 | ENGAMIEVFYEqLNFEmLTESEAYGiVnLLADFGGQLGLW | (SEQ ID No: 118) |

CONSENSUS PEPTIDES OF DEG-3

| | | |
|---|---|---|
| 1 | FGYSAPTGFISSFGLKTK | (SEQ ID No: 119) |
| 2 | CSDTFRP | (SEQ ID No: 120) |
| 3 | EHYSPEGC | (SEQ ID No: 121) |

FIG.22B

FIG. 24B

CONSENSUS PEPTIDES OF CED-4

| EXON | PEPTIDE No. | POS. | L | PEPTIDE | |
|------|-------------|------|----|------------|---|
| 1 | 1 | 4 | 8 | EIECRAL | (SEQ ID No: 122)<br>(SEQ ID No: 123) |
|   | 2 | 20 | 11 | DFEPRDALTYL | (SEQ ID No: 124) |

| | | | | |
|---|---|---|---|---|
| 2 | 3 | 152 | 9 | /SFFLFLHGR | (SEQ ID No: 125) |
| 3 | 4 | 162 | 8 | GSGKSVIA | (SEQ ID No: 126) |
| | 5 | 188 | 8 | VWLKDSGT | (SEQ ID No: 127) |
| | 6 | 200 | 8 | TFDLFTD | (SEQ ID No: 128) |
| 3/4 | 7 | 208 | 7 | LLMLK/SE | (SEQ ID No: 129) |
| 4 | 8 | 220 | 8 | TSVVLKRM/ | (SEQ ID No: 130) |
| 5 | 9 | 242 | 7 | RPNTLFV | (SEQ ID No: 131) |
| | 10 | 250 | 30 | DDVVQEETIRWAQELRLRCLVTTRDVEISN (SEQ ID No: 132) |
| | | | |                     D          I    C (SEQ ID No: 133) |
| 5/6 | 11 | 337 | 16 (11+5) | FKSCEPKTFEK/MAQLN (SEQ ID No: 134) |
| | | | |           D (SEQ ID No: 135) |
| 6 | 12 | 378 | 13 | LQRCVEVLSDEDR (SEQ ID No: 136) |
| | | | |    S |
| 6/7 | 13 | 429 | 20(11+9) | EVADRLKRLTK/RGALLSGKR (SEQ ID No: 137) |
| | | | | (SEQ ID No: 138) |
| 7 | 14 | 463 | 7 | FLKHVVD (SEQ ID No: 139) |

FIG.25B

HOMOLOGY CLONING

STATEMENT AS TO FEDERALLY SPONSORED RESEARCH

This invention was made with support from Small Business Innovation Research Program, National Institute of Health, Institute of General Medical Sciences (Grant No. 1 R43 GM43694-01). Accordingly, the U.S. government has certain rights in the invention.

TECHNICAL FIELD

The present invention relates generally to the manipulation of genetic materials and, more specifically, to the methods for cloning a DNA sequence of interest.

BACKGROUND OF THE INVENTION

Success in identifying a homologue of a prototype gene rests on several factors. Foremost is the rate of sequence divergence, which will determine whether sufficient remnants of a primordial sequence are retained over time to enable cloning and identification of homologous genes over great evolutionary distances.

For example, if sequence similarity between the prototype gene in one organism and its homologue in another organism (which is to be cloned) is relatively high, extending across much of the molecule, then one expects any part of the prototype sequence to provide an adequate probe to detect the homologue.

Further, even if sequence similarity is not high, one may still be able to clone the homologue by subdividing the prototype gene into smaller fragments and test each for its binding to DNA of the target organism. However, only fragments that harbor conserved DNA sequence elements are expected to detect the homologue. An alternative approach to the development of probes depends on the design of degenerate oligonucleotides. This approach requires a consensus protein sequence derived from analysis of multiple homologues of the desired gene. Such analysis appears essential for successful long distance homology cloning.

Long distance homology cloning pertains to periods of time in excess of 600–700 million years. Though the method described in this invention illustrates how to clone across phyla of metazoan organisms, it can be applied to longer time frames or to crossing phyla within other kingdoms, such as plants or fungi. A useful point of reference pertinent to metazoans is when the coelomic lineage, which led to both protostomes and deuterostomes, separated from pseudocoelomates and acoelomic metazoans.

The present invention addresses the central question in long distance homology cloning; namely, what steps are necessary in order to develop probes capable of discriminating homologues from non-homologous DNA?

SUMMARY OF THE INVENTION

In general, the invention, in one aspect, features a method for isolating a structural homologue of a first, higher organism which is structurally homologous with a gene of a second, lower organism, the method comprising the steps of:

a. using two or more oligonucleotides based on two or more regions of the gene to detect hybridization signals or candidate homologues in the genome of a third organism which is positioned phylogenetically between the first organism and the second organism;

b. sequencing the hybridization signals or candidate homologues;

c. selecting structural homologues of the gene based on multiple resemblance in structural characteristics;

d. using additional two or more oligonucleotides based on two or more conserved regions among the structural homologues and the gene to detect hybridization signals in the genome of an additional organism which is phylogenetically positioned between the first organism and the third organism; and e. repeating steps b through d until the gene of the first organism is isolated.

In the above method, the oligonucleotides are either hybridizing probes for detection of hybridization signals or are PCR primers for detection of candidate homologues. When hybridizing probes are used, it is preferred that candidate homologues be selected in step b based on sameness in arrangement or strandedness or both of the probe-binding regions before sequencing the hybridization signals. The term "sameness" here and below refers to a comparison between a probe- or primer-binding region and its corresponding probe or primer. Similarly, the term "resemblance" as recited in step c and in other places below refers to a comparison between the structural homologue and the gene. Note that the length of the oligonucleotides herein (either probes or primers) ranges from 15 nucleotides to the full length of the gene or its structural homologues (either cDNAs or genomic sequences).

Further, either primers or probes are used, it is preferred that in step b the probe- or primer-binding regions or their surrounding regions be first sequenced and putative homologues be selected based on presence of an open reading frame in the sequenced probe- or primer-binding regions alone or together with the sequenced surrounding regions. Other criteria for selecting putative homologues include presence of a splice site(s) in the vicinity of the probe- or primer-binding regions, and sequence similarity between the probe- or primer-binding regions and the probes or primers. Clearly, one can also select a putative homologue further based on sequence similarity beyond the probe- or primer-binding regions. [The term "similarity" here and below again refers to a comparison between the surrounding regions of the probe- or primer-binding sites and their counterparts in the gene.] Also, it is desirable that only the hybridization signals that are detected by at least two of the two or more oligonucleotides are sequenced. Alternatively, one can prioritize the hybridization signals to be sequenced by first examining the presence of dispersed sequence similarity with the oligonucleotides based on restriction/hybridization analysis. See Example 3 below for a detailed description of this analysis.

In the above-described method, the oligonucleotides are used to screen a DNA library, e.g., a genomic library or a cDNA library. Further, the oligonucleotides can also be applied to genomic DNA analyzed on a Southern blot in a manner well known in the art. Also see working examples set forth below. Note that one can also use the oligonucleotides as a primer pair in a PCR amplification with RNA (e.g., total RNA or mRNA), reverse transcribed RNA (i.e., cDNA), or DNA (e.g., ds-cDNA or genomic DNA which is cloned/fractionated or otherwise) being the template.

The oligonucleotides used in this method are preferably degenerate. Further, the oligonucleotides used in step e can be based on intra-species conserved regions among members in a gene family.

The terms "lower organism" and "higher organisms" used herein are referred to according to the following scheme.

Lower organisms are represented by the prototype organism, that is the organism from which the first gene sequence of interest is isolated and characterized. Organisms are considered progressively higher as one proceeds towards the human lineage, with human considered the highest organism. For a detailed discussion of the organisms selected based on their phylogenetic relationships, see Selection of Organisms below in "Description of the Preferred Embodiments".

In this method, selection of the third organism, the additional organism, or both can be based on the rate of change for a protein during evolution (e.g., see FIG. 2). Note that both in this method and in the methods described below the additional organism is also the first organism at the last cloning cycle. The term "conserved regions" recited in step d of this method (as well as mentioned below) refer to the conservation of peptide residues among the organisms during evolution.

The first organism, can be a deuterostome, a protostome, or a vertebrate (such as a mammal, which can be human). The second organism, on the other hand, can be a nematode, such as *Caenorhabditis elegans, Caenorhabditis remanei, Caenorhabditis briggsae, Panagrellus redivivus, Ascaris suum, Bruggia malayi, Haemonchus contortus,* or *Rhabditis maupasi*.

The gene can be a cell death gene, such as ced-1, ced-2, ced-3, ced-4, ced-5, ced-6, ced-7, ced-8, ced-9, ced-10, mec-4, mec-6, deg-1, deg-3, egl-1, nuc-1, lin-24, or lin-33. For a review of the above-listed cell death genes, see Horvitz et al. In *New Biological Approaches to Neurological Disorders: Pathogenesis and Treatment,* Dahlem Konferenzen, Berlin, Aug. 5–10, 1990.

The invention, in another aspect, features a method for identifying a structural homologue in a first organism which is structurally homologous with a gene first identified in a second organism of a non-vertebrate phylum, the method comprising the steps of:

a. using two or more probes based on nucleotide sequences of the gene to detect hybridization signals in the genome of a third organism which is positioned phylogenetically between the first organism and the second organism;

b. cloning the hybridization signals that are detected by at least two of the two or more probes, determining arrangement or strandedness of probe-binding regions in the cloned hybridization signals, and selecting candidate homologues from the hybridization signals based on sameness in arrangement or strandedness of the probe-binding regions;

c. sequencing the probe-binding regions in the candidate homologues and selecting putative homologues from the candidate homologues based on presence of an open reading frame in the sequenced probe-binding regions;

d. sequencing the putative homologues and selecting structural homologues from the putative homologues based on multiple resemblance in structural characteristics;

e. using additional two or more probes based on two or more conserved regions among the structural homologues and the gene to detect hybridization signals in the genome of an additional organism which is positioned phylogenetically between the first organisms and the additional organism; and f. repeating steps b through e until the structural homologue of the first organism is identified.

The term "non-vertebrate phylum" refers to all five eukaryotic kingdoms. The metazoans are used herein to illustrate this invention. Examples of metazoan non-vertebrate phyla include: nematodes of the pseudocoelomates; arthropods, molluscs and annelids of the protostome branch; echinoderms, tunicates and hemichordates of the deuterstome line leading to vertebrates, and; earlier multicellular forms including, but not limited to sponges and coelenterates.

Preferably, only the hybridization signals that show dispersed sequence similarity with the probes based on restriction/hybridization analysis are cloned in step b (see above). It is also preferable that regions surrounding the probe-binding regions are also sequenced in step c and putative homologues are selected based on presence of an open reading frame in both the sequenced probe-binding regions and the regions surrounding them.

Furthermore, the candidate homologues preferably are selected based on sameness in both arrangement and strandedness of the probe-binding regions. The putative homologues, on the other hand, can be selected further based on presence of a splice site or sequence similarity between the probe-binding regions and the probes. An additional criterium for selecting of a putative homologue is similarity in sequences beyond the probe-binding regions.

The probes, preferably degenerate, can be used to screen a proper DNA library or applied to genomic DNA analyzed on a Southern blot as described above. Similarly, the probes used in step e can be further based on intra-species conserved regions among members in a gene family.

Selection of the third organism, the additional organism, or both can be based on the rate of change for a protein during evolution. For candidates for the first organism and the second organism, see discussion above. The gene can be a cell death gene, e.g., that of a nematode (also see above for a list of preferred nematodes).

A third feature of the invention is a method for identifying a structural homologue in a first organism which is structurally homologous with a gene first identified in a second organism of a non-vertebrate phylum, the method comprising the steps of:

a. using a pair of primers based on a first and a second nucleotide sequences of the gene to conduct PCR assays on mRNA or DNA prepared from a third organism which is positioned phylogenetically between the first organism and the second organism;

b. selecting candidate homologues from the PCR products based on presence of an internal nucleotide sequence corresponding to a third nucleotide sequence of the gene which is disposed between the first and second nucleotide sequences of the gene;

c. sequencing primer-binding regions in the candidate homologues and selecting putative homologues from the candidate homologues based on presence of an open reading frame in the sequenced primer-binding regions;

d. sequencing the putative homologues and selecting structural homologues from the putative homologues based on multiple resemblance in structural characteristics;

e. using an additional pair of primers based on conserved regions among the structural homologues and the gene to conduct PCR assays on mRNA or DNA prepared from an additional organism which is positioned phylogenetically between the first organism and the additional organisms; and f. repeating steps b through e until a structural homologue of the first organism is identified.

In step c of this method, regions surrounding the primer-binding regions are also sequenced and putative homologues are selected based on presence of an open reading frame in both the sequenced primer-binding regions and the regions surrounding them. Preferably, the putative homologues are selected further based on presence of a splice site. It is particularly preferred that the putative homologues be selected further based on similarity between the primer-binding regions and the primers or, in addition, also based on similarity in sequences beyond the primer-binding regions.

The primers can be applied to RNA, reverse transcribed RNA, or DNA in a PCR amplification. Preferably, the primers are degenerate. Also, in step e the primers are further based on intra-species conserved regions among members in a gene family. The selection of the third organism, the additional organism, or both can be based on the rate of change for a protein during evolution. See discussion above for details.

The candidate genes based on which a structural homologue is to be cloned and the candidate for the first and second organisms are also discussed above and will not be repeated.

Other important terms recited above, such as "hybridization signal", "candidate homologue", "putative homologue", "structural homologues" or "structural characteristics", are defined in "Description of the Preferred Embodiments".

The primary advantage of the method of long distance homology cloning disclosed in this invention is that it transforms the process which might ordinarily require serendipity or a great deal of prior knowledge to one where progression from lower organism to higher organism can proceed in a timely and efficient manner. Investigations on model genetic organisms, which otherwise might be classified as lower organisms, have often revealed very interesting and important genes.

Identification of genes by loss of function mutation can support the notion that genes perform essential functions for specific biological processes, and they are not rarely correlated with the process. For example, mutations in genes that result in a null phenotype, which permits cells that normally die to survive intend are killer genes—they cause cells to die. In contrast, the correlation of particular proteins, such as β-amyloid plaques, in Alzheimers disease does not clarify the role of β-amyloid in this disease.

The vertebrate (e.g., human) homologues of these genes might not be identified by routine cloning methods such as protein purification or through bioassay protocols. Furthermore, application of genetic approaches, which identify such key genes via mutation often cannot be applied to mammalian nor to human systems. Therefore, long distance homology cloning provides the only reasonable path to obtain the human equivalent of these important genes. Application of the method described herein will achieve success as long as sufficient homology is retained between the lower prototype organism sequence and the higher organism sequence.

Other features and advantages of the invention will be apparent from the following description of the preferred embodiments, and from the claims.

BRIEF DESCRIPTION OF THE DRAWING

The drawings are first described.

FIG. 4 is the coding strand of the DNA sequence and the deduced amino acid sequence of the ced-4 cDNA of *C. elegans*.

FIG. 8 is the coding strand of the DNA sequence and the deduced amino acid sequence of the coding regions of the ced-4 cDNA of *C. briggsae*.

FIG. 10 is a list of DNA oligonucleotides used in obtaining the ced-4 homologues in the disclosed invention.

FIG. 11 is the coding strand of the DNA sequence and the deduced amino acid sequence of a partial mec-4 cDNA of *C. elegans*.

FIG. 13 is a four-base restriction enzyme analysis of three hybridizing clones.

FIG. 14 is a list of degenerate PCR primers and degenerate oligonucleotide probes used in isolating the degenerin homologues disclosed in this invention.

FIG. 15 is a summary of southern blotting experiments used to refine degenerate oligonucleotide probes that include eight overlapping sets of degenerate 20-mers which represent a stretch of 11 amino acids.

FIG. 16 is the coding strand of the DNA sequence and the deduced amino acid sequence in the coding regions of PCR products of three deg-3 genes: from *P. redivivus* (top panel); *Ascaris suum* (middle panel); and *C. elegans* (bottom panel).

FIG. 17 is the coding strand of the DNA sequence and the deduced amino acid sequence in the coding regions of the deg-3 gene of *P. redivivus*.

FIG. 18 is a portion of the coding strand of the DNA sequence and the deduced amino acid sequence in the coding regions of the mec-4 gene of *A. suum*.

FIG. 19 is the coding strand of the DNA sequence and the deduced amino acid sequence of a partial cDNA of the *Caenorhabditis remanei* ced-4 gene 1.

FIG. 20 is the coding strand of the DNA sequence and the deduced amino acid sequence of a partial cDNA of the *C. remanel* ced-4 gene 2.

FIG. 21 is an alignment of deduced amino acid sequences of degenerins, which include mec-4 of *C. elegans* (CELMEC4), mec-4 of *C. briggsae* (CBRMEC4), mec-4 of *P. redivivus* (PREMEC4), deg-1 of *C. elegans* (CELDEG1), and deg-3 of *P. redivivus* (PREDEG3). The deduced amino acid sequences were aligned using the program PIIEUP (GCG, University of Wisconsin). A concensus position is shown in uppercase when at least three of the sequences are in agreement. When residues do not agree with the consensus, they are shown in lowercase.

FIG. 24 is an alignment of deduced amino acid sequences of ced-4 from C. elegans, C. briggsae, C. remanei gene 1, and C. remanei gene 2. The deduced amino acid sequences were aligned and the symbols for consensus and non-consensus positions are shown in the same manners as described in the legend of FIG. 21 above.

DESCRIPTION OF THE PREFERRED EMBODIMENTS

General Cloning Procedures

We have developed a homology cloning method which involves a multi-step, iterative strategy designed to identify DNA sequences that code for evolutionary conserved amino acid sequences. The fundamental premise underlying our approach is that natural selection constrains the divergence of protein structure in order to preserve functional domains. As a consequence, some remnants of primordial sequence are conserved through evolution, while other sequences are not. Sequence conservation provides a molecular means through which to identify and isolate, from one species, a gene that is homologous to a gene in another species.

Figure 1:
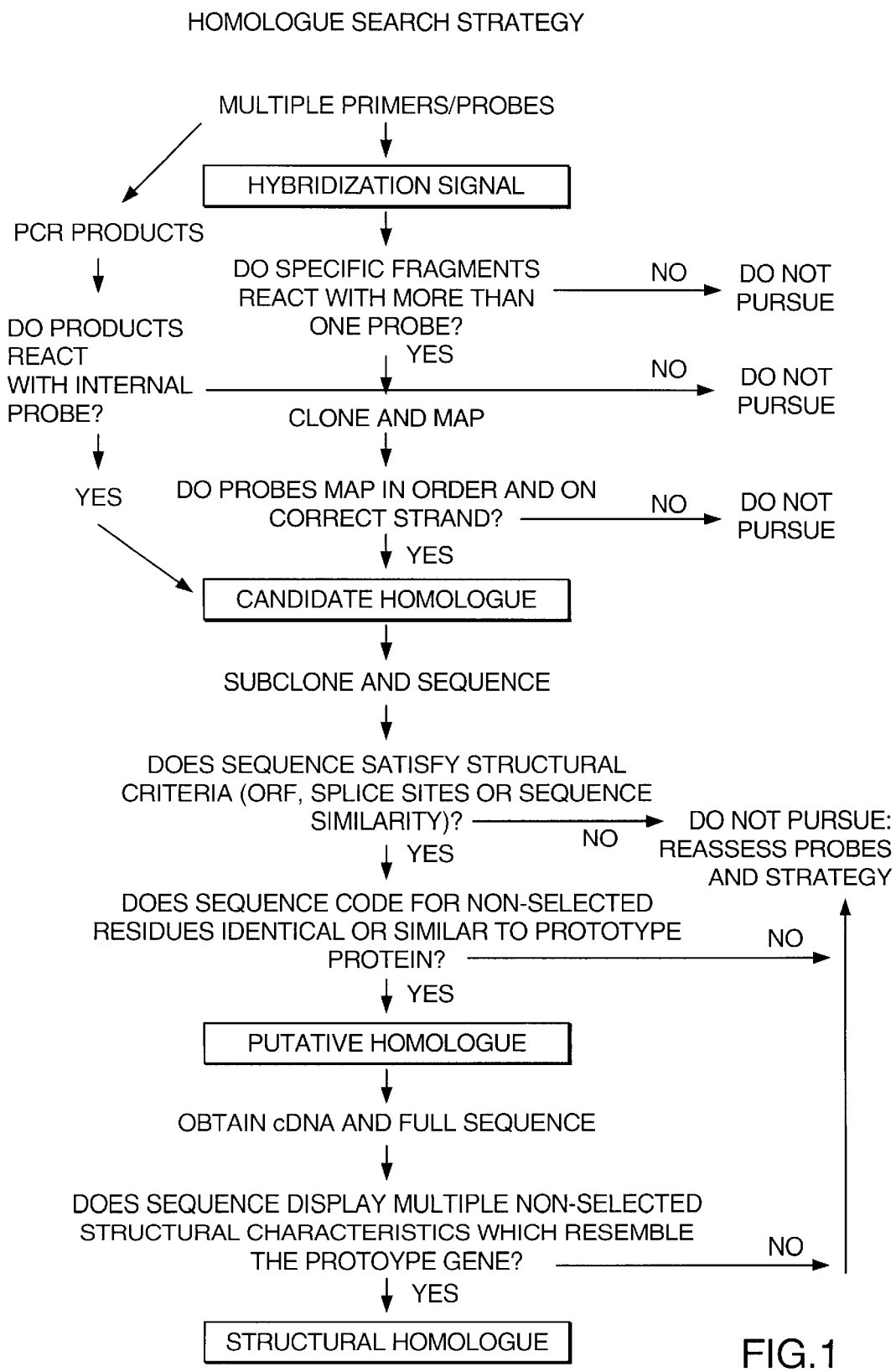
FIG. 1 is a diagram of a homology cloning method, which represents a preferred embodiment of this invention.

For illustration purposes, a diagram of cloning procedures representing one of the approaches of this invention to cloning homologues is shown in FIG. 1. In describing the strategies we use to isolate in a species the homologue of a gene first cloned in another species (i.e., a "prototype gene" in a "prototype organism"), DNA sequences identified during the homology cloning process are placed into one of four categories using the following definitions. Note that all of the four categories are boxed in FIG. 1.

Hybridization Signal

A DNA sequence in the genome of an organism detected by a probe over background noise is called "hybridization signal". Thus, the term "hybridization signal" refers not only to a detected signal (e.g., a radioactive signal when the probe is labeled with $^{32}P$), but also to the DNA sequence whose existence is indicated by detection of the signal.

The detection of a hybridization signal marks the beginning of our analysis, in which two or more probes derived from the prototype gene are used.

Candidate Homologue

Only a fraction of the hybridization signals—those which satisfy specific standards, e.g. binding of at least two probes—are cloned. A candidate homologue is such a clone (i.e., "hybridizing clone") that has been analyzed and shown to meet all of the following well-defined structural criteria:

(1) The probe-binding regions (or "hybridizing regions", i.e., the sequences to which the probes bind to) are arranged in the predicted order, namely, in the same order as that of the nucleotide sequences of the prototype gene based on which the probes are designed; and (2) The probe-binding regions are on the appropriate DNA strand, e.g., on the same strand when the sequences of the prototype gene based on which the probes are designed are also on the same strand.

Putative Homologue

When a candidate homologue whose DNA sequence reveals all of the following features, it is promoted to the status of a putative homologue:

(1) If the candidate homologue is obtained from cDNA sequence, the probe- or primer-binding regions must reside on an open reading frame. Further, if the candidate homologue is obtained from genomic DNA sequence with introns present in it, then the probe-binding site must reside on protein coding sequence (an exon), which is indicated by the presence of an open reading frame and by an adjacent splice site; and, preferably, in addition thereto, (2) Whether the candidate homologue is obtained from genomic DNA sequence or from cDNA, multiple regions of amino acid identity or similarity are present in the deduced peptide sequences corresponding to the borders beyond the hybridizing regions, as compared with the product of the prototype gene.

The term "non-selected residues" in FIG. 1 refer to those which are not represented in the probes.

Structural Homologue

A putative homologue is identified as a structural homologue based on multiple, non-selected structural characteristics that resemble those of the prototype gene. The term "non-selected structural characteristics" refer to features in organization of the gene sequences and in the gene product in addition to those not contained in the probe-binding regions. Non-selected structural characteristics include, but are not limited to, intron/exon boundaries; invariant amino acid residues; position of consensus sites for post-transcriptional modification; relative order of secondary structural elements; recognizable domains, such as membrane spanning segments; and length of the deduced protein sequence.

What is meant by "multiple resemblance" is that the sharing of two or more such features by the putative homologue and the prototype gene.

As shown in FIG. 1 and briefly discussed above, each sequence detected by probes is first classified as a hybridization signal, which is then taken through a series of analyses until it either reaches the status of structural homologue or fails along the way. Passage from one stage to the next usually requires that certain criteria be met. A further goal of the analysis is to prioritize the hybridization signals, clones and candidates. Below is a more detailed description of the general homology cloning procedures.

Upon selection of an organism from which a homologue is to be cloned, a DNA library of that organism is obtained, if available, or established. Alternatively, DNA fragments from the genome of that organism are prepared. As the initial step, multiple (two or more) probes based on the prototype gene are used to screen the DNA library or to select the DNA fragments on Southern blots. Multiple probes are obtained either by subdividing a cDNA clone into smaller fragments or by synthesizing degenerate oligomers representing stretches of conserved amino acids. Probes that detect specific hybridization signals over noise are used to clone (e.g., when Southern blotting is used) and characterize hybridization signals that bind to at least two probes under stringent conditions.

Quite often, far too many hybridization signals are obtained when using highly degenerate oligonucleotide probes to screen genomic libraries. To gain confidence in those signals, one can reduce the probe degeneracy by splitting the oligonucleotide synthesis into two (or more) groups (which have different sets of codons represented at one position in the probe) and use the groups as separate probes. This can be done routinely for degenerate probes that represent serine, leucine and arginine, but in principal can be applied to any backtranslated amino acid other than methionine or tryptophan. In screening libraries four replicate filters are obtained from each plate and divided into two sets of duplicates. The two sets of filters are hybridized independently with the two separate synthetic versions of the degenerate oligonucleotide. If conditions are adjusted correctly, only one of those two probes can bind any specific target DNA sequence and give duplicate signals on the autoradiographs. When that requirement is not met (i.e., if both probes bind), the signal probably represents a spurious, non-specific hybridization event. If increasing the stringency of washes does not segregate the binding of the two probes, then that signal should be dismissed.

When a cDNA probe is used, one can also prioritize the hybridizational signals by conducting a restriction/hybridization experiment to determine whether there is a dispersed or extensive sequence similarity (as compared to the cDNA probe) among the hybridizational signals. For experimental details, see Example 3 below.

Hybridizing clones are analyzed to determine the relative order of the probe-binding regions by physical mapping, the strand on which the probes are binding, or both. If the physical map of the hybridizing clone is consistent with the known map of the prototype gene or the strandedness of the probe-binding regions is the same as that of the corresponding regions of the prototype gene, the hybridization signals become candidate homologue.

Alternatively, polymerase chain reactions ("PCR") are used to amplify specific target sequences. If the amplification products react with an internal probe, then they are treated as candidate homologues. This PCR-based procedure is an important component of the homology cloning strategy described above, since it accelerates substantially the process of refining degenerate oligomer probes.

The criteria of multiple probe reactions for amplification products are that: (1) both sets of primers be present in order to obtain a product; and (2) probes that reside between the primers should hybridize to the product(s) when analyzed on blots. The PCR procedure can be implemented by isolating RNA from proper tissues (i.e., in which the homologue gene is expressed), followed by use of reverse transcriptase and random primers (or oligo dT primers) to synthesize first strand cDNA. Amplifications on these preparations can be carried out in parallel, and only those that lead to the correct length product are pursued.

Note that PCR on genomic DNA templates is the preferred choice when two conserved stretches are present on the same exon and are separated by a significant length of sequence that encodes a recognizable group of conserved amino acids. Two advantages of this procedure are: (1) no assumptions are made about the time or place of expression of the genes; and (2) it is relatively simple to execute and to analyze the results. However, this method does assume that the gene structure is conserved from one organism to another, which may not always be true. Thus, analysis of expressed sequences offers an attractive alternative.

Analysis of expressed sequences using PCR/RNA amplification offers two advantages: (1) the size of an amplified PCR product can be predicted, leading one to pursue a "band of interest" (not merely a major product); and (2) interpretation of coding sequences is more straightforward than genomic DNA. Furthermore, the PCR approach using RNA as template is advantageous over cloning from libraries in that RNA populations not represented by currently available cDNA libraries can be analyzed and that very rare transcripts can be cloned.

Candidate homologues merit partial sequence analysis. First, fragments containing the hybridization signals will be subcloned and relevant portions sequenced. It is preferred that the hybridizing degenerate oligomers be used as sequencing primers (see technical notes below under the heading DNA Sequencing). Candidate homologues with potential exons in which multiple hybridizing regions reside become likely putative homologues. A potential exon is determined by the presence or absence of an open reading frame ("ORF") and splice junctions. Those that fail to satisfy this criterion are cast aside.

Only those potential putative homologues that contain non-selected amino acid codons beyond the probe-binding region are promoted to the status of putative homologues and pursued vigorously. If none of the candidates warrant further attention, one can consolidate information gleaned from the sequence analysis with the homology cloning knowledge and reassess the probes, the conditions for using them, and the overall strategy.

To determine whether a putative homologue is indeed a structural homologue, extensive structural information are needed. To obtained such information, a cDNA library of the organism is screened using unique probes derived from coding sequences within putative homologues, i.e., either exons from genomic DNAs, or coding strands of cDNAs. Clones identified with the unique probes are then sequenced. Genomic DNAs representing all the coding sequences are then isolated by making synthetic probes for various stretches along the sequence. Analysis of the genomic DNAs yields information pertaining to the gene structure, such as the intron/exon boundaries.

Accurate interpretation of the sequence data depends on the amount of prior knowledge of the structure of the prototype gene. Preferably, great value is placed in the sequence of homologues in organisms more closely related to the prototype species and the prototype organism itself. Alignment of the prototype gene products in several such organisms not only define the conserved stretches of amino acid codons, which may lead to useful probes, but also pinpoints individual invariant residues. These landmark residues provide useful criteria for determining whether a putative homologue incorporates more dispersed structural features of the gene product. Other information that pertains to aspects of protein structure include: length of the product; position of consensus sites for post-transcriptional modification; relative order of secondary structural elements; and recognizable domains, such as membrane spanning segments.

A second type of structural information relates to the gene. Because intron positions within a gene often are conserved along very large distances [Gilbert et al. Cell 46:151 (1986)], an identity of intron positions provides a strong argument for homology. Differences of intron positions within a gene, say between the vertebrates and nematodes, or other invertebrates, are explained most readily by loss from one line of descent but not from the other [Doolittle, Nature 272:581 (1978)]. The phenomenon of intron loss apparently occurs more often in organisms that divide rapidly, thus introns remaining in the lower organisms are more likely to be found in the homologues of the higher organisms than the reverse situation. Furthermore, some introns in the higher organisms are likely to be located in positions near or identical to those present in the homologue genes of the lower organisms.

Once a structural homologue has been identified based on analysis of the structural data, the same cloning process can be repeated to clone another structural homologue in a second organism.

However, should one fail to identifying a structural homologue in the organism selected, the appropriate strategy is to take shorter steps in evolutionary distance to other species within the same genus. In other words, discriminating probes must be developed in a step-wise manner. As compared to attempts to take a single giant leap from a prototype gene to the homologue gene of interest, one can obtain a consensus of deduced peptide sequences in the common ancestor of the prototype organism and the target organism by taking several small steps in evolutionary time.

The approach of using degenerate oligonucleotide probes and PCR primers to identify distant homologues requires that some of the invariant sequences be retained in clusters. This iterative procedure can lead to rapid expansion of the sequence database, and ultimately to design of degenerate oligomers based on invariant residues.

Important Considerations

Discussion on several important considerations regarding the general homology cloning procedures described above follows.

Selection of Organisms

In a preferred mode, one practices the invention simultaneously pursuing structural homologues in three higher organisms that progressively represent higher levels of phylogenetic organization. The three higher organisms should include (1) another species from the same genus, usually less than 100 million years diverged from the prototype; (2) a higher organism within the phyla of the lower organism, but which has evolved separately for 200 to 500 million years, perhaps from a different order or class, and (3) some organism containing a small genome in the highest organism phylum. This approach will simultaneously consolidate the basis of probe development and attempt to connect to earlier points in the lineage.

For example, should one begin with C. elegans as the lower prototype organism, it is preferable that the first cycle of homology cloning include C. briggsae, Ascaris suum and Ciona intestinalis. The organism in the same genus provides a meter of the divergence rate of the protein of interest. The distant relative within the phylum, if obtained, provides a measure of residues more resistant to change. The organism outside the phylum, on the other hand, provides a test whether the first cycle of probes or primers are sufficient to obtain the structural homologue in the higher organism.

If one achieves identification of the structural homologue outside of the phylum, then studies on organisms within the lower phylum are no longer necessary. However, when structural homologues are identified only in the first two higher organisms, then comparison of the sequences in those two species with the prototype lower organism is used to establish a consensus sequence. This begins the second cycle of probes or primers, which are then used to identify another structural homologue in an organism as distant as the one most distant from the prototype (i.e., representing the same level of phylogenetic organization) and a second organism in the phylum which is further along towards the higher organism (i.e., representing a higher level of phylogenetic organization).

As an example, should the A. suum and C. briggsae structural homologues both be identified using C. elegans probes, then the consensus of those three sequences is used to refine probes or primers to identify a structural homologue within a species of either the order Strongylida or Spirurida, and a more distant higher nematode, such as one belonging to the class nematamorpha. Again, the small genome non-nematode should be included as well. In such a manner, one can consolidate the existing consensus with three examples of the sequence of interest at the most advanced phylogenetic level obtained in the previous cycle and concurrently strive to connect to earlier points in the lineage represented by the higher organism in the nematomorpha.

In the case when the search for the first distant nematode structural homologue fails, but the search for the structural homologue within the same genus does succeed, then the consensus sequence of those first two examples can be used in a manner parallel to the previous example, with some modifications. For example, if the A. suum structural homologue is not identified, but the C. briggsae is, then the consensus of C. briggsae and C. elegans is used to find another example at the same phylogenetic level to consolidate the consensus sequence (such as C. remanei) and to simultaneously attempt to take two higher, but moderate steps, which are chosen on the basis of the rate of sequence divergence between species in the genus. This choice of species includes a species in the genus of a sub-family such as Pellioditis, as well as one higher organism belonging to a different family or order.

Figure 2:
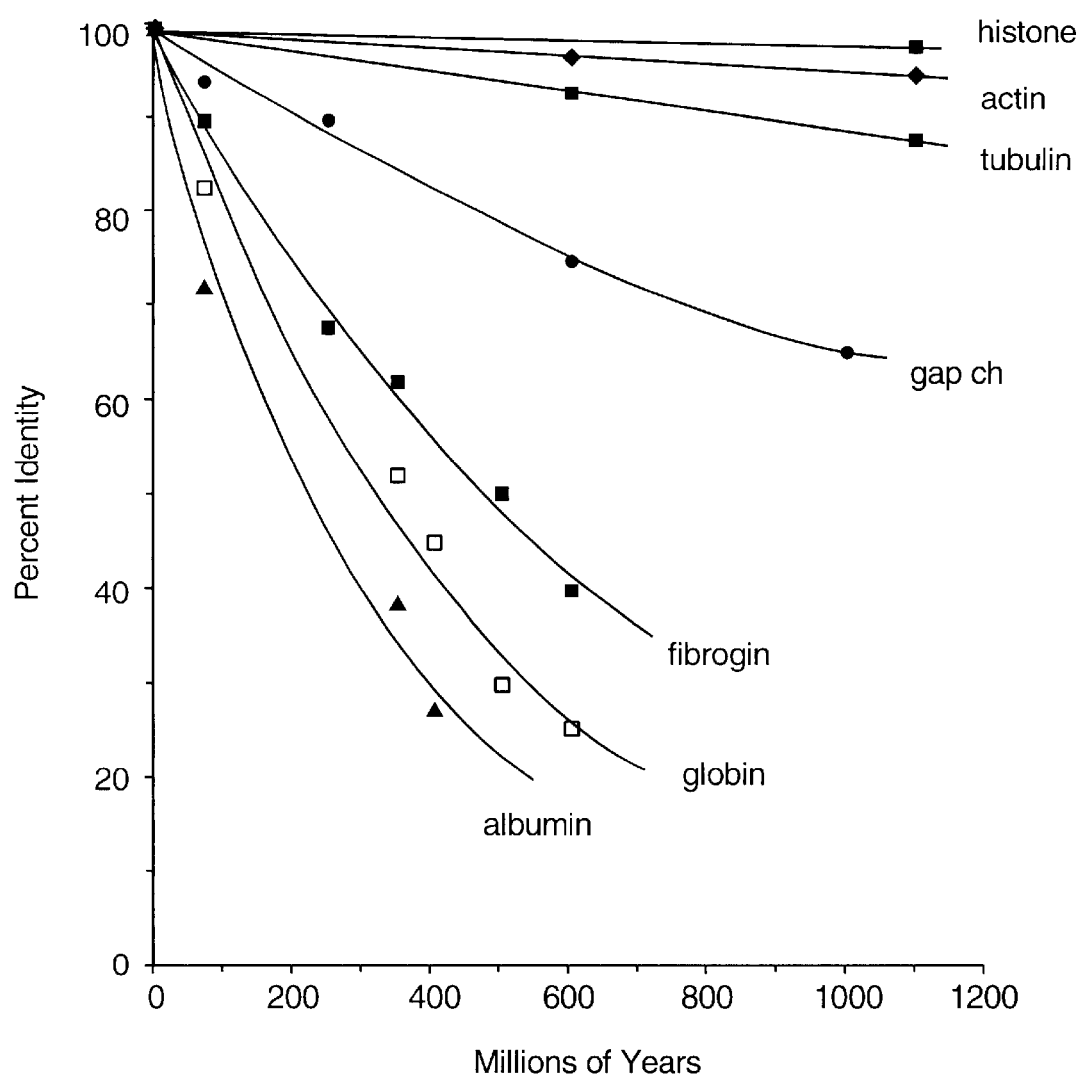
FIG. 2 is a plot showing the amino acid sequence divergence of seven different proteins over the time frame which is significant for this invention. GAP DH refers to glyceraldehyde-3-phosphate-dehydrogenase (R. Doolittle, 1991).

As more organisms are included in each cycle, the database is broadened and one progresses outward in time along the divergence curve that is characteristic of the protein of interest (e.g., see FIG. 2) to progressively refine the regions of sequence conservation and hence, the consensus probes and primers. At the end point, the invariant residues, i.e., those sequences that cannot be changed or substituted for, are defined. These sequences enable the homology cloning of the gene of interest in any phyla where it exists.

Development of More Discriminating Probes

Modifications of the probes and/or adjustments to the hybridizing conditions can take two basic forms. The first strives to make the best possible use of currently available, apparently conserved, amino acid sequence by modifying the composition of sets of degenerate oligomers and the stringency for using them. The second modification is to base the probes on a greater understanding of conserved amino acid residues by analyzing for homologues in more closely related species.

For example, if alignment of the products of the first pair of structural homologues (isolated following the general procedures described above) reveals multiple conserved stretches, then degenerate oligomers can be constructed and used as PCR primers on the DNA templates of other organisms from which a homologue gene is to be cloned. If this first set of degenerate primers leads to bona fide amplification products (which can be confirmed by an independent hybridization to a probe separate from the primers), then these products are cloned and characterized.

This iterative procedure leads to rapid expansion of the sequence database, and ultimately to design of degenerate oligomers based on invariant residues. In cases when the initial set of primers fails to amplify the homologues in other organisms, this first set of amino acids are then dismissed as invariant, since they probably are merely common to the first two examples. Under these circumstances, a third or additional example (i.e., homologous sequences) are identified from genomic DNA fragments, then cloned and characterized. The cycle of sequence determination and alignment, degenerate oligomer design and testing by PCR can be continued until probes capable of selectively detecting any homologue of the prototype gene, including those of human, are constructed.

Pool of Sequences to be Screened

Hybridization signals can be sought from at least three sources: (1) genomic and cDNA libraries; (2) hybridizing DNA fragments purified from preparative gels; and (3) amplification products of polymerase chain reactions.

A critical test of any hybridization signal is to determine if it reacts with multiple probes. For each library screened multiple filters can be prepared from each plate of recombinant phage or cosmids, and each filter hybridized with a specific probe. Recombinants that react with two or more probes corresponding to separate conserved regions of the prototype gene are then subjected to cloning and structural analysis as described above.

In cases when only a single stretch of conserved amino acids is available, a pair of overlapping degenerate oligomers can be designed to be used as probes. Sequences that hybridize to both probes warrant cloning and structural analysis. Similar criteria are to be applied to purified DNA fragments. When fragments react with two or more probes, sublibraries are made, and the hybridization signal cloned.

The approaches that are based on genomic DNA share a caveat which is a consequence of vertebrate gene structure. Large introns may separate the binding sites of probes derived from separate exons and preclude isolation of a single genomic clone, a continuous DNA fragment or a unique amplification product that contains two or more conserved regions. However, the problem can be overcome by looking for genomic DNA candidates in collections of larger DNA segments, such as cosmid or YAC (yeast artificial chromosome) libraries (average size of inserted foreign DNA is about 35 kb and 100 to 500 kb, respectively). Alternatively, sequences that lack introns, e.g., cDNA libraries and RNA, can be screened.

An alternative to isolating hybridization signals and candidate homologues from cDNA libraries is by using the powerful technology of the polymerase chain reaction to screen RNA/cDNA preparations as discussed above.

Cloning of Cell Death Gene Homologues

To demonstrate the implementation of the general homology cloning scheme described above, we set forth below working examples which include detailed experimental procedures on how one can clone homologues of cell death genes which have been identified in the nematode species *Caenorhabditis elegans* from other organisms which have evolved separately from *C. elegans* for increasing lengths of time, beginning with other nematodes and progressing to human.

Figure 3:
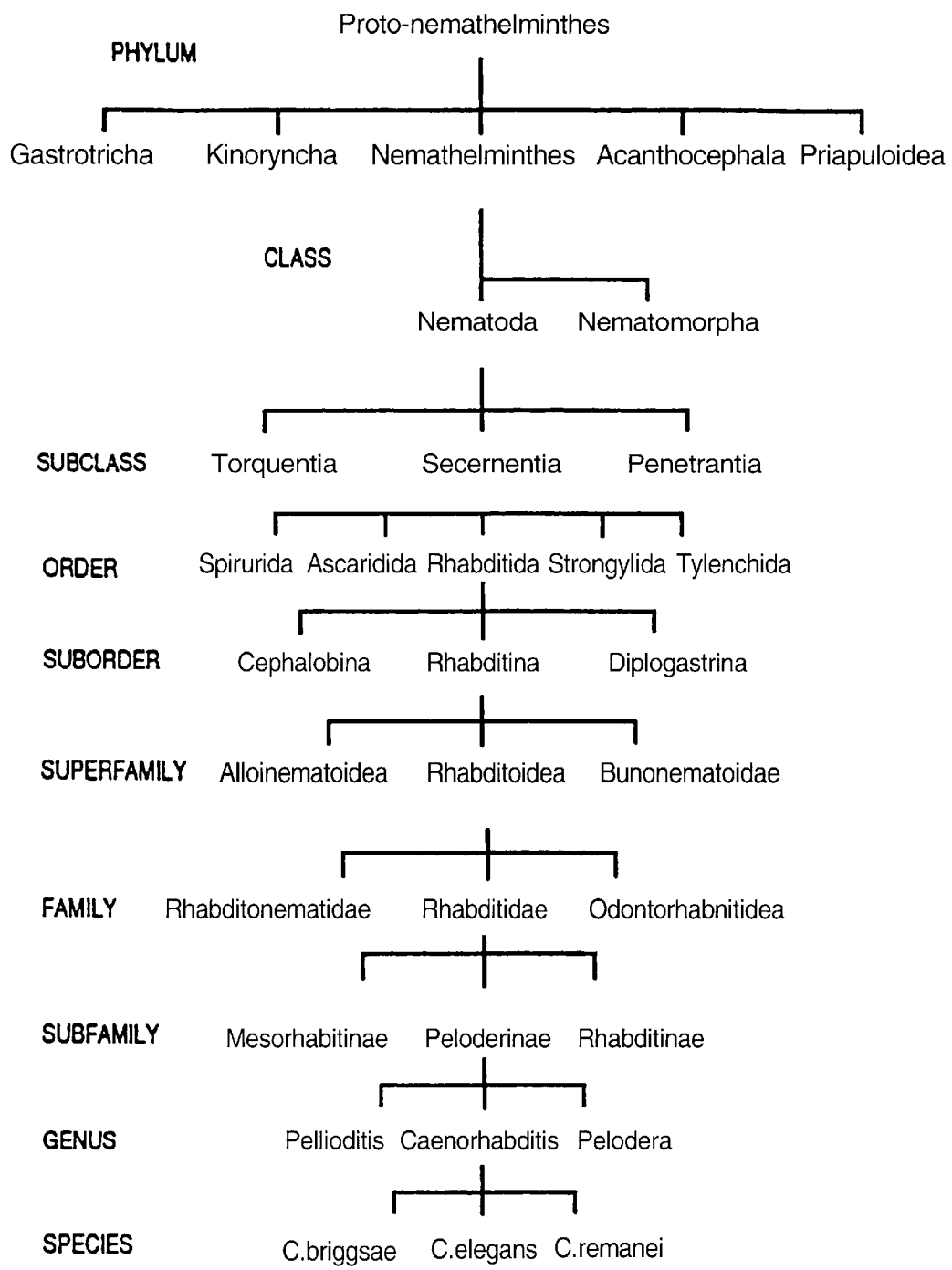
FIG. 3 is a diagram showing the phylogenetic relationships among nematodes where the species *Caenorhabditis elegans* is represented as the lower organism, and the branching pattern shows the path to obtain the consensus of this phylum up to the ancestor of all nematode species, represented by the proto-nemathelminthes. Adopted from I. Andrassy, "Evolution as a Basis for the Systematization of Nematodes", Pitman Publishing, London (1976).

A drawing of the phylogenetic relationship among nematodes is shown in FIG. 3. This drawing is depicted with the species *C. elegans* selected as a starting point for homology cloning, and presents examples of species within other genera, orders and classes that will enable one to develop broadly based consensus peptide sequences. When the consensus peptides of a phylum have reached a broad basis (i.e., sequences including distant relatives within their phylum), then the investigation for homologues outside the phylum (to vertebrates and to coelomic invertebrates) can proceed efficiently.

The experiments conducted in the working examples focused on the identification of homologues in several nematode species and human for three cell death genes of *C. elegans,* namely, ced-4, deg-1 and mec-4. ced-4 is a killer gene whose function is required for all programmed cell deaths in *C. elegans.* See Yuan et al. Devel. Biol. 138:33 (1990). On the other hand, dominant mutations of deg-1 and mec-4, members of a gene family (degenerin gene family), cause the death of a small set of specific nerve cells. See Chalfie et al. Science 243:1027 (1989); Chalfie et al. Nature 345:410 (1990).

Nematode species most appropriate for this task have evolved separately from *C. elegans* long enough to differ by at least 20–30% from the prototype cell death protein sequence of interest, but not so long ago as to preclude cloning using cDNA probes at reduced stringency. We progressively broadened two databases of deduced amino acid sequences (i.e., degenerins and ced-4), and the degenerins database included sequences from two distantly related nematodes. The rate of protein sequence divergence is the key factor which constrains the phylogenetic distance that can be crossed in a single step, and determines how informative such a step will be. See FIG. 2 above. This rate dictates how rapidly the database can be expanded.

Our initial selection of genera and species included a range of near and distant relatives of *C. elegans.* Two closely related species belonging to the genus Caenorhabditis are *C. briggsae* and *C. remanei;* an intermediate relative is *Rhabditis maupasi;* and, two more distantly related nematodes are *Panagrellus redivivus* and *Ascaris suum.* Estimates of the time of divergence from *C. elegans* for members of this group span from 40 million years to 500 million years. We obtained stocks of the five species of nematodes, grew up large scale cultures, prepared DNA and RNA, procured genomic DNA libraries from three of the strains, synthesized and prepared numerous primers and probes, and applied techniques of blotting, PCR, screening, cloning and sequencing.

The technical notes described immediately below relate to the working examples that follow:

Design and Synthesis of Oligonucleotide Probes and Primers

Degenerate DNA oligomer probes were designed by backtranslating the amino acid sequences into nucleotide sequences. Oligomers represented either the coding strand or the non-coding strand of the DNA sequence. When serine, arginine or leucine were included in the oligomer design, then two separate syntheses were prepared to avoid ambiguities. DNA oligomers were synthesized on a Biosearch 8750 4-column DNA synthesizer using β-cyanoethyl chemistry operated at 0.2 μmole scale synthesis. oligomers were cleaved off the column (500 angstrom CpG resins) and deprotected in concentrated ammonium hydroxide for 6–24 hr. at 55–60° C. Deprotected oligomers were dried under vacuum (Speedvac) and purified by electrophoresis in gels of 15% acrylamide (20 mono: 1 bis), 50 mM Tris-borate-edta buffer containing 7 M urea. Full length oligomers were detected in the gels by UV shadowing, then the bands were excised and DNA oligomers eluted into 1.5 mls $H_2O$ for 4–16 hr. with shaking. The eluate was dried, redissolved in 0.1 ml $H_2O$ and absorbance measurements were taken at 260 nm. Concentrations were determined according to the following formula:

$$(A_{260} \text{ units/ml}) \times (60.6/\text{length}) = \mu M$$

All oligomers were adjusted to 50 μM concentration by addition of $H_2O$.

PCR primers were prepared by essentially the same procedures that were used for probes with the following modifications. Linkers of thirteen nucleotides containing restriction sites were included at the 5' ends of the degenerate oligomers for use in cloning into vectors. DNA synthesis was performed at 1 micromole scale using 1,000 angstrom CpG resins and inosine was used at positions where all four nucleotides were incorporated normally into degenerate probes. Purification of PCR primers included an ethanol precipitation following the gel electrophoresis purification.

Library Screening

Genomic libraries were plated on suitable host strains, such as E. coli K12 LE392 on 23×23 cm plates (Nunc) at 150,000 to 200,000 phage plaques per plate. Following an overnight incubation at 37° C., the plates were chilled and replicate filters were prepared according to procedures of Grunstein et al. Proc. Natl. Acad. Sci. USA 72:3961 (1975). Four plaques lifts were prepared from each plate onto uncharged nylon membranes (Pall Biodyne A or MSI Nitropure). The DNA was immobilized onto the membranes by cross-linking under UV light for 5 min. or, by baking at 80° under vacuum for 2 hr.

DNA probes were labeled using T4 polynucleotide kinase (New England Biolabs) with gamma $^{32}$P ATP (New England Nuclear; 6500 Ci/mmol) according to the specifications of the suppliers. Briefly, 50 pmols of degenerate DNA oligomer were incubated in the presence of 600 $\mu$Ci $^{32}$P-ATP and 5 units T4 polynucleotide kinase for 30 min. at 37° C. Reactions were terminated, gel electrophoresis loading buffer was added and then radiolabeled probes were purified by electrophoresis. $^{32}$P labeled probes were excised from gel slices and eluted into water. Alternatively, DNA probes were labeled via PCR amplification by incorporation of $^{32}$P-dATP or $^{32}$P dCTP according to the protocol of Schowalter et al. Anal. Biochem 177:90 (1989). Probes labeled in PCR reactions were purified by desalting on Sephadex G-150 columns.

Prehybridization and hybridization were performed in GMC buffer (0.52M NaPi, 7% SDS, 1% BSA, 1.5 mM EDTA, 0.1 M NaCl, 100 $\mu$g/ml tRNA). Washing was performed in buffer A oligowash (160 ml 1M Na$_2$HPO$_4$, 200 ml 20% SDS, 8.0 ml 0.5 M EDTA, 100 ml 5M NaCl, 3532 ml H$_2$O). Typically, 10 filters (400 sq. centimeters each) representing replicate copies of forty genome equivalents were incubated in 100 ml hybridization solution with 100 pmols of degenerate oligonucleotide probe (128–512 fold degenerate). Hybridization was allowed to occur overnight at 5° C. below the minimum melting temperature calculated for the degenerate probe. The calculation of minimum melting temperature assumes 2° C. for an AT pair and 4° C. for a GC pair.

Filters were washed in repeated changes of oligowash at the hybridization temperatures for approximately four to 5 hr. and finally, in 3.2 M tetramethylammonium chloride, 1% SDS twice for 30 min. at a temperature dependent on the DNA probe length. For 20-mers, the final wash temperature was 60° C. Filters were mounted, then exposed to X-ray film (Kodak XAR5) using intensifying screens (Dupont Cronex Lightening Plus). Usually, a 3- to 5-day film exposure at −80° C. was sufficient to detect duplicate signals in these library screens.

Following our analysis of the results filters could be stripped and reprobed. Filters were stripped by incubating through two successive cycles of 15 min. in a microwave oven at full power in a solution of 1% SDS containing 10 mM EDTA pH 8. Filters were taken through at least three to four cycles of stripping and reprobing with various probes.

Recombinant Phage Isolation, Growth and DNA Preparation

These procedures followed standard protocol as described in Maniatis et al. Recombinant DNA 2.60–2.81, Cold Spring Harbor Laboratory Press, Cold Spring Harbor, N.Y. (1989).

Analysis of Isolated Clones Using DNA Digestion and Southern Blots

Recombinant Phage DNA samples (2 $\mu$g) were digested according to conditions recommended by the restriction endonuclease supplier (New England Biolabs). Following a four hr. incubation at 37°, the reactions products were precipitated in the presence of 0.1 M sodium acetate and three volumes of ethanol. Precipitated DNA was collected by centrifugation, rinsed in 75% ethanol and dried. All resuspended samples were loaded onto agarose gels (typically 1% in TAE buffer; 0.04 M Tris acetate, 0.002 M EDTA). Gel runs were at 1 volt per centimeter from 4 to 20 hrs. Markers included lambda Hind III DNA fragments and/or ØX174HaeIII DNA fragments (New England Biolabs). The gels were stained with 0.5 $\mu$g/ml of ethidium bromide and photographed. For southern blotting, DNA was first depurinated in the gel by treatment with 0.125 N HCl, denatured in 0.5 N NaOH, then blotted from the gel in 20×SSC (3 M sodium chloride, 0.03 M sodium citrate) to uncharged nylon membranes for 6–24 hr. The filters were neutralized in 0.1 M Tris HCl (pH 7.5), 0.15 M sodium chloride, followed by a brief rinse in 50 mM Tris-borate EDTA. For cross linking, the filters were wrapped first in transparent plastic wrap, then the DNA side exposed for 5 min. to an ultraviolet light. Hybridization and washing was performed as described for library screening (see above).

For hybridization analysis to determine whether similar genes exist in other species slight modifications were made. The probe was labeled by PCR amplification reactions as described above, or by nick-translation and hybridizations were done in 80% buffer B (2 g polyvinyl-pyrolidone, 2 g Ficoll-400, 2 g bovine serum albumin, 50 ml 1 M Tris-HCl (pH 7.5), 58 g NaCl, 1 g sodium pyrophosphate, 10 g sodium dodecyl sulfate, 950 ml H$_2$O) containing 10% dextran sulfate. The probes were denatured by boiling for 10 min. then rapidly cooling in ice water. The probe was added to the hybridization buffer at 10$^6$ dpm $^{32}$P per ml and incubated overnight at 60° C. The filters were washed at 60° C. first in buffer B followed by 2×SSC, 0.1% SDS, then in 1×SSC, 0.1% SDS. For high stringency experiments, final washes were done in 0.1×SSC, 1% SDS and the temperature raised to 65° C.

Subcloning

DNA digests (e.g., 5 $\mu$g) were loaded onto 1% agarose gels. Appropriate fragments were then excised from the gels following staining. The DNA was purified by adsorption onto glass beads followed by elution using the protocol described by the supplier (Bio 101). Recovered DNA fragments (100–200 ng) were ligated into linearized dephosphorylated vectors, e.g. pT3T7 (Ambion), which is a derivative of pUC18, using T4 ligase (New England Biolabs). This vector carries the E. coli β lactamase gene; hence, transformants can be selected on plates containing ampicillin. The vector also supplies β-galactosidase complementation to the host cell, therefore non-recombinants (blue) can be detected using isopropylthiogalactoside and Bluogal (Bethesda Research Labs). A portion of the ligation reactions was used to transform E. coli K12 XL1 blue competent cells (Stratagene Catalogue Number: 200236) and then the transformants were selected on LB plates containing 50 micrograms per ml ampicillin. White colonies were selected and plasmid mini preps were prepared for DNA digestion and for DNA sequence analysis. Selected clones were retested to determine if their insert DNA hybridized with the probes.

Determination of Strandedness

The strand on which the probes are binding is also important information in selecting candidate homologues and can be determined by polymerase chain reactions. Saiki, et al. Science 239:4871 (1988).

DNA Sequencing

Double stranded plasmid DNA templates were prepared from 5 ml cultures according to standard protocols. Sequencing was by the dideoxy chain termination method using Sequenase 2.0 and a dideoxynucleotide sequencing kit (US Biochemical) according to the manufacturers protocol [a modification of Sanger et al. Proc. Nat'l Acad. Sci. USA 74:5463 (1977)]. Alternatively, sequencing was done in a DNA thermal cycler (Perkin Elmer, model 4800) using a cycle sequencing kit (New England Biolabs; Bethesda Research Laboratories) and was performed according to manufacturers instructions using a 5'-end labelled primer. Sequence primers were either those supplied with the sequencing kits or were synthesized according to sequence determined from the clones. Sequencing reactions were loaded and resolved on 0.4 mm thick sequencing gels of 6% polyacylamide. Gels were dried and exposed to X-Ray film. Typically, $^{35}S$ was incorporated when standard sequencing kits were used and a $^{32}P$ end labelled primer was used for cycle sequencing reactions. Sequences were read into a DNA sequence editor from the bottom of the gel to the top (5' direction to 3') and data were analyzed using programs supplied by Genetics Computer Group (GCG, University of Wisconsin).

Recently dideoxy sequencing of M13 clones using degenerate oligomers as primers has been reported. Javed et al. Biotechniques 9:28 (1990). To specifically sequence a probe-binding region and vicinity thereof, double stranded sequencing was performed with a 216-fold degenerate oligomer to obtain sequences abutting the probe-binding region and, based on the initial reading, a unique primer was then synthesized and used to sequence back through the probe hybridization site on the opposite strand. Generalized use of this protocol can produce, in an efficient manner, the most essential information for evaluating candidate homologues. As an alternative to this procedure, one can subclone the hybridizing regions onto fragments of 300 bp or less. Then a single round of sequencing from both strands should include all of the data required to analyze the hybridization signal.

RNA Preparation and PCR Amplification

RNA was prepared from frozen nematodes harvested from liquid cultures according to the guanidine neutral-CsCl chloride procedure [Chirgwin et. al. Biochemistry 18:5294 (1979)]. Polyadenylated RNA was selected by oligo-dT cellulose column chromatography [Aviv et al. Proc. Nat'l. Acad. Sci. USA 69:1408 (1972)].

Specific DNA target sequences were amplified beginning with either total RNA or polyadenylated RNA samples that had been converted to cDNA using the Perkin Elmer PCR/ RNA Kit Number N808-0017. First strand reverse transcription reactions used 1 μg template RNA and either primers of oligo dT with restriction enzyme recognition site linkers attached or specific antisense primers determined from cloned sequences with restriction sites attached. To produce the second strand, the primers either were plus strand unique sequences as used in 3' RACE reactions [Frohman, et al., Proc.Nat'l. Acad. Sci. USA 85:8998 (1988)] or were oligo dT primers with restriction sites attached if the second target site had been added by terminal transferase tailing first strand reaction products with dATP (e.g., 5' RACE reactions, see Frohman et al., ibid). Alternatively, as in anchored PCR reactions the second strand primers were degenerate, hence, representing particular peptide sequences. PCR amplifications on DNA templates were performed according to the general procedures set forth in Saiki et al. Science 239:4871 (1988).

The amplification profiles followed the following general scheme: (1) 5 min. soak file at 95° C.; (2) thermal cycle file of 1 min., 95° C.; 1 min. ramp down to an annealing temperature of 45° C., 50° C., or 55° C.; maintain the annealing temperature for 1 min.; ramp up to 72° C. over 1 min.; extend at 72° C. for 1 min. or for 1 min. plus a 10 sec. auto extension; (3) extension cycle at 72° C., 5 min.; and (4) soak file 4° C. for infinite time. Thermal cycle files usually were run for 30 cycles. 16 μl of each 100 μl amplification reaction was analyzed by electrophoresis in 2% Nusiev 1% agarose gels run in TAE buffer at 4 volts per centimeter for three hrs. The gels were stained, then blotted to uncharged nylon membranes which were probed with labeled DNA probes that were internal to the primers.

Specific sets of DNA amplification products could be identified in the blotting experiments and their positions used as a guide to purification and reamplification. When appropriate, the remaining portions of selected samples were loaded onto preparative gels, then following electrophoresis four to five slices of 0.5 mm thickness (bracketing the expected position of the specific product) were taken from the gel. The agarose was crushed, then soaked in 0.5 ml of electrophoresis buffer from 2–16 hrs at 40° C. The crushed agarose was centrifuged for 2 min. and the aqueous phase was transferred to fresh tubes. Reamplification was done on five microliters (roughly 1% of the product) of the eluted material using the same sets of primers and the reaction profiles as in the original reactions. When the reamplification reactions were completed, samples were extracted with chloroform and transferred to fresh tubes. Concentrated restriction enzyme buffers and enzymes were added to the reactions in order to cleave at the restriction sites present in the linkers. The digested PCR products were purified by gel electrophoresis, then subcloned into vectors as described in the subcloning section above. DNA sequencing was done in the manner described as above.

DNA Sequence Analysis

DNA sequences were assembled using a fragment assembly program and the amino acid sequences deduced by the GCG programs GelAssemble, Map and Translate. The deduced protein sequences were searched using Word Search. Analysis was done on a VAX Station 3100 workstation operating under VMS 5.1. The database search was done on SwissProt release number 21 using GCG Version 7.0.

EXAMPLE 1

Direct Screening for Human Homologues Based on CDNA Probes

A. Cloning and Sequencing Human Hybridization Signals, with ced-4 Probes

We began the search for human homologues of the *C. elegans* killer gene ced-4 using a nearly full-length cDNA clone [see FIG. 4, see J. Yuan, Ph.D. Thesis, Harvard University (1989)] to probe genomic DNA blots under a variety of reduced stringency conditions. The blots contained samples from human, *C. elegans* and other nematode species. These experiments showed that the simple assumption of strong and extensive nucleotide sequence similarity was not the case for ced-4.

Figure 5:
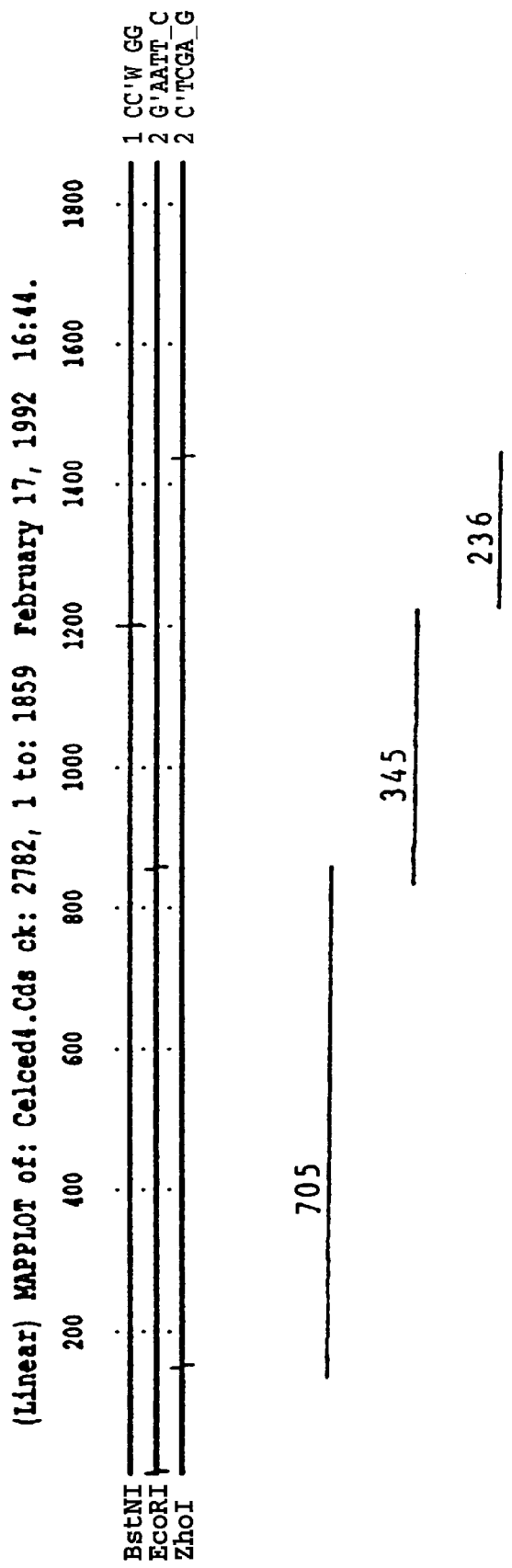
FIG. 5 is a partial physical map of the sequence shown in FIG. 4; the length and position of three DNA probes are shown below the physical map.

We then refined the probe by subdividing the ced-4 cDNA into several smaller fragments (FIG. 5). By reprobing the genomic DNA blots, we found two sub-fragments that detected hybridization signals. Based on these experiments, we used the two smaller probes to screen a human genomic library and four cDNA libraries derived from neuronal tissues (fetal brain, frontal cortex, retina and pituitary). There were no duplicate hybridization signals from any of the cDNA libraries. Thus, all of the signals did not satisfy the criteria required of candidate homologues. However, we detected twenty human genomic hybridization signals and analyzed two clones. The physical map of these clones showed that the two clones overlapped, and the region responsible for the hybridization signal in both clones was sequenced. Shown below are the hybridizing sequence in human DNA (SEQ ID NO:2) and the corresponding sequence in the C. elegans probe (SEQ ID NO:3).

A. Identification of a Homologue of ced-4 in Caenorhabditis briagsae

We searched for homologues of ced-4 in Panagrellus redivivus and Ascaris suum genomic libraries. The libraries were probed with six different subfragments (e.g., see FIGS. 4 and 5) of the cDNA clone over a broad range of hybridization conditions. In contrast to mec-4 (see below), those efforts failed to lead us to a putative homologue, but numerous nonhomologous hybridization signals were detected and several clones were sequenced. For ced-4 this meant pursuing the homologous gene in C. briggsae. Our efforts to clone a ced-4 homologue from a C. briggsae genomic library using a C. elegans cDNA clone were successful.

```
GTTGATGCACAAACTATCGCCAATGGAATCTCAATTCTCGAGCAGCGTCT  (SEQ ID NO:2)
| |||||  | | ||    |||  ||||||||||||   ||||||||||| ||
GATGATG.ATATACGGGAGCCCATGGAATCTCATAGCTCGAGCAGC.ACT  (SEQ ID NO:3)
                           20
```

In assessing the sequence, we noted that although this sequence was part of a lengthy open reading frame (103 amino acids), the region of similarity did not comprise an exon since no consensus junction sequences abutted it. Furthermore, similarity to the sequence of ced-4 does not extend beyond the 24 base stretch shown above, i.e., no non-selected amino acids were detected. Based on these results, it was concluded that this human sequence was not part of a putative homologue of ced-4.

B. Cloning and Sequencing Human Hybridization Signals with deg-1 cDNA Probes

Figure 6A:
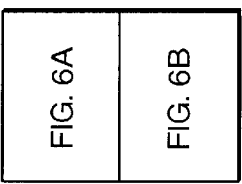
FIG. 6 is the coding strand of the DNA sequence and the deduced amino acid sequence of the partial deg-1 cDNA clone of *C. elegans*.
Figure 6B:
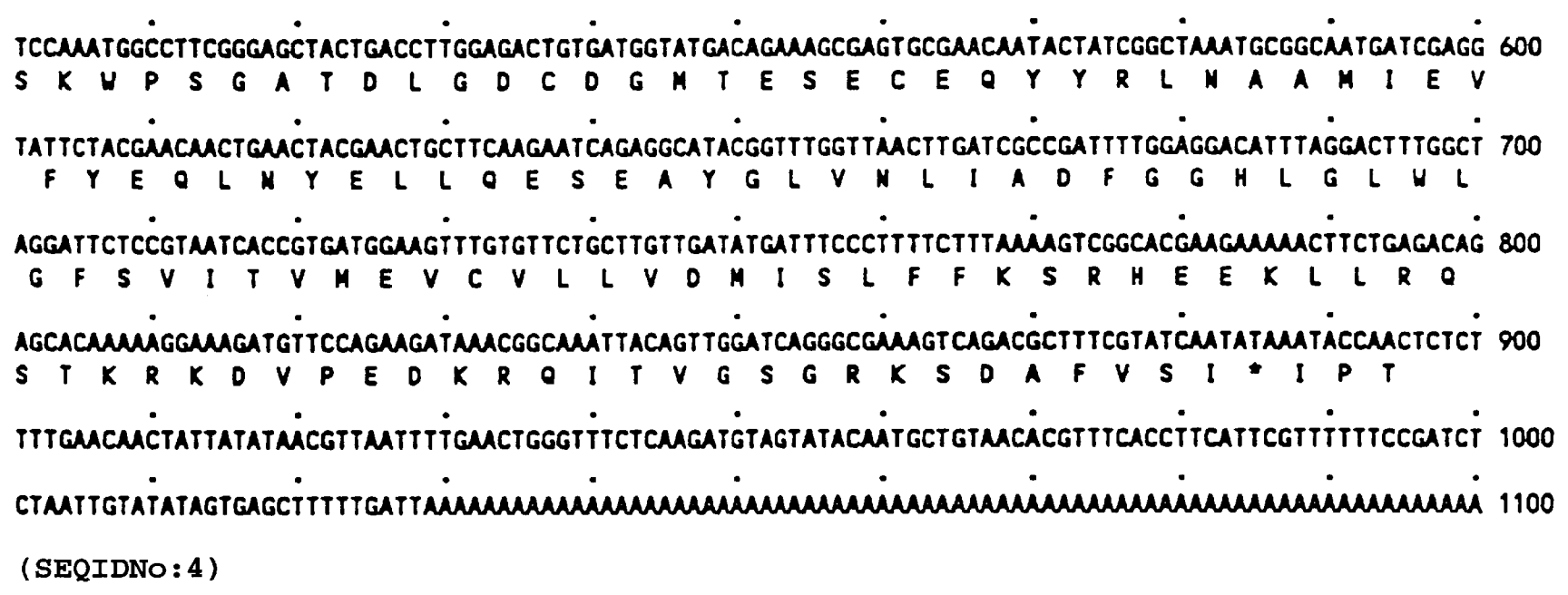

We performed a search for deg-1 homologues on a human genomic library. The equivalent of twenty human genomes were screened at moderate stringency and 177 signals were detected using a deg-1 cDNA fragment [FIG. 6; see Chalfie et al. Nature 345:410 (1990)]). Eleven of the hybridizing DNA sequences were analyzed. From the sequence analysis, it was concluded that the hybridizing regions (1) lacked splice junctions where the similarity decayed; and, most importantly, (2) failed to correspond well with the conserved residues defined by the deg-1/mec-4 comparison [Driscoll et al. Nature 349:588 (1991)]. None of the eleven clones analyzed satisfied the criteria required of putative homologues.

One feature of the contiguous sequence (2700 bp) analyzed in one of the hybridizing clones, H25, is noteworthy and instructive. This sequence contained a 500 base pair stretch of repetitive sequence. The basic unit of this repeat, GGNTGGATGGAT (SEQ ID NO:143), is found in the deg-1 coding sequence at a unique location. We found similar or identical repeated sequences in our analysis of several other human genomic clones isolated with the deg-1 cDNA probe. The two most strongly hybridizing clones had this sequence repeated more than 20 times. It appears likely that a sequence in the coding region of the deg-1 CDNA produced an amplified signal by virtue of its repeated nature in the human genes and that this hybridization signal resulted in the isolation of these clones. Our experience clearly showed the limitations inherent in identifying distant homologues on the basis of hybridization to long nucleic acid probes.

EXAMPLE 2
Identification of Nematode Homologues by Hybridization to cDNA Probes

Homologues in other nematodes were pursued according to the general scheme for identification of homologues.

Figure 7:
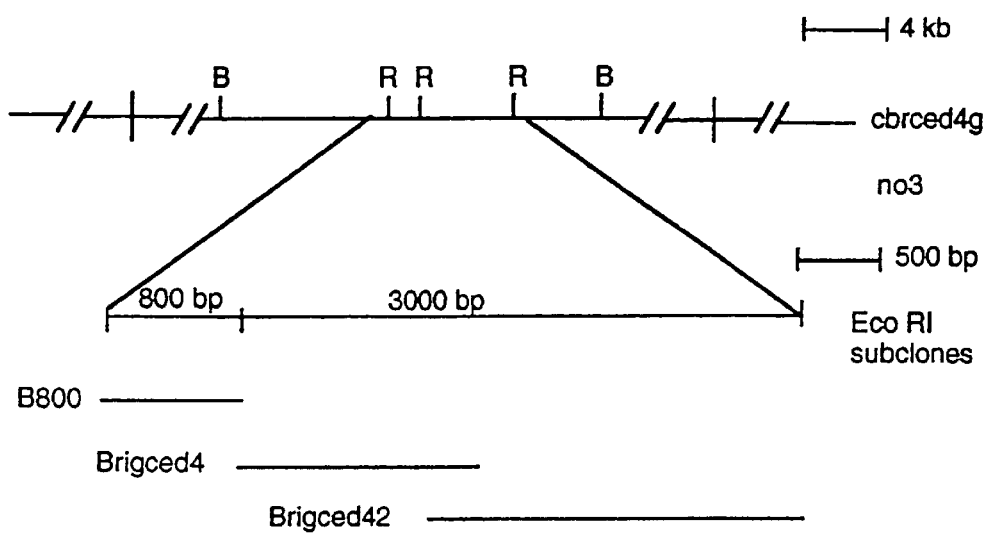
FIG. 7 is a partial physical map of the *Caenorhabditis briggsae* ced-4 genomic DNA clone, subclones and DNA contiguous sequences derived therefrom.

More specifically, the gene encoding C. briggsae ced-4 was isolated from a genomic DNA library in phage charon 5. Approximately 100,000 recombinant plaques were screened with the probes represented in FIG. 5 using conditions of moderate stringency. Twenty three hybridization signals were detected with all three probes; hence, they were considered to be candidate homologues. Four plaques were purified and DNA was prepared from the cloned genomic phage. One clone was pursued to DNA sequencing and it is designated as CBRCED4.GC3. Preliminary physical mapping showed that the probes hybridized a single 9 kb BamHI fragment and EcoRI fragments of 3 kb and 800 bp. These two EcoRI fragments were subcloned into vector pT3T7 and were sequenced. FIG. 7 shows the structure of the genomic phage clone CBRCED4.GC3 in the region containing the sequences encoding C. briggsae ced-4. The 800 bp Eco RI fragment contains the first protein encoding exon of the gene and some upstream sequences. The 3 kb clone contains the remaining seven protein encoding exons and downstream sequences. Three contiguous sequences, i.e., B800, BRIGCED4, and BRIGCED42, represent these areas of DNA sequence as shown in FIG. 7. Their lengths are 863 bp, 1,840 bp, and 1,767 bp, respectively.

Figures 9, 9A:
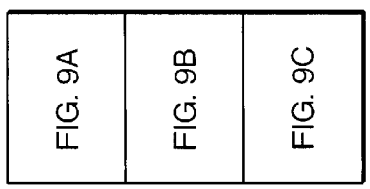
FIG. 9 is the coding strand of the DNA sequence and the deduced amino acid sequence of the ced-4 cDNA of *C. briggsae*.

The contiguous sequences were connected and analyzed for the presence of open reading frames and were compared to ced-4 of C. elegans (FIG. 4) and to the C. briggsae cDNA sequence (described below). This analysis allowed us to construct the gene structure of the ced-4 gene of C. briggsae shown in FIG. 8. Note that the two contiguous sequences of the cloned 3 kb fragment overlap by 371 bp, but there is no overlap with the 863 bp contiguous sequence B800. The B800 sequence was shown to be contiguous through analysis of a cDNA clone with the cDNA sequence shown in FIG. 9.

More specifically, the cDNA sequence of C. briggsae ced-4 was obtained through PCR reactions on reverse transcribed RNA. Using unique primers designed from the gene sequence and several sets of degenerate primers (see FIG. 10), the reverse transcribed RNA was amplified and products were cloned for DNA sequencing. Primers used in these experiments were: 484/485 and 398/399. Based on an analysis of these PCR/RNA products, a partial cDNA of the C. briggsae ced-4 was obtained. Unique DNA sequence primers then were designed for one sided PCR reactions to clone the 3' end.

B. Identification of a Homologue of mec-4 in P. redivivus

Figures 12, 12A:
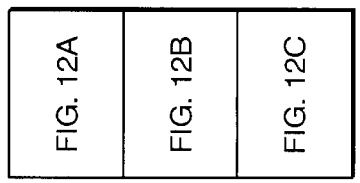
FIG. 12 is the coding strand of the DNA sequence and the deduced amino acid sequence in the coding regions of the mec-4 gene of *Panagrellus redivivus*.

Similarly, we searched for homologues of mec-4 in the distantly related nematode P. redivivus using two subfragments of a cDNA clone to probe a genomic library at reduced stringency. FIG. 11 shows the nucleotide sequence and deduced amino acid sequence of the *C. elegans* mec-4 partial cDNA clone [see Driscoll et al. Nature 349:588 (1991)], which was used as the probe. Results of physical mapping experiments on the lone cloned hybridization signal indicated that it was a candidate homologue and sequence analysis confirmed that we had identified a structural homologue of mec-4. The gene sequence is presented in FIG. 12, where the coding sequence and deduced amino acid sequence were assigned based on comparison with *C. elegans* mec-4 (FIG. 11).

EXAMPLE 3
Recognizing Dispersed Sequence Similarity Through Four-base Restriction Enzyme Analysis Because we had encountered numerous bogus hybridization signals from both human and distant nematode genomic libraries, we include several steps in the strategy that help limit non-productive efforts. A key development for using unique DNA fragment probes was to include several intermediate steps in the analysis to prioritize both hybridization signals and candidates. For example, we assessed whether a hybridization signal arose from extensive and dispersed portions of DNA sequence or, as seen before, it was very restricted. That assessment was based on results of DNA blotting analyses using four-base cutting enzymes. Generally, signals that derive from very small regions of DNA sequence similarity produced a lone hybridizing band for any of the enzymes chosen. However, if multiple bands appeared, then we were encouraged that the similarity was more extensive and gave priority to those hybridizing clones. Mapping hybridizing clones in this manner facilitated the identification of nematode homologues of both ced-4 and mec-4 (see above), which were detected using DNA fragment probes.

FIG. 13 shows a composite result from experiments conducted during the search for ced-4 homologues in *C. briggsae* and human, and for homologues of mec-4 in *P. redivivus*. In these experiments, clones were isolated using radiolabelled fragments of cDNA to probe genomic libraries (EMBL III as the vector) at reduced stringency. 3 µg of phage DNA preparations were digested to completion with selected restriction enzymes and samples were electrophoresed through 3% NuSieve—1% agarose gels (3 hr., 2 V/cm, Tris-acetate-EDTA buffer) and blotted to nylon filters. The filters were hybridized and washed at reduced stringency then exposed to film with an intensifying screen. Hybridizing genomic DNA clones were isolated from: a *C. briggsae* library using a *C. elegans* ced-4 CDNA probe, lanes 1–9; a *P. redivivus* library using a *C. elegans* mec-4 probe, lanes 10–15; a human library using a *C. elegans* ced-4 probe, lanes 16–20. Enzymes used in the experiment were: Alu I (1, 10, 16), BstNI (2,11,17), Dde I (3,12,18), Hae III (4,13), Hinf I (5,14), Msp I (6,15,19), Sau3AI (7,20), Taq I (8), and Xho II (9). Note that in contrast to the nematode clones, the human clone, which showed a lone hybridizing band in all lanes (lanes 16–20), was determined through sequence analysis to be a bogus hybridization signal.

EXAMPLE 4
Identification of Nematode Degenerin Homologues by PCR

As will be shown below, employment of the PCR approach progressively led us to eight nematode homologues, including a new member of the degenerin gene family.

In our initial studies on the PCR-based approach, genomic DNA templates from three nematodes: *C. elegans, C. brigg-sae* and *A. suum* were used. The first set of degenerate primers tested were designed from the two longest stretches of amino acids, PFPDTFGYSAP (SEQ ID NO:140) and CGDPRFPVPE (SEQ ID NO:141) named area I and area II, respectively, which are common to the degenerin gene family members deg-1 and mec-4 from *C. elegans*. Chalfie et al. Nature 345:410 (1990); Driscoll et al. Nature 349:588 (1991).

FIG. 14 lists the degenerate PCR primers and probes used in these studies. Areas I and II are located sixty residues apart in each of these proteins, and there are two introns positioned within that part of the *C. elegans* mec-4 gene. Amplification products were analyzed first by DNA blotting using an internal degenerate oligonucleotide (410, 411) as the probe. A hybridizing product from *C. briggsae* was then subcloned and sequenced, and this sequence was determined to be part of the mec-4 gene of this species. The deduced protein sequence was identical to *C. elegans* over the sixty amino acids analyzed (the nucleotide sequence had diverged 18% from *C. elegans*). Thus, the experiment provided no new information on sequences resistant to change. However, because the reactions done in parallel on *A. suum* DNA did not amplify any specific targets, we reasoned that some residues within areas I or II might be different in that distant nematode. Alternatively, a difference in gene structure, such as a large intron, could have prevented amplification. We tried several combinations of primers from three other conserved areas, but none produced an *A. suum* homologue.

We continued the process of probe/primer refinement by making a concerted effort to test a comprehensive set of probes and primers representing areas I and II. To test all the combinations of degenerate 20-mer primer pairs from area I and area II would have required 64 sets of PCR reactions (plus controls) for each template. To reduce this to a more workable number, a series of DNA blots containing samples from all the nematodes under investigation were analyzed using eight sets of non-biased degenerate 20-mers representing overlapping 7-mers from the eleven amino acids in area I. Conditions were adjusted to allow no mismatching over the 20 bases by washing filters in tetramethylammonium chloride. Wood et al. Proc. Natl. Acad. Sci. USA 82:1585 (1985); Devlin, P. E. et al. DNA 7:499 (1988). We calibrated these blotting experiments using degenerate 20-mers representing invariant sequences in the ubiquitous glycolytic enzyme triosephosphate isomerase [Lolis et al. Biochem. 29:6609 (1990)] until a lone band was detected for each DNA sample.

The results of the experiment (not shown) using all eight probes from area I suggested that the eleven conserved residues were present only in *C. elegans* and *C. briggsae,* and reduced the invariant core of area I at the genomic DNA level to a stretch of eight codons. FIG. 15 shows a schematic summary of these experiments. Similar data were generated for area II, ultimately reducing the number of possible PCR primer combinations to twelve. All twelve combinations (area I: 392, 435, 436; area II: 393, 394, 437, 438, see FIG. 14) of primers were investigated on genomic DNA templates from *P. redivivus, A. suum* and *C. elegans*. A small subset of these reactions led to hybridizing PCR products, which were sequenced. The sequence of these products are presented in FIG. 16.

One *P. redivivus* product (sequence not shown) was determined to be the mec-4 homologue, which we had identified independently by screening a genomic library (see Example 2B above). The other amplified *P. redivivus* sequence represented a novel member of the degenerin family. Subsequently, we discovered this new gene in *A. suum* and in *C. elegans* also and named this new gene deg-3.

Figure 17B:
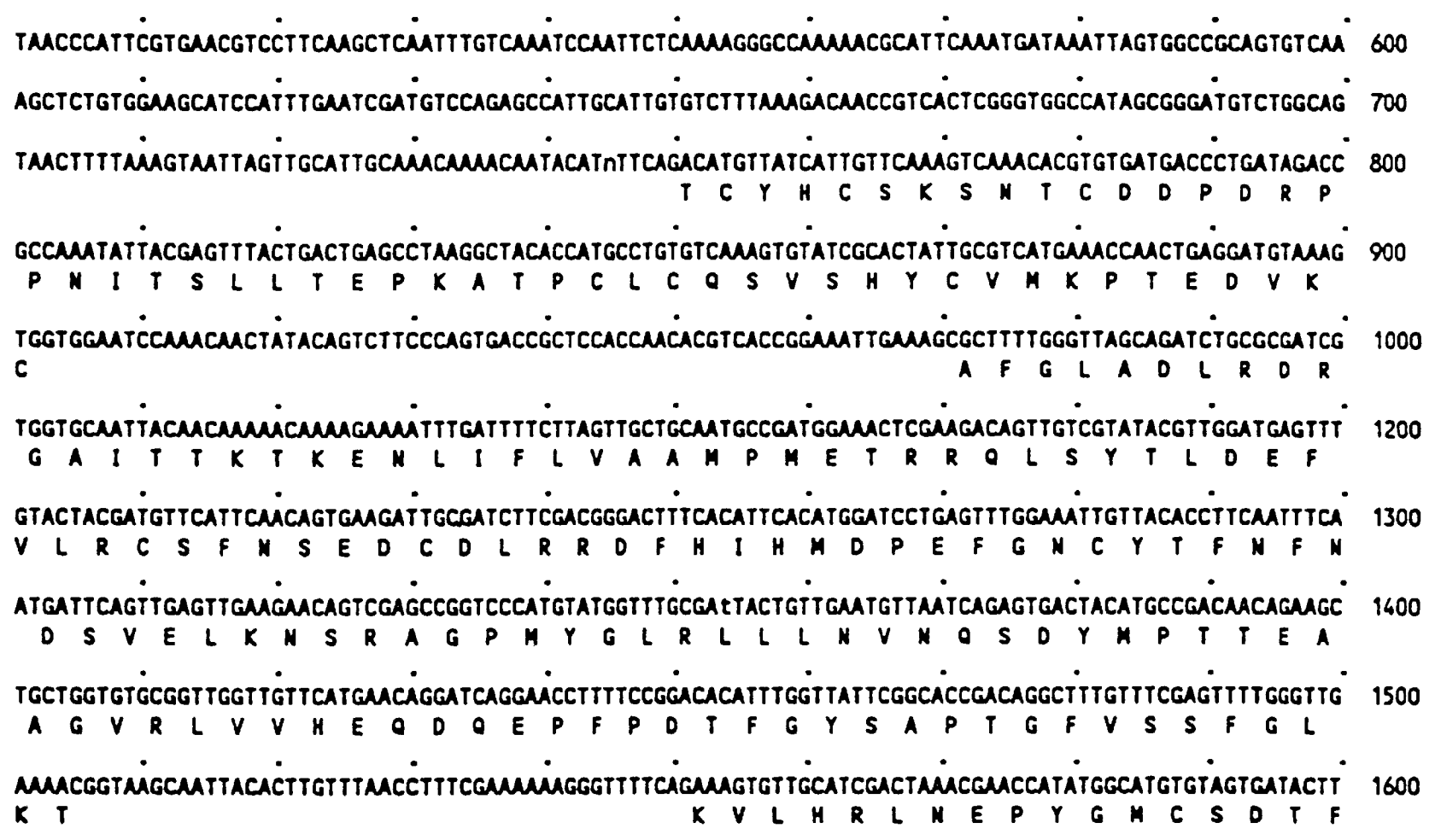

EXAMPLE 5
Development of Refined Primers and Probes by Updating the Degenerin Sequence Database We used the new sequence data generated from Examples 2 and 4 to develop discriminating probes in several ways. From the PCR product sequence data (Example 4) unique primers and probes were designed to confirm the sequences at the primer sites and to extend the information outward. Thus, we extended the sequence of two of the deg-3 genes and of one mec-4 gene. We used inverse PCR [Ochman et al. Genetics 120:621 (1988)] on *A. suum* genomic DNA (primers 594 and 595, FIG. 13) and sequenced portions of the *P. redivivus* genes encoding mec-4 and deg-3 which were isolated from a genomic library (see FIGS. 12 and 17). The resulting data set was combined with previously available sequence [e.g., Driscoll et al. Nature 349:588 (1991)] to produce a revised alignment. This database yielded several newly discovered areas of conserved protein sequences specific to mec-4 and to deg-3. Furthermore, the revised alignment was used to refine the previously recognized areas common to all degenerins, which we refer to as signature sequences.

The new consensus sequences were used to design a second generation of degenerate PCR primers (primers 505–507; see FIG. 14), which, in contrast to the original set of primers (primers 330, 381, 382; see FIG. 14), amplified the mec-4 homologue of *A. suum* (see FIG. 18). That result demonstrated clearly the value of building the consensus sequence in a stepwise fashion. This iterative procedure led to rapid expansion of the sequence database which to be used to design degenerate oligomers based on invariant residues.

EXAMPLE 6
Identification of Nematode ced-4 Homologues by PCR

The *C. briggsae* genomic clone identified using cDNA fragment probes was sequenced (see Example 2). Comparison of the deduced protein sequence to *C. elegans* ced-4 showed an overall identity of 80%, including 22 conserved stretches at least seven amino acids in length. A small subset of these conserved stretches were used to design first generation degenerate PCR primers to amplify homologues in additional nematode species. The analysis was done on both reverse-transcribed RNA [Johnson et al. Nature 346:858 (1990); Veres et al. Science 237:415 (1987)] and on genomic DNA templates from *C. briggsae, C. remanei, Rhabditis maupasi* and *P. redivivis*.

Figure 26:
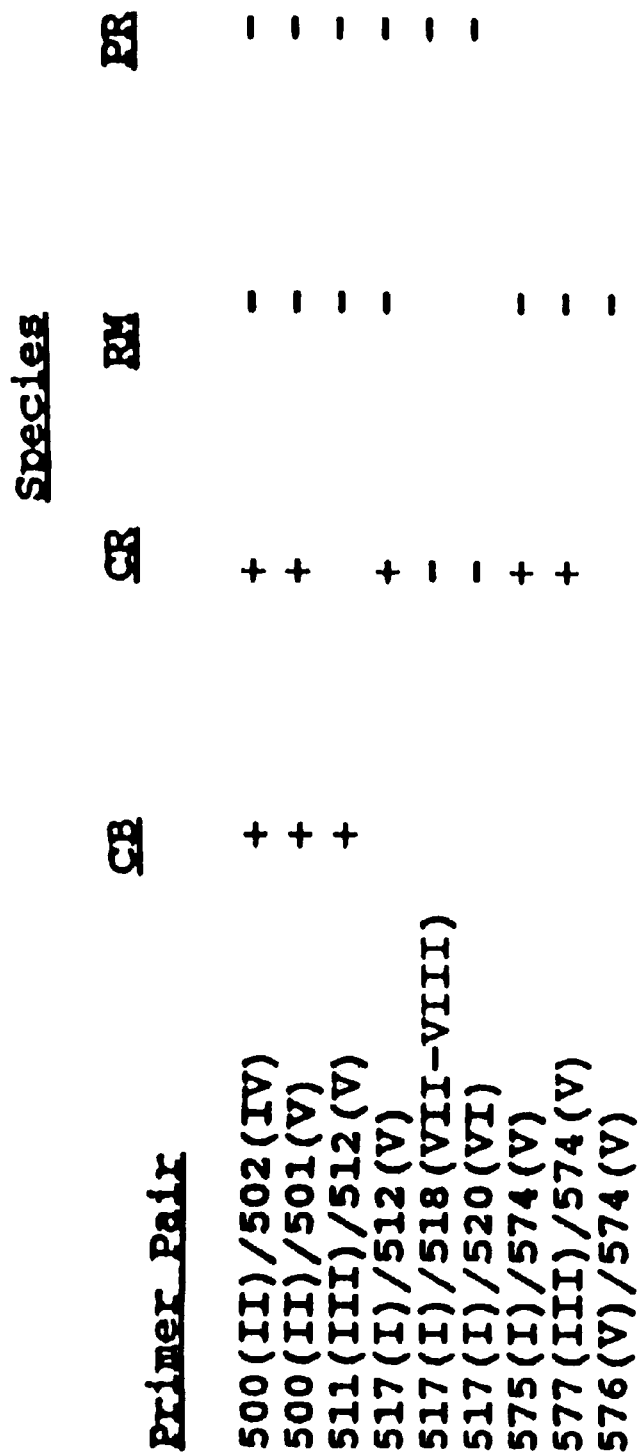
FIG. 26 is a summary of PCR experiments on four nematode cDNA templates using sets of primers designed from the alignment of C. elegans and C. briggsae ced-4, where plus (+) indicates the specific product was produced and minus (−) indicates that such a product was not produced.

Referring to FIG. 26, PCR amplifications were performed on reverse transcribed RNA from *C. briggsae* (CB), *C. remanei* (CR), *R. maupasi* (RM) and *P. redivivus* (PR) using the primer pairs shown. A plus (+) indicates that a correct target sequence was amplified and a minus (−) indicates that the experiment failed to produce such a product. A list of primer sequences are shown in FIG. 10 above.

Two distinct *C. remanei* ced-4 RNA transcripts were identified using this approach (see FIGS. 19 and 20). None of the combinations of PCR primers tested in these experiments produced a ced-4 homologue outside of the genus Caenorhabditis, showing that not all of the sequences that are common to two proteins will be retained in all homologues. Obviously, further refinement is necessary.

EXAMPLE 7
Comparison of Deduced Nematode Degenerin Sequences

We identified eight *C. elegans* degenerins homologues in related nematodes and produced a database that includes ten deduced degenerin sequences. This information provided a broad basis for development of consensus probes, some of which are used to discriminate human homologues from non-homologous hybridization signals.

Figures 22, 22A:
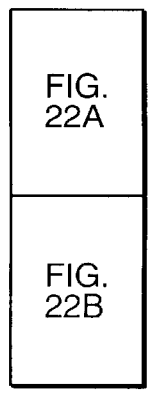
FIG. 22 is a list of three sets of consensus peptides from degenerin sequences. The three panels show the five signature consensus peptides, twelve consensus peptides of mec-4, and three consensus peptides of deg-3, respectively. Uppercase characters represent sequences present in all mec-4 deduced amino acid sequences.

Two of the mec-4 sequences were completed [Driscoll et al. Nature 349:588 (1991); ibid, unpublished]. Data on *P. redivivus* overlap those two sequences by nearly 600 amino acids. Alignment of the three longest mec-4 sequences with deg-3 from *P. redivivus* and deg-1 of *C. elegans* led to a partial consensus sequence (FIG. 22). A consensus position was designated only when three or more sequences agree. In analyzing the consensus, we found several conserved stretches (window=6) that could be used to design degenerate probes and PCR primers (see FIG. 21). We considered six consensus amino acids to be a minimum length for this purpose. (Shorter degenerate oligonucleotide probes and primers may not be specific enough to identify homologues in complex non-nematode genomes.)

Figure 23:
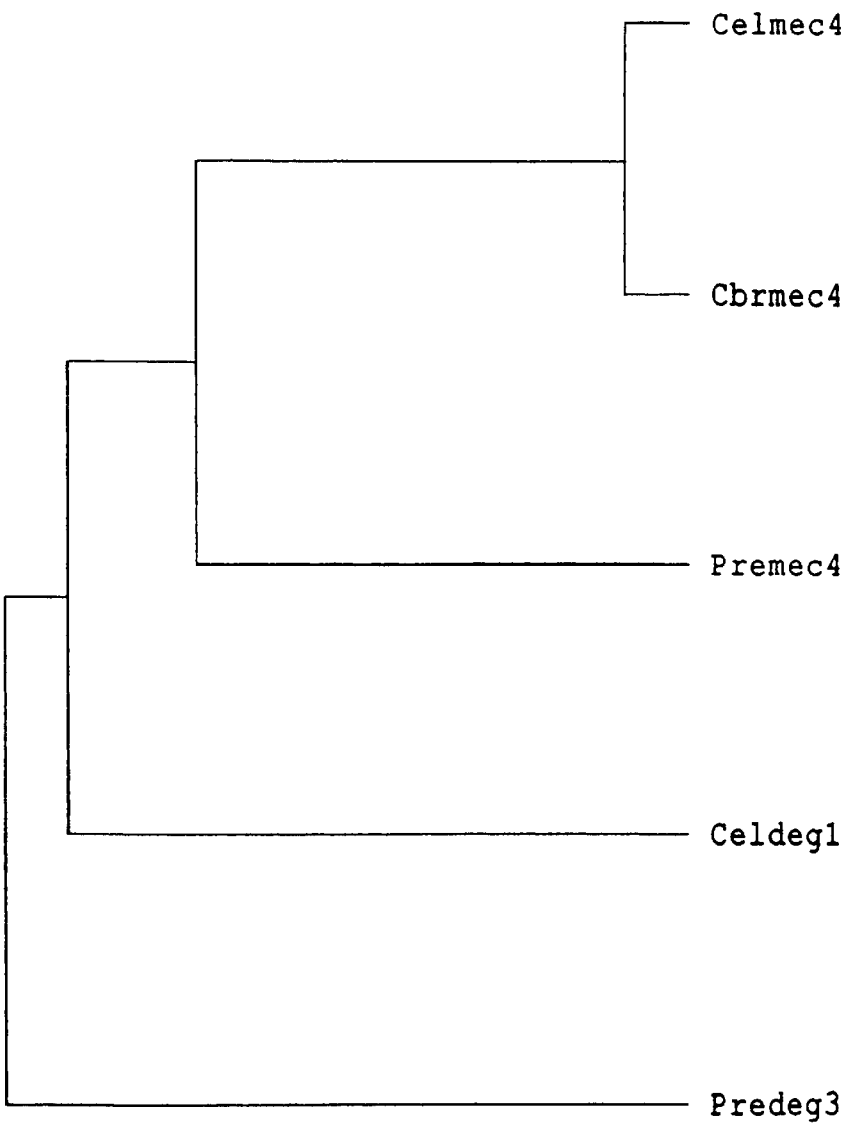
FIG. 23 is a dendrogram of sequence relationships of five degenerin deduced amino acid sequences. Sequences refer to those shown in the alignment of FIG. 21.

The overall relatedness of nine degenerins is shown as a dendrogram in FIG. 23. The grouping of sequences supports the notion that the gene duplication/triplication event(s) that generated the degenerin gene family preceded the separation of the nematode species under investigation by a significant period of time and may have preceded the origin of the phylum. The breadth of the degenerin database, the battery of consensus probes and the apparent ancient origin of this gene family suggests the presence of their human homologues, and the information disclosed here enables one to identify the human homologue.

EXAMPLE 8
Comparison of Deduced Nematode ced-4 Sequences

Figure 24B:
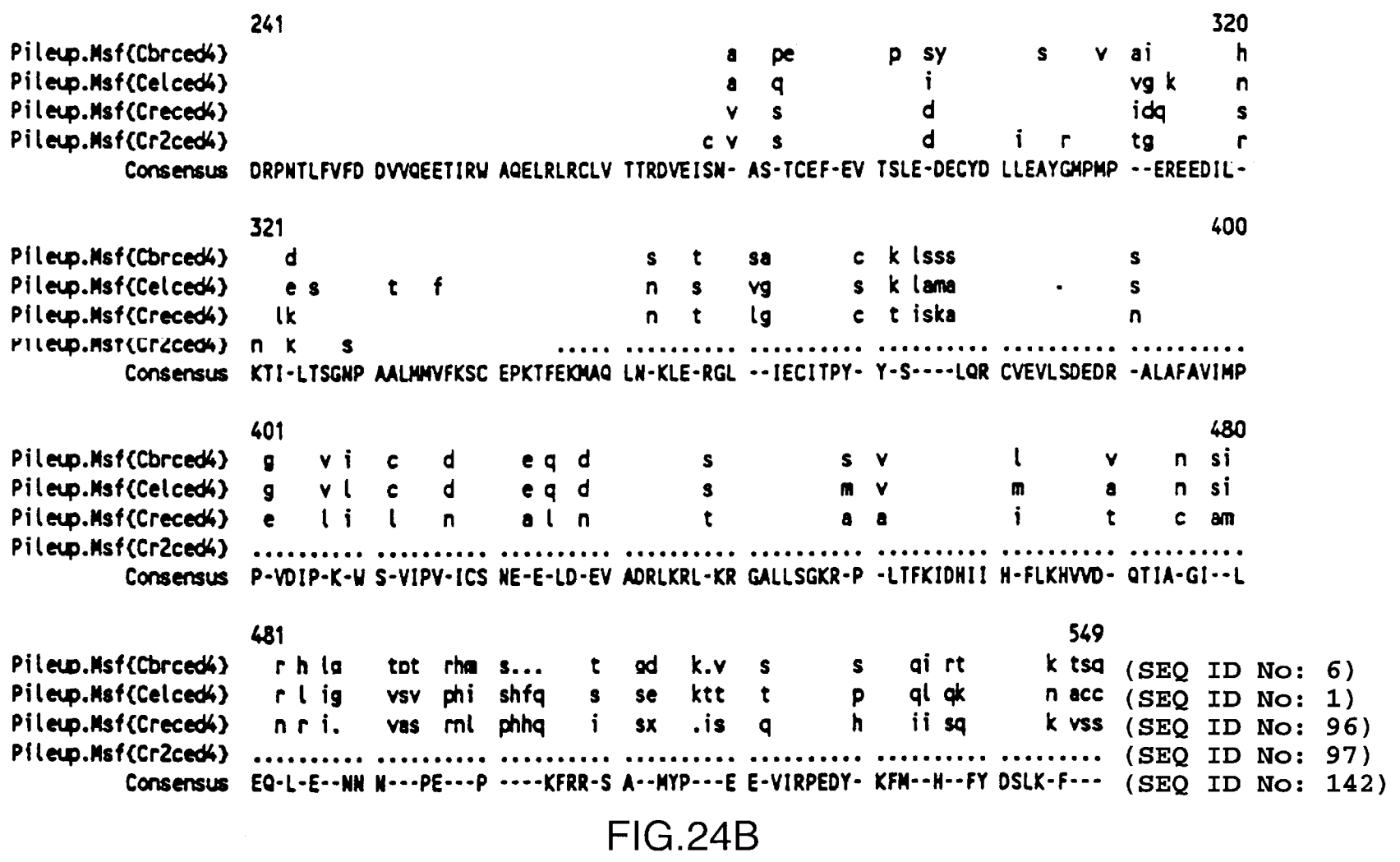

Our database of deduced ced-4 sequences is derived from analysis of four homologues identified in species of the genus Caenorhabditis. The genes from *C. elegans* and *C. briggsae* were sequenced completely; in both cases both cDNA and genomic DNA were analyzed. Two cDNA sequences were also obtained from amplification of *C. remanei* RNA, which appeared to be transcribed from two distinct genes. We aligned and analyzed these four sequences (see FIG. 24), as was described above for the degenerins.

Figures 25, 25A:
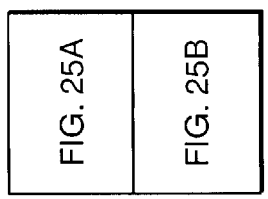
FIG. 25 is a list of 14 consensus peptides of ced-4 including the position of the N-terminal residue and the length of each peptide.

Pairwise comparisons of the deduced ced-4 sequences showed identity ranging from 70–80%. The sequence comparison indicated fourteen conserved stretches that qualified for design of degenerate probes and primers (FIG. 25). A dendrogram of sequence relationships (not shown) suggests that *C. briggsae* and *C. elegans* are more closely related to each other than either species is to *C. remanei*. This interpretation is consistent with analysis of ribosomal sequences in the genus. Furthermore, these data suggest that the gene duplication in *C. remanei* occurred shortly after speciation, when it separated from the lineage of *C. briggsae* and *C. elegans*.

The currently available consensus probes are used to clone homologues in more distantly related nematodes, which, upon analysis, result in the refined set of probes to progress out of the phylum for identification of a human homologue. The sequences of all four ced-4 proteins also provide a prototype of the relative spacing and of the amino acid sequences that allows one to recognize a ced-4 structural homologue.

EXAMPLE 9
Overall Design Considerations for Long Distance Homology Cloning

To identify human homologues of *C. elegans* cell death genes, we took several steps backward in evolutionary time towards a common ancestor as to obtain a consensus of deduced protein sequences in the common ancestor of *C.*

*elegans* and human, instead of taking a single giant leap from a *C. elegans* gene to a human gene.

Our degenerin database included sequences from three different family members, which emerged from a very early gene duplication event, and have evolved as separate proteins well before the orders Ascaridida and Rhabditida split (see FIG. 3) roughly 500 million years ago, indicating that the degenerins existed before the nematodes separated off from the coelomic metazoans. Further, an alignment of the mec-4 deduced sequences from *C. elegans* and *C. briggsae* showed that these proteins were 95% identical. This degree of sequence identity is roughly equivalent to the highly conserved heat shock proteins hsp3 and hsp16, which also have been compared in these two nematode species [Heschl et al. DNA 8:233 (1989)] and are known to retain approximately 80% sequence identity with their human counterparts. Thus, at least some of the degenerin consensus sequences are retained outside of the phylum.

In analyzing the data we recognized a total of 34 useful conserved areas—20 were from the degenerins (see FIG. 22 above) and 14 from ced-4 (see FIG. 25). FIG. 25 lists the 14 consensus ced-4 peptides identified in the alignment of all four ced-4 peptides. These peptides were ordered from amino to carboxyl termini and were assigned to exons according the gene sequences in *C. elegans* and *C. briggsae* (see FIGS. 4 and 9). Referring to FIG. 25, the position (POS.) specifies the first residue in a peptide length (L) and corresponds to the numbering of the *C. briggsae* ced-4 protein sequence. Some of the consensus peptide sequences (PEPTIDE) are adjacent to or split by introns (/). For the three longest peptides (PEPTIDE No. 10, 11 and 13), several substitutions were accommodated to retain these three peptides as intact consensus sequences.

The consensus peptides of the degenerin family were divided into three groups: (1) five signature peptides, which are retained in all degenerins; (2) twelve mec-4 consensus peptides, and; (3) three deg-3 consensus peptides. As suggested by FIG. 23, the genetic events that produced these three family members preceded the separation of the nematode lineages investigated, we use the five signature peptides (FIG. 19) which are the best mode for obtaining non-nematode homologues, including human.

EXAMPLE 10
Identification of Non-nematode (Ultimately Human) Degenerin Homologues We use techniques of PCR and screening with degenerate oligonucleotides to investigate both RNA/cDNA and genomic DNA sequences to advance the homology cloning of the degenerins out of the nematodes. Three homology cloning approaches (PCR/genomic DNA amplification, PCR/RNA amplification and degenerate probes/genomic libraries) are applied to the effort of seeking non-nematode homologues of the degenerins. When the PCR/RNA approach is taken, primers designed from areas identified in the consensus of the deduced degenerin sequences are used. Furthermore, several combinations of primers are tested.

Hybridization signals detected by the probes and/or candidate homologues amplified by PCR are analyzed and tested as described in the general homologue search strategy. Some consensus probe(s) (see FIG. 22) are used to identify the correct target in a non-nematode of the chordate lineage. The same probe(s) also lead us into the vertebrates and ultimately to human homologues. Additional probes are developed directly from sequences in the homologue of the non-nematode.

The initial group of non-nematode genomic libraries we investigate features deuterostomes that have relatively small genomes. Thus, fewer spurious hybridization/cloning events are encountered. *Ciona intestinalis* is a member of the ascidia, which diverged from the chordate lineage prior to the origin of the vertebrates. The genome of *C. intestinalis* is $1.5 \times 10^8$ bp [Laird, Chromosome 32:378 (1971)], which is less than twice that of *C. elegans*. For comparison, the human genome is forty times the size of the *C. elegans* genome. Other organism(s) of the chordate lineage that are included in the search are echinoderms, lamprey, puffer fish and mammals.

Note that the genes encoding any of the nematode degenerins can be readily cloned either from an appropriate genomic or cDNA library by using unique probes or primers identical to portions of the existing coding sequence (see FIGS. 7, 9, 13, 14, 15, 16, 17 18, 19 and 20) or by using a genomic or cDNA libraries and/or RNA or DNA prepared from the appropriate species and using the approach described above with degenerate primers and probes, such as those listed in FIG. 13.

EXAMPLE 11
Identification of Non-nematode (Ultimately Human) ced-4 Homologues We first supplement the database with additional deduced protein sequences from analysis of ced-4 genes identified in more distantly related nematodes. The same strategies and methods set forth in Example 10 for homology cloning of degenerins are used. The nematodes investigated include species belonging to other genera in the order Rhabditida (e.g. *Rhabditis maupasi*), as well as representatives of other orders in the class Secernentia (*Bruggia malayi*, *Haemonchus contortus*). Eventually, some very distantly related organisms in the phylum are included. With a broadened database through this analysis, we then use the refined set of probes and primers to advance the search out of the phylum to non-nematodes as described above.

EXAMPLE 12
Characterization of Putative Human Homologues

To determine whether any putative homologues bear extensive, non-selected resemblance to the prototype *C. elegans* cell death gene and gene product, we obtain more complete structural information on putative homologues by employing several PCR and probing methods to generate more extensive coding sequence information and deduced protein structure. Unique probes and primers are designed from putative coding regions (either exons from genomic DNAs, or coding strands of cDNA) and used to: (1) screen cDNA libraries and/or (2) amplify RNA populations through exon connection [Fearon et al. Science 247:493 (1990)], one-sided PCR [Ohara et al. Proc. Nat. Acad. Sci. 86:5673 (1989)], or RACE [Frohman et al. Proc. Natl. Acad. Sci. 85:8998 (1988)].

Two alternative approaches are taken to link adjacent coding sequences (exons) contained within fragments of genomic DNA clones by exon amplification [Buckler et al. Proc. Natl. Acad. Sci. USA 88:4005 1991)], or to identify coding sequences by cross-hybridization to genomic clones isolated from more closely related species (e.g., rat, human and bovine genomic clones can be compared). Coding sequences cloned with the unique probes and primers are sequenced on both strands. The deduced protein sequence can be compared to the *C. elegans* prototype cell death protein.

Great value is placed in the sequence databases of homologues from related nematodes that were compiled in FIGS. 21, 22, 24 and 25. Individual invariant residues as well as conserved stretches provide useful criteria for determining whether a putative homologue incorporates more dispersed structural features of the nematode gene product.

Use

It is of great use to clone a gene of an organism, e.g., a vertebrate, which is homologous to an identified gene in another organism, e.g., a non-vertebrate. First, knowledge gained about the gene of interest in the lower organism can facilitate the study on its homologue in the higher organism. Furthermore, identification of such a homologue in human or animals opens the door for development of both diagnostics and therapeutics involving that homologue. For example, isolation of human homologues of nematode cell death genes is not only relevant to the development of diagnostics for degenerative diseases, but also to the development of therapeutics based on compound screens for novel targets implicated in processes of cell death.

A large number of human diseases are characterized by tissue wasting or the untimely degeneration of specific populations of cells. Certain of these diseases affect the cells of the nervous system, either exclusively, or as part of a more generalized degeneration that has an effect on a particular part of the nervous system. For example, Alzheimer's Disease is a devastating neurodegenerative disorder caused by the premature loss of critical population of nerve cells in the brain that results in progressive dementia, physical incapacitation and death. In Amyotrophic Lateral Sclerosis (ALS or Lou Gehrig's disease) there is a degeneration only of the nerve cells controlling muscles, which eventually results in death from paralysis. People with diabetes often suffer from degeneration of the peripheral nerves in the latter stages of the disease. Some diseases, such as multiple sclerosis, cause neurodegeneration by destroying the support cells of the nervous system, the glia and Schwann cells, that are necessary for proper nerve function. To date, there are no effective therapies for either preventing or arresting the progress of any of these neurodegenerative diseases. Recent studies on AIDs pathology suggest that depletion of T-cell populations in infected individuals involves a programmed cell death pathway. E.g., see Marx, Science 254:498 (1991); Imberti et al. Science 254:860 (1991). Hence, there is great potential for discovery research and development programs centered around the isolation and analysis of the human genes implicated in the pathways responsible for the cell death, which is characteristic of all neurodegenerative disease, and any degenerative disease in general.

Identification and characterization of the genes that cause and control cell death may well provide valuable diagnostic reagents for degenerative diseases. Longer term potential, however, lies in a thorough understanding of the gene products and mechanisms of action which will provide a new generation of highly specific drug targets and will facilitate the development of new and powerful screening strategies for the discovery of novel cell protective neuroprotective medicines. Because of the underlying unification of several diseases through common cell death pathways, it is anticipated that the development of compounds active at these new targets will provide new therapeutics to combat a wide range of currently untreatable diseases. Further, an understanding of how cell death genes can be selectively activated can provide an effective treatment for cancer.

More specifically, when the cloned human gene is a homologue of a nematode disease gene, such as deg-1, mec-4, or deg-3, then one can seek direct genetic evidence that implicates this particular gene in human disease, i.e., look for the homologous human disease. This can be accomplished through mapping the location of these genes and any related genes on human chromosomes. Based on the appropriate map positions of the homologues, one could postulate (or exclude) linkage to an inherited degenerative disease that has been localized to the same chromosome or region of a chromosome. If such a disease is found nearby, RFLPs linked to the human homologue could be used to analyze disease pedigrees. Those studies would either establish or exclude linkage to the human gene. For several degenerative diseases, the pedigrees and the corresponding DNA blots already are available. Alternatively, homologues can serve as useful candidate genes for genes responsible for familial neurodegenerative disorders.

The approach to develop neuroprotective therapeutics depends on whether the gene product, thus the target for drug discovery and development, is known or unknown. To distinguish these two possibilities, two forms of detailed structural analyses of the sequence data can be adopted. One is to perform extensive database searching [Lipman et al. Science 227:1435 (1985)] with the primary goal being to determine whether the sequence falls into a previously characterized gene product or represents a novel structure. If the structure falls into a category of known/characterized function, a compound series based on previously studied interactions with the target can then be selected. If the homologue represents a novel structure, one can then resort either to structural predictions by modeling the deduced protein sequence or to compound screens based on functional properties.

Two approaches can be taken to evaluate whether a structural homologue is a functional human cell death gene. Both approaches depend on expression of the full-length gene product, obtained either from a complete cDNA or gene.

The first approach is to determine if expression of the human gene in mutant *C. elegans* strains can rescue a wild-type or a cell death related phenotype. The technologies necessary for studies of this type are well developed in *C. elegans*. For example, transgenic nematodes that express a human homologue of mec-4 regulated by a mec-4 promoter can be constructed to determine if wild-type behavior can be restored in touch-abnormal (mec-4 null mutant bearing) animals. Further, test on whether lesions in the human gene can induce the type of delayed-onset cell death characteristic of dominant alleles of mec-4 and deg-1 can be conducted. All three dominant alleles of mec-4 have been shown to result from missense mutations at a specific residue [Driscoll et al. Nature 349 (1991)]. Analogous mutations can be created in the human gene by site-directed mutagenesis to determine if expression of the mutant gene product in transgenic nematodes induces the "disease"— degeneration of specific touch receptor neurons during a late larval stage of development. Similar types of transgenic studies can be undertaken to determine if structural homologues of ced-3 and/or ced-4 can restore wild-type function (i.e., programmed cell death) to *C. elegans* null mutant strains.

The second approach involves expression of the homologue in *Xenopus oocytes* or in cultured mammalian cells or neurons. The question of primary interest is: does expression of a human homologue of a killer gene or of a mutated homologue of a disease gene lead to cell death? These questions can be addressed by performing two types of transient expression studies on homologues or on mutant forms thereof. Full-length cDNA clones can serve as templates to synthesize RNA in vitro that will be infected into oocytes. Alternatively, cDNAs can be subcloned into an expression vector and transformed into cultured neurons or fibroblasts. Molecular probes, including antibodies can be used to confirm that the protein is being expressed. The consequences of gene expression can be monitored by a number of biochemical and physiological assays designed to monitor cell survival.

Upon cloning of a functional homologue of a nematode cell death gene, additional steps can be taken to develop neuroprotective therapeutics. Information from the basic research studies on the genetics of nematode cell death provide a useful framework for designing these screens. On the other hand, creation of stable cell lines and transgenic mice containing the human cell death genes can lead to establishment of powerful animal models of degenerative diseases. Such models provide a unique set of tools for drug discovery and a basis for understanding the functional role of a human cell death genes in the pathophysiology of degenerative disease.

Other embodiments are also within the following claims.

What is claimed is:

1. A method for identifying a structural homologue in a first organism which is structurally homologous with a gene first identified in a second organism of a non-vertebrate phylum, said method comprising the steps of:
   (a) detecting, with two or more probes corresponding to nucleotide sequences of said gene, hybridization signals in the genome of a third organism which is positioned phylogenetically between said first organism and said second organism;
   (b) cloning said hybridization signals that are detected by at least two of said two or more probes, determining arrangement or strandedness of probe-binding regions in said cloned hybridization signals, and selecting candidate homologues from said hybridization signals based on sameness in arrangement or strandedness of said probe-binding regions;
   (c) sequencing said probe-binding regions in said candidate homologues and selecting putative homologues from said candidate homologues based on presence of an open reading frame in said sequenced probe-binding regions;
   (d) sequencing said putative homologues and selecting structural homologues from said putative homologues based on multiple resemblance in structural characteristics;
   (e) using additional two or more probes based on two or more conserved regions among said structural homologues and said gene to detect hybridization signals in the genome of an additional organism which is positioned phylogenetically between said first organisms and said additional organism; and
   (f) repeating steps b through e until said structural homologue of said first organism is identified.

2. The method of claim 1, wherein in step c regions surrounding said probe-binding regions are also sequenced and putative homologues are selected based on presence of an open reading frame in both said sequenced probe-binding regions and said regions surrounding them.

3. The method of claim 1, wherein in step b said hybridization signals show dispersed sequence similarity with said probes based on restriction/hybridization analysis.

4. The method of claim 1, wherein said candidate homologues are selected based on sameness in both arrangement and strandedness of said probe-binding regions.

5. The method of claim 1, wherein said putative homologues are selected further based on presence of a splice site.

6. The method of claim 2, wherein said putative homologues are selected further based on presence of a splice site.

7. The method of claim 5, wherein said putative homologues are selected further based on sequence similarity between said probe-binding regions and said probes.

8. The method of claim 6, wherein said putative homologues are selected further based on similarity in sequences beyond said probe-binding regions.

9. The method of claim 2, wherein said probes are used to screen a DNA library.

10. The method of claim 9, wherein said DNA library is a genomic library.

11. The method of claim 9, wherein said DNA library is a cDNA library.

12. The method of claim 1, wherein said probes are applied to genomic DNA analyzed on a Southern blot.

13. The method of claim 1, wherein said probes are degenerate.

14. The method of claim 1, wherein said probes used in step e are further based on intra-species conserved regions among members in a gene family.

15. The method of claim 1, wherein selection of said third organism is based on the rate of change for a protein during evolution.

16. The method of claim 1, wherein selection of said additional organism is based on the rate of change for a protein during evolution.

17. The method of claim 16, wherein selection of said third organism is based on the rate of change for a protein during evolution.

18. The method of claim 1, wherein said gene is ced-1, ced-2, ced-3, ced-4, ced-5, ced-6, ced-7, ced-8, ced-9, ced-10, mec-4, mec-6, deg-1, deg-3, egl-1, nuc-1, lin-24, or lin-33.

19. The method of claim 18, wherein said gene is ced-1, ced-2, ced-3, ced-4, ced-5, ced-6, ced-7, ced-8, ced-9, ced-10, mec-4, mec-6, deg-1, deg-3, egl-1, or nuc-1.

20. The method of claim 19, wherein said gene is ced-4, mec-4, deg-1, or deg-3.

21. A method for identifying a structural homologue in a first organism which is structurally homologous with a gene first identified in a second organism of a non-vertebrate phylum, said method comprising the steps of:
   (a) conducting PCR assays, with a pair of primers corresponding to a first and a second nucleotide sequences of said gene, on mRNA or DNA prepared from a third organism which is positioned phylogenetically between said first organism and diverged from said second organism;
   (b) selecting candidate homologues from the PCR products based on presence of an internal nucleotide sequence corresponding to a third nucleotide sequence of said gene which is disposed between said first and second nucleotide sequences of said gene;

(c) sequencing primer-binding regions in said candidate homologues and selecting putative homologues from said candidate homologues based on presence of an open reading frame in said sequenced primer-binding regions;

(d) sequencing said putative homologues and selecting structural homologues from said putative homologues based on multiple resemblance in structural characteristics;

(e) using an additional pair of primers based on conserved regions among said structural homologues and said gene to conduct PCR assays on mRNA or DNA prepared from an additional organism which is positioned phylogenetically between said first organism and said additional organisms; and (f) repeating steps b through e until a structural homologue of said first organism is identified.

22. The method of claim 21, wherein in step c regions surrounding said primer-binding regions are also sequenced and putative homologues are selected based on presence of an open reading frame in both said sequenced primer-binding regions and said regions surrounding them.

23. The method of claim 21, wherein said putative homologues are selected further based on presence of a splice site.

24. The method of claim 22, wherein said putative homologues are selected further based on presence of a splice site.

25. The method of claim 23, wherein said putative homologues are selected further based on sequence similarity between said primer-binding regions and said primers.

26. The method of claim 24, wherein said putative homologues are selected further based on similarity in sequences beyond said primer-binding regions.

27. The method of claim 21, wherein said primers are applied to RNA, reverse transcribed RNA, or DNA in a PCR amplification.

28. The method of claim 27, wherein said RNA is total RNA.

29. The method of claim 27, wherein said RNA is mRNA.

30. The method of claim 27, wherein said DNA is ds-cDNA or genomic DNA.

31. The method of claim 28, wherein said ds-cDNA or genomic DNA is fractionated or cloned.

32. The method of claim 21, wherein said primers are degenerate.

33. The method of claim 21, wherein said primers used in step e are further based on intra-species conserved regions among members in a gene family.

34. The method of claim 21, wherein selection of said third organism is based on the rate of change for a protein during evolution.

35. The method of claim 21, wherein selection of said additional organism is based on the rate of change for a protein during evolution.

36. The method of claim 35, wherein selection of said third organism is based on the rate of change for a protein during evolution.

37. The method of claim 21, wherein said gene is ced-1, ced-2, ced-3, ced-4, ced-5, ced-6, ced-7, ced-8, ced-9, ced-10, mec-4, mec-6, deg-1, deg-3, egl-1, nuc-1, lin-24, or lin-33.

38. The method of claim 21, wherein said gene is ced-1, ced-2, ced-3, ced-4, ced-5, ced-6, ced-7, ced-8, ced-9, ced-10, mec-4, mec-6, deg-1, deg-3, egl-1, or nuc-1.

39. The method of claim 37, wherein said gene is ced-4, mec-4, deg-1, or deg-3.

* * * * *

SEQUENCE LISTING (1) GENERAL INFORMATION:

(iii) NUMBER OF SEQUENCES: 143

(2) INFORMATION FOR SEQ ID NO: 1:

(i) SEQUENCE CHARACTERISTICS:
        (A) LENGTH:1859

(B) TYPE:nucleic acid (C) STRANDEDNESS:single (D) TOPOLOGY:linear (xi) SEQUENCE DESCRIPTION: SEQ ID NO: 1:

```
   GA ATT CCC GAA ATC GAA TGC CGC GCT TTG AGC ACG CGA CAC ACG AGG        47
      Ile Pro Glu Ile Glu Cys Arg Ala Leu Ser Thr Arg His Thr Arg
       1               5                  10                  15

CTC ATC CAC GAC TTT GAA CCA CGT GAC GCA TTG ACT TAT TTA GAA GGC        95
  Leu Ile His Asp Phe Glu Pro Arg Asp Ala Leu Thr Tyr Leu Glu Gly
                  20                  25                  30

AAA AAC ATT TTC ACA GAA GAT CAT TCT GAA CTT ATC AGT AAA ATG TCA       143
  Lys Asn Ile Phe Thr Glu Asp His Ser Glu Leu Ile Ser Lys Met Ser
                       35                  40                  45

ACT CGC CTC GAG AGG ATC GCC AAT TTT CTT CGA ATC TAT CGA CGT CAA       191
  Thr Arg Leu Glu Arg Ile Ala Asn Phe Leu Arg Ile Tyr Arg Arg Gln
               50                  55                  60

GCT TCT GAA CTT GGA CCA CTC ATC GAC TTT TTC AAC TAC AAC AAT CAA       239
  Ala Ser Glu Leu Gly Pro Leu Ile Asp Phe Phe Asn Tyr Asn Asn Gln
   65                  70                  75

AGT CAC CTT GCT GAT TTC CTC GAA GAC TAC ATC GAT TTT GCG ATA AAT       287
  Ser His Leu Ala Asp Phe Leu Glu Asp Tyr Ile Asp Phe Ala Ile Asn
   80                  85                  90                  95

GAG CCA GAT CTA CTT CGT CCA GTA GTG ATT GCT CCA CAA TTT TCC CGA       335
  Glu Pro Asp Leu Leu Arg Pro Val Val Ile Ala Pro Gln Phe Ser Arg
                      100                 105                 110

CAA ATG CTC GAT AGG AAA CTA TTG CTT GGG AAT GTT CCA AAA CAA ATG       383
  Gln Met Leu Asp Arg Lys Leu Leu Leu Gly Asn Val Pro Lys Gln Met
                  115                 120                 125

ACA TGC TAT ATT CGA GAG TAT CAC GTG GAT CGA GTG ATC AAA AAG CTC       431
  Thr Cys Tyr Ile Arg Glu Tyr His Val Asp Arg Val Ile Lys Lys Leu
                  130                 135                 140

GAC GAG ATG TGT GAT TTA GAC TCC TTT TTT CTG TTT CTA CAC GGC CGA       479
  Asp Glu Met Cys Asp Leu Asp Ser Phe Phe Leu Phe Leu His Gly Arg
          145                 150                 155

GCT GGA TCC GGA AAA TCA GTA ATT GCA TCA CAA GCT CTT TCG AAA TCT       527
  Ala Gly Ser Gly Lys Ser Val Ile Ala Ser Gln Ala Leu Ser Lys Ser
  160                 165                 170                 175

GAC CAA CTT ATT GGA ATA AAT TAT GAT TCA ATC GTT TGG CTC AAA GAT       575
```

```
                                     -continued

Asp Gln Leu Ile Gly Ile Asn Tyr Asp Ser Ile Val Trp Leu Lys Asp
                180                 185                 190

AGT GGA ACA GCT CCA AAA TCT ACA TTC GAT TTA TTT ACG GAT ATT TTG         623
Ser Gly Thr Ala Pro Lys Ser Thr Phe Asp Leu Phe Thr Asp Ile Leu
            195                 200                 205

CTG ATG CTA AAA AGC GAA GAC GAT CTT CTC AAT TTC CCA TCG GTG GAG         671
Leu Met Leu Lys Ser Glu Asp Asp Leu Leu Asn Phe Pro Ser Val Glu
            210                 215                 220

CAT GTC ACG TCA GTT GTA CTC AAA AGG ATG ATC TGC AAC GCA CTC ATT         719
His Val Thr Ser Val Val Leu Lys Arg Met Ile Cys Asn Ala Leu Ile
        225                 230                 235

GAT CGT CCA AAT ACT TTA TTC GTA TTT GAT GAC GTA GTT CAA GAA GAA         767
Asp Arg Pro Asn Thr Leu Phe Val Phe Asp Asp Val Val Gln Glu Glu
240                 245                 250                 255

ACA ATT CGT TGG GCT CAG GAG CTA CGT CTT CGA TGT CTT GTA ACT ACT         815
Thr Ile Arg Trp Ala Gln Glu Leu Arg Leu Arg Cys Leu Val Thr Thr
                260                 265                 270

CGT GAC GTG GAA ATA TCA AAT GCT GCT TCT CAA ACA TGC GAA TTC ATT         863
Arg Asp Val Glu Ile Ser Asn Ala Ala Ser Gln Thr Cys Glu Phe Ile
            275                 280                 285

GAA GTG ACA TCA TTG GAA ATC GAT GAA TGT TAT GAT TTT CTA GAA GCT         911
Glu Val Thr Ser Leu Glu Ile Asp Glu Cys Tyr Asp Phe Leu Glu Ala
            290                 295                 300

TAT GGA ATG CCG ATG CCT GTT GGA GAA AAA GAA GAA GAT GTG CTT AAT         959
Tyr Gly Met Pro Met Pro Val Gly Glu Lys Glu Glu Asp Val Leu Asn
        305                 310                 315

AAA ACA ATC GAA CTA AGC AGT GGA AAT CCA GCA ACG CTT ATG ATG TTT        1007
Lys Thr Ile Glu Leu Ser Ser Gly Asn Pro Ala Thr Leu Met Met Phe
320                 325                 330                 335

TTC AAG TCT TGT GAA CCG AAA ACA TTT GAA AAA ATG GCA CAG CTT AAT        1055
Phe Lys Ser Cys Glu Pro Lys Thr Phe Glu Lys Met Ala Gln Leu Asn
                340                 345                 350

AAC AAA TTG GAA AGT CGA GGA TTA GTC GGT GTT GAA TGT ATC ACC CCT        1103
Asn Lys Leu Glu Ser Arg Gly Leu Val Gly Val Glu Cys Ile Thr Pro
            355                 360                 365

TAC TCG TAC AAG TCA CTC GCA ATG GCT CTT CAA AGA TGT GTT GAA GTT        1151
Tyr Ser Tyr Lys Ser Leu Ala Met Ala Leu Gln Arg Cys Val Glu Val
        370                 375                 380

TTG TCA GAT GAG GAT CGA AGT GCT CTT GCT TTC GCA GTT GTG ATG CCT        1199
Leu Ser Asp Glu Asp Arg Ser Ala Leu Ala Phe Ala Val Val Met Pro
        385                 390                 395

CCT GGA GTT GAT ATA CCC GTC AAG CTA TGG TCA TGT GTT ATT CCA GTT        1247
Pro Gly Val Asp Ile Pro Val Lys Leu Trp Ser Cys Val Ile Pro Val
400                 405                 410                 415

GAT ATT TGT TCA AAT GAA GAA GAA CAA TTG GAT GAT GAA GTT GCG GAT        1295
Asp Ile Cys Ser Asn Glu Glu Glu Gln Leu Asp Asp Glu Val Ala Asp
                420                 425                 430

CGG TTG AAA AGA CTC AGC AAA CGT GGA GCT CTT CTC AGT GGA AAA CGA        1343
Arg Leu Lys Arg Leu Ser Lys Arg Gly Ala Leu Leu Ser Gly Lys Arg
            435                 440                 445

ATG CCC GTT TTG ACA TTC AAA ATT GAT CAT ATT ATC CAT ATG TTC TTG        1391
Met Pro Val Leu Thr Phe Lys Ile Asp His Ile Ile His Met Phe Leu
        450                 455                 460

AAA CAC GTC GTT GAT GCA CAA ACT ATC GCC AAT GGA ATC TCA ATT CTC        1439
Lys His Val Val Asp Ala Gln Thr Ile Ala Asn Gly Ile Ser Ile Leu
        465                 470                 475

GAG CAG CGT CTT CTT GAA ATA GGA AAC AAT AAT GTA TCA GTA CCG GAG        1487
Glu Gln Arg Leu Leu Glu Ile Gly Asn Asn Asn Val Ser Val Pro Glu
480                 485                 490                 495
```

```
CCA CAT ATA CCA TCA CAT TTC CAA AAA TTC CGT CGT TCA TCA GCC AGT        1535
Pro His Ile Pro Ser His Phe Gln Lys Phe Arg Arg Ser Ser Ala Ser
            500                 505                 510

GAG ATG TAT CCA AAA ACT ACA GAA GAA ACT GTG ATC CGT CCT GAA GAC        1583
Glu Met Tyr Pro Lys Thr Thr Glu Glu Thr Val Ile Arg Pro Glu Asp
            515                 520                 525

TTC CCA AAG TTC ATG CAA TTG CAC CAG AAA TTC TAT GAC TCC CTC AAA        1631
Phe Pro Lys Phe Met Gln Leu His Gln Lys Phe Tyr Asp Ser Leu Lys
            530                 535                 540

AAT TTT GCA TGC TGT TAAAACCTAT CGTGTACAAT ATTGCCTGTA TATTCCCCTC        1686
Asn Phe Ala Cys Cys
    545

GAAATACGTT TATACTTTTT CGCACGAGTT TTCTCATTTT TTCATTTGTA CTTGTTTTAT      1746

TTCTCTCCAA AATTTCAGAT CTATCCCAAA TGTTCTTAAA TTTAATGTTT TCTACAGATA      1806

CTCAACACAT CTTGTTTCAT CTCATCCTTG CTTTTTTTTT TTCAAATATA TTC             1859

(2) INFORMATION FOR SEQ ID NO: 2:

(i) SEQUENCE CHARACTERISTICS:
        (A) LENGTH:50

(B) TYPE:nucleic acid (C) STRANDEDNESS:single (D) TOPOLOGY:linear (xi) SEQUENCE DESCRIPTION: SEQ ID NO: 2:

GTTGATGCAC AAACTATCGC CAATGGAATC TCAATTCTCG AGCAGCGTCT                 50

(2) INFORMATION FOR SEQ ID NO: 3:

(i) SEQUENCE CHARACTERISTICS:
        (A) LENGTH:48

(B) TYPE:nucleic acid (C) STRANDEDNESS:single (D) TOPOLOGY:linear (xi) SEQUENCE DESCRIPTION: SEQ ID NO: 3:

GATGATGATA TACGGGAGCC CATGGAATCT CATAGCTCGA GCAGCACT                   48

(2) INFORMATION FOR SEQ ID NO: 4:

(i) SEQUENCE CHARACTERISTICS:
        (A) LENGTH:1100

(B) TYPE:nucleic acid (C) STRANDEDNESS:single (D) TOPOLOGY:linear (xi) SEQUENCE DESCRIPTION: SEQ ID NO: 4:

GA ATT CGT GTC CTT CTA TTC GTA AAC ACA TCA GAT TAT ATG TCA ACT         47
   Ile Arg Val Leu Leu Phe Val Asn Thr Ser Asp Tyr Met Ser Thr
   1               5                   10                  15

TCT GAG TCA TCC GGA GTT CGA CTG GCC ATC CAT CCA CCA ACT GAG TAC        95
Ser Glu Ser Ser Gly Val Arg Leu Ala Ile His Pro Pro Thr Glu Tyr
            20                  25                  30
```

```
CCG TTC CCC GAC ACA TTC GGC TAT TCT GCG CCA GTT GGT TTT GCA AGT        143
Pro Phe Pro Asp Thr Phe Gly Tyr Ser Ala Pro Val Gly Phe Ala Ser
             35                  40                  45

AGT TTT GGA ATC AAA AAG AAA GTG ATG CAA AGG TTG CCA GCA CCA TAT        191
Ser Phe Gly Ile Lys Lys Lys Val Met Gln Arg Leu Pro Ala Pro Tyr
         50                  55                  60

GGA GAA TGT GTA GAA ACG AAG AAA GTT GTA GAC AGA AAT TAT ATT TAC        239
Gly Glu Cys Val Glu Thr Lys Lys Val Val Asp Arg Asn Tyr Ile Tyr
     65                  70                  75

GCG GGG TAC GAT TAT CAT CCA GAA GGT TGT CAT AGA AGT TGC TTC CAA        287
Ala Gly Tyr Asp Tyr His Pro Glu Gly Cys His Arg Ser Cys Phe Gln
 80                  85                  90                  95

AAT GGA CTG ATT GAT GAT TGT TCG TGT GGA GAT CCT CGT TTC CCA GTA        335
Asn Gly Leu Ile Asp Asp Cys Ser Cys Gly Asp Pro Arg Phe Pro Val
                100                 105                 110

CCA GAA GGT TAT AGA CAT TGC TCG GCA TTT AAT GCA ACA GCT CGT ACC        383
Pro Glu Gly Tyr Arg His Cys Ser Ala Phe Asn Ala Thr Ala Arg Thr
            115                 120                 125

TGT CTT GAG AAG AAC ATT GGC TCA GTT GGA GAT TTC CAT CAT ATC ACT        431
Cys Leu Glu Lys Asn Ile Gly Ser Val Gly Asp Phe His His Ile Thr
        130                 135                 140

CAA AAA ATG GAC AAA TGC GTG TGT AAG CAA TCA TGT GAA GAA ATT ATT       479
Gln Lys Met Asp Lys Cys Val Cys Lys Gln Ser Cys Glu Glu Ile Ile
    145                 150                 155

CAT GAA GTT ACC TTT TCA TGC TCC AAA TGG CCT TCG GGA GCT ACT GAC        527
His Glu Val Thr Phe Ser Cys Ser Lys Trp Pro Ser Gly Ala Thr Asp
160                 165                 170                 175

CTT GGA GAC TGT GAT GGT ATG ACA GAA AGC GAG TGC GAA CAA TAC TAT        575
Leu Gly Asp Cys Asp Gly Met Thr Glu Ser Glu Cys Glu Gln Tyr Tyr
                180                 185                 190

CGG CTA AAT GCG GCA ATG ATC GAG GTA TTC TAC GAA CAA CTG AAC TAC        623
Arg Leu Asn Ala Ala Met Ile Glu Val Phe Tyr Glu Gln Leu Asn Tyr
            195                 200                 205

GAA CTG CTT CAA GAA TCA GAG GCA TAC GGT TTG GTT AAC TTG ATC GCC        671
Glu Leu Leu Gln Glu Ser Glu Ala Tyr Gly Leu Val Asn Leu Ile Ala
        210                 215                 220

GAT TTT GGA GGA CAT TTA GGA CTT TGG CTA GGA TTC TCC GTA ATC ACC        719
Asp Phe Gly Gly His Leu Gly Leu Trp Leu Gly Phe Ser Val Ile Thr
    225                 230                 235

GTG ATG GAA GTT TGT GTT CTG CTT GTT GAT ATG ATT TCC CTT TTC TTT        767
Val Met Glu Val Cys Val Leu Leu Val Asp Met Ile Ser Leu Phe Phe
240                 245                 250                 255

AAA AGT CGG CAC GAA GAA AAA CTT CTG AGA CAG AGC ACA AAA AGG AAA        815
Lys Ser Arg His Glu Glu Lys Leu Leu Arg Gln Ser Thr Lys Arg Lys
                260                 265                 270

GAT GTT CCA GAA GAT AAA CGG CAA ATT ACA GTT GGA TCA GGG CGA AAG        863
Asp Val Pro Glu Asp Lys Arg Gln Ile Thr Val Gly Ser Gly Arg Lys
            275                 280                 285

TCA GAC GCT TTC GTA TCA ATA                                            884
Ser Asp Ala Phe Val Ser Ile
        290

TAAATACCAA CTCTCTTTTG AACAACTATT ATATAACGTT AATTTTGAAC TGGGTTTCTC       944

AAGATGTAGT ATACAATGCT GTAACACGTT TCACCTTCAT TCGTTTTTTC CGATCTCTAA      1004

TTGTATATAG TGAGCTTTTT GATTAAAAAA AAAAAAAAAA AAAAAAAAAA AAAAAAAAAA      1064

AAAAAAAAAA AAAAAAAAAA AAAAAAAAAA AAAAA                                 1100
```

(2) INFORMATION FOR SEQ ID NO: 5:

(i) SEQUENCE CHARACTERISTICS:
    (A) LENGTH:4093
    (B) TYPE:nucleic acid
    (C) STRANDEDNESS:single
    (D) TOPOLOGY:linear (xi) SEQUENCE DESCRIPTION: SEQ ID NO: 5:

```
GAACATTCAA GCATGGAGAG GATGTAATTG TTTGGTGCAA AACATTCAAC GAAATTCATG      60

CGAAACTCGA TATTGTCAAT GAAAAGGTC ATAGGTTTGA AAGGGATCAA TGTATGTTTT      120

TTAGTAAGAA TTTATCGGAC TCAATTAAAA AAATTACAGG GATGGGATTC ACGCCAATTA     180

ACAGCAACTA CCGAGGATTT GGAAGAAGGA CGTGTGATCA TTACCAAACT AAAGGGAAAA     240

GATAAACTGC TATAAATATA ATAATGCTCA CTTCTCACCT ATTATGTGCC CATTTGCCAA     300

TATTTCTAAT TTTCAAATCT TACCTCCCTG TACAATGGAT CACCAATGAA ATAGATTTTA     360

TCTTTCTCAA AATTGTATTT GAATATTCGT TGTGTCGAAT GCACTATGAT CGTATTTATT     420

GAGCTAGTTT TTTTTTCATG TCAATGGTTC ATTTATAG                             458
```

| | | | | | |
|---|---|---|---|---|---|
| ATG CTT TGT GAA ATC GAA TGT CGA GCT TTG AAT GCA GCA CAC ACA ATG | | | | | 506 |
| Met Leu Cys Glu Ile Glu Cys Arg Ala Leu Asn Ala Ala His Thr Met | | | | | |
| 1               5                  10                 15 | | | | | |

```
CTC ATC CAG GAC TTC GAA CCA CGA GAT GCG CTA ACC TAT TTG GAA GGC       554
Leu Ile Gln Asp Phe Glu Pro Arg Asp Ala Leu Thr Tyr Leu Glu Gly
            20                  25                  30

GAA AAA ATT TTC ACA GAA GAC CAT TCT GAT CTC ATC AGT AAT ATG CCA       602
Glu Lys Ile Phe Thr Glu Asp His Ser Asp Leu Ile Ser Asn Met Pro
    35                  40                  45

ACT CGT CTT GAA AGA ATT GCG AAT TTC CTT CGA GCT TAT CGA CGG CAA      650
Thr Arg Leu Glu Arg Ile Ala Asn Phe Leu Arg Ala Tyr Arg Arg Gln
 50                  55                  60

GCG TCG GAA TTG GCT CCG CTC ATT GAC TTT TTC GAA TAC AAT AAT CAA       698
Ala Ser Glu Leu Ala Pro Leu Ile Asp Phe Phe Glu Tyr Asn Asn Gln
65                  70                  75                  80

AAT CAT CTG AAG GAC TTT CTT GAT GAG TAT CTC TGG TTT GCT ACA CAT       746
Asn His Leu Lys Asp Phe Leu Asp Glu Tyr Leu Trp Phe Ala Thr His
            85                  90                  95

CAA CCC GAT AAA CTA CGA CCT GTT GTG CTA GTT CCA AAA TTT TCA AGG       794
Gln Pro Asp Lys Leu Arg Pro Val Val Leu Val Pro Lys Phe Ser Arg
        100                 105                 110

CAA ATG CTT GAT CGT AAA CTT CTA CTG GGT AAC GTT CCG AAA CAA ATG       842
Gln Met Leu Asp Arg Lys Leu Leu Leu Gly Asn Val Pro Lys Gln Met
    115                 120                 125

AAC TGC TTC AGT AGA GAA TTC CAC GTG GAT CGA GTG ATC GAG AAG TTA       890
Asn Cys Phe Ser Arg Glu Phe His Val Asp Arg Val Ile Glu Lys Leu
130                 135                 140

GAC GAA ATG TGT GAT TTG                                                908
Asp Glu Met Cys Asp Leu
145                 150

GGTAAGTTGT CCGAGGGAAA CTGATCTTCA AGTTTCAGTT TCAAGCCTTG GTTCGGATTA     968

GTATTTTGAT TTTTTCA                                                     985

GAG TCT TTT TTC CTG TTT CTT CAC GGA CGC TCT GGA TCA GGA AAA TCC      1033
Glu Ser Phe Phe Leu Phe Leu His Gly Arg Ser Gly Ser Gly Lys Ser
            155                 160                 165

GTC ATC GCG TCA CAA GCA CTG TCG AAA TCA GAT CAA CTC ATT GGA ATG      1081
Val Ile Ala Ser Gln Ala Leu Ser Lys Ser Asp Gln Leu Ile Gly Ile
        170                 175                 180
```

-continued

```
TAAGATTTTT GAAACTGTTT CTGAATAAGC GAAATAAGAC ACTACGACTT TTAAAAGGAA    1141

TCATAAGATG ATATCTCGCA GTGAAAAGCA AAATATTCAG CACACAAAAT TTTTAAATTC    1201

AGAAATTAGG AATCAAACAT ATCCTTCAAG TTTTTGTAAT CCAAGAAAGG GACTCAATTA    1261

AATAATCTAA ATTTCTGTCA GCATTTCTTT TTCTAATATC TTTTATTTTA TTCAACTATT    1321

ATTTTAAGAC CATTTATTCA ACTATTATTT TAAGACCATT TATTCAACTA TTATTTTAAG    1381

A                                                                    1382
```

```
AAC TAC GAT TCT GTC GTG TGG CTC AAA GAT AGC GGA ACA ACG CCG AAA     1430
Asn Tyr Asp Ser Val Val Trp Leu Lys Asp Ser Gly Thr Thr Pro Lys
        185                 190                 195

GCC ACA TTC GAT TTA TTC ACA GAT CTA CTG CTG ATG CTC AAG             1472
Ala Thr Phe Asp Leu Phe Thr Asp Leu Leu Leu Met Leu Lys
    200                 205                 210
```

```
TGAGTCTTAA TCTTGTCCAG TGAAAAAAGA CACAAAGCAC AAAATTTCGA GATTATTTCG    1532

CAGAATATTT TTCTCTTTGC ACTTGCATGT TCTGTGTGTT TAAAGACGAG CCCGTGTTGT    1592

GAGCGACACG GATGACTCGC ACAACATGCC CGACTTCATT AACCGTGTTC TTTCAAGA     1650
```

```
AGT GAA GAC GAC CTG CTC AAT TTT CCG TCC GTC GAA CAC GTT ACA TCT     1698
Ser Glu Asp Asp Leu Leu Asn Phe Pro Ser Val Glu His Val Thr Ser
        215                 220                 225

GTT GTG CTG AAG AGA ATG                                             1716
Val Val Leu Lys Arg Met
    230
```

```
GTGAGTCTTT TCAAAGATTG CTGACTGTAT GTGACAAAAA ATAAAATGGG GTCTTGACTA    1776

CGTTAGATCA ATTTTACACC AATGTTGATT GTTGAGTTAA AAATTCAATT TTTTCAA      1833
```

```
ATT GCG AAC GCT CTC ATT GAC CGG CCA AAT ACT TTG TTC GTT CTT GAT     1881
Ile Ala Asn Ala Leu Ile Asp Arg Pro Asn Thr Leu Phe Val Leu Asp
235                 240                 245                 250

GAT GTG GTT CAA GAA GAC ACA ATC CGT TGG GCT CAG GAA CTT CGC CTT     1929
Asp Val Val Gln Glu Asp Thr Ile Arg Trp Ala Gln Glu Leu Arg Leu
        255                 260                 265

CGC TGT TTG ATC ACC ACC AGA GAT GTT GAA ATT TCA AAT GCA GCT TCA    1977
Arg Cys Leu Ile Thr Thr Arg Asp Val Glu Ile Ser Asn Ala Ala Ser
        270                 275                 280

CCG GAA TGC GAA TTT ATA GAA GTC ACA CCG TTG GAA AGT TAT GAA TGC     2025
Pro Glu Cys Glu Phe Ile Glu Val Thr Pro Leu Glu Ser Tyr Glu Cys
    285                 290                 295

TTC GAA TTG TTG GAA TCA TAT GGC ATG CCG GTG CCT GCT ATT GAG AGA     2073
Phe Glu Leu Leu Glu Ser Tyr Gly Met Pro Val Pro Ala Ile Glu Arg
    300                 305                 310

GAC GAG GAT ATC TTA CAC AAA ACC ATT GAT CTA ACG AGC GGA AAT CCA     2121
Asp Glu Asp Ile Leu His Lys Thr Ile Asp Leu Thr Ser Gly Asn Pro
315                 320                 325                 330

GCA GCT CTC ATG ATG ATT TTC AAG TCA TGC GAA CCG AAA ACA TTC GAG     2169
Ala Ala Leu Met Met Ile Phe Lys Ser Cys Glu Pro Lys Thr Phe Glu
        335                 340                 345

AAG                                                                 2172
Lys
```

```
TGAGTATAGT AAATATTTAA CTCGTTTCCC GAAAAAAAAA AAGAATTTCC GTTTCCGTTG    2232

GCCGTAAAGA CAAAATGTTC TTTCCGTTTC CGTTTGACGT CAGTTTTTCA GCAGAAACGG    2292

GATGGAACAG TTGATTTTTT TCAGTTTTCC GGAAGACTTT CGAAGATTTC TTCCATTCCC    2352

GTTTCCATAG AAAAAATTTA AAATTTTGTT TCCTCTTGCC GGAAATAATT TAACTCACTT    2412

AAAAAAAGGT TTTTTCATCT CAATATACCA CCTAAAGAAT CGCCCAAAAA AATACATTTT    2472
```

```
CAGG                                                                    2476

ATG GCC CAG CTG AAC AGT AAA CTG GAA ACT CGT GGA TTA TCT GCA ATT         2524
Met Ala Gln Leu Asn Ser Lys Leu Glu Thr Arg Gly Leu Ser Ala Ile
    350                 355                 360

GAA TGT ATC ACT CCC TAC TGT TAT AAG TCA CTA TCT AGT TCT CTC CAA         2572
Glu Cys Ile Thr Pro Tyr Cys Tyr Lys Ser Leu Ser Ser Ser Leu Gln
365                 370                 375

CGA TGT GTC GAA GTT CTT TCG GAT GAA GAT CGC AGC GCT TTG GCT TTT        2620
Arg Cys Val Glu Val Leu Ser Asp Glu Asp Arg Ser Ala Leu Ala Phe
380                 385                 390                 395

GCT GTT ATC ATG CCT CCA GGA ATA GAC ATT CCT GTC AAA ATA TGG TCT         2668
Ala Val Ile Met Pro Pro Gly Ile Asp Ile Pro Val Lys Ile Trp Ser
                400                 405                 410

TGC GTC ATT CCA GTG GAT ATA TGT TCC AAC GAA GAA GAT CAG TTA GAT         2716
Cys Val Ile Pro Val Asp Ile Cys Ser Asn Glu Glu Asp Gln Leu Asp
            415                 420                 425

GAC GAA GTG GCG GAT CGG TTG AAG AGA TTA AGC AAG                         2752
Asp Glu Val Ala Asp Arg Leu Lys Arg Leu Ser Lys
                430                 435

TAAGATGCTG TTCGGTATTA TGAATCTTCT CTAACACTGA TTTTACAGA                   2801

AGA GGA GCT CTG CTC AGT GGA AAA CGG TCC CCC GTT TTG ACC TAT AAA         2849
Arg Gly Ala Leu Leu Ser Gly Lys Arg Ser Pro Val Leu Thr Tyr Lys
440                 445                 450                 455

ATA GAT CAT GTC ATT CAT CTA TTC CTG AAG CAC GTG GTT GAT GTT CAG         2897
Ile Asp His Val Ile His Leu Phe Leu Lys His Val Val Asp Val Gln
                460                 465                 470

ACG ATT GCA                                                             2906
Thr Ile Ala

GTAAGTAATA CTCATAGAGA AAAATTTTTA TTTTCAGAAA TCAAAAACTT CTCAATTAAC       2966

TAATTCAGTC CCTTTATAAA ATTTGTGTTC AGCGAAAGTT CCATAAATTA ATCTTTTTC        3026

ACAG                                                                    3030

AAT GGA ATC TCG ATT CTT GAA CAA CGT CTT CAT GAG CTT GGA AAT AAC         3078
Asn Gly Ile Ser Ile Leu Glu Gln Arg Leu His Glu Leu Gly Asn Asn
475                 480                 485                 490

AAC ACG CCT ACA CCA GAA AGA CAT ATG CCA TCA AAA TTC CGT CGT ACA         3126
Asn Thr Pro Thr Pro Glu Arg His Met Pro Ser Lys Phe Arg Arg Thr
                495                 500                 505

TCT GCT GGT GAC ATG TTT CCA AAA GTG GAA GAT TCT GTT ATA CGC CCA         3174
Ser Ala Gly Asp Met Phe Pro Lys Val Glu Asp Ser Val Ile Arg Pro
            510                 515                 520

GAA GAT TAT TCA AAA TTC ATG CAA ATC CAT CGC ACT TTC TAT GAT TCC         3222
Glu Asp Tyr Ser Lys Phe Met Gln Ile His Arg Thr Phe Tyr Asp Ser
        525                 530                 535

CTA AAG AAG TTC ACA TCC CAA                                             3243
Leu Lys Lys Phe Thr Ser Gln
540                 545

TAGCTGTATA AGAATTTCTA TGCCTGTAAT TTCTTTCCAT ATAATTTATT CGCATGTAAT       3303

ATTTTCTCCT ATTCAGTATT TATTTTGAGC ACTTTCTGAC TGTATTTGTT TTACCCAACC       3363

CCCTCCCCCT TTTAAGCTTT TTTTATTGTA CGGATGATAA TCAGAATTTT GTTTGTTGAT       3423

ACTCAGAATC ATAGNTCACA GGTTGATTTC TCTTAAATCG TTCCCCATCT GAATCCAAAT       3483

TTTGTTTCTT ACTATAAATA TTATTGCATA TGATCGTGTA CTTTGTGCAT TATGTATTTT       3543

TTGTTGATCT CTTATTTCAA ATATTAATTA TTTATTTTTG TGCTTAAAAA CAGCTAATTT       3603

GATTATCCAG TTATGCAGTA GTTTCGAGAA GACCCCAACT TTATAAGTAA TCACCACTGT       3663
```

```
CGATACAGCT TCGAAAATGT GCGGTTCCTA TCGTCTGCTG TCATTTCTAC ATTTGGCATC    3723

CTTTTCCATA TTATTGAAAT GATATCCACC CATTGGTTTC CATGCAGGTT GATAGCTTTG    3783

TTNNTTCTTC TCTCTTTACA TATTGTTCGT TGTATTTCTC TGTTCCACAG CAACGGATAT    3843

TTTTTAGTGG TTTACCGCGT TTGGTCAATG GATTTCTCGG GCTAGAAGAG CTACATTCAA    3903

CGAACATAAT CTTCTGCTGA CCTATCAACC AAGAGCTTAC ACACACGGTC ATCTTTTCGT    3963

CGTGAGTTAC AAGGAAGCGA GGTTCTAAGC TTTTTCATCA AAACATTTCC AGCCTGATCC    4023

ACCGACACCA TGCGGATTCT CGAAAAATCC AACTGAATCA TGTACTGATT CGGAGTTTCG    4083

TCAAGCCCGT                                                           4093
```

(2) INFORMATION FOR SEQ ID NO: 6:

(i) SEQUENCE CHARACTERISTICS:
        (A) LENGTH:1638

(B) TYPE:nucleic acid (C) STRANDEDNESS:single (D) TOPOLOGY:linear (xi) SEQUENCE DESCRIPTION: SEQ ID NO: 6:

```
ATG CTT TGT GAA ATC GAA TGT CGA GCT TTG AAT GCA GCA CAC ACA ATG         48
Met Leu Cys Glu Ile Glu Cys Arg Ala Leu Asn Ala Ala His Thr Met
 1               5                  10                  15

CTC ATC CAG GAC TTC GAA CCA CGA GAT GCG CTA ACC TAT TTG GAA GGC         96
Leu Ile Gln Asp Phe Glu Pro Arg Asp Ala Leu Thr Tyr Leu Glu Gly
                20                  25                  30

GAA AAA ATT TTC ACA GAA GAC CAT TCT GAT CTC ATC AGT AAT ATG CCA        144
Glu Lys Ile Phe Thr Glu Asp His Ser Asp Leu Ile Ser Asn Met Pro
            35                  40                  45

ACT CGT CTT GAA AGA ATT GCG AAT TTC CTT CGA GCT TAT CGA CGG CAA        192
Thr Arg Leu Glu Arg Ile Ala Asn Phe Leu Arg Ala Tyr Arg Arg Gln
 50                  55                  60

GCG TCG GAA TTG GCT CCG CTC ATT GAC TTT TTC GAA TAC AAT AAT CAA        240
Ala Ser Glu Leu Ala Pro Leu Ile Asp Phe Phe Glu Tyr Asn Asn Gln
 65                  70                  75                  80

AAT CAT CTG AAG GAC TTT CTT GAT GAG TAT CTC TGG TTT GCT ACA CAT        288
Asn His Leu Lys Asp Phe Leu Asp Glu Tyr Leu Trp Phe Ala Thr His
                85                  90                  95

CAA CCC GAT AAA CTA CGA CCT GTT GTG CTA GTT CCA AAA TTT TCA AGG        336
Gln Pro Asp Lys Leu Arg Pro Val Val Leu Val Pro Lys Phe Ser Arg
               100                 105                 110

CAA ATG CTT GAT CGT AAA CTT CTA CTG GGT AAC GTT CCG AAA CAA ATG        384
Gln Met Leu Asp Arg Lys Leu Leu Leu Gly Asn Val Pro Lys Gln Met
            115                 120                 125

AAC TGC TTC AGT AGA GAA TTC CAC GTG GAT CGA GTG ATC GAG AAG TTA        432
Asn Cys Phe Ser Arg Glu Phe His Val Asp Arg Val Ile Glu Lys Leu
        130                 135                 140

GAC GAA ATG TGT GAT TTG GAG TCT TTT TTC CTG TTT CTT CAC GGA CGC       480
Asp Glu Met Cys Asp Leu Glu Ser Phe Phe Leu Phe Leu His Gly Arg
145                 150                 155                 160

TCT GGA TCA GGA AAA TCC GTC ATC GCG TCA CAA GCA CTG TCG AAA TCA        528
Ser Gly Ser Gly Lys Ser Val Ile Ala Ser Gln Ala Leu Ser Lys Ser
               165                 170                 175

GAT CAA CTC ATT GGA ATA AAC TAC GAT TCT GTC GTG TGG CTC AAA GAT        576
Asp Gln Leu Ile Gly Ile Asn Tyr Asp Ser Val Val Trp Leu Lys Asp
            180                 185                 190
```

```
AGC GGA ACA ACG CCG AAA GCC ACA TTC GAT TTA TTC ACA GAT CTA CTG          624
Ser Gly Thr Thr Pro Lys Ala Thr Phe Asp Leu Phe Thr Asp Leu Leu
        195                 200                 205

CTG ATG CTC AAA AGT GAA GAC GAC CTG CTC AAT TTT CCG TCC GTC GAA          672
Leu Met Leu Lys Ser Glu Asp Asp Leu Leu Asn Phe Pro Ser Val Glu
        210                 215                 220

CAC GTT ACA TCT GTT GTG CTG AAG AGA ATG ATT GCG AAC GCT CTC ATT          720
His Val Thr Ser Val Val Leu Lys Arg Met Ile Ala Asn Ala Leu Ile
225                 230                 235                 240

GAC CGG CCA AAT ACT TTG TTC GTT CTT GAT GAT GTG GTT CAA GAA GAC          768
Asp Arg Pro Asn Thr Leu Phe Val Leu Asp Asp Val Val Gln Glu Asp
                245                 250                 255

ACA ATC CGT TGG GCT CAG GAA CTT CGC CTT CGC TGT TTG ATC ACC ACC          816
Thr Ile Arg Trp Ala Gln Glu Leu Arg Leu Arg Cys Leu Ile Thr Thr
        260                 265                 270

AGA GAT GTT GAA ATT TCA AAT GCA GCT TCA CCG GAA TGC GAA TTT ATA          864
Arg Asp Val Glu Ile Ser Asn Ala Ala Ser Pro Glu Cys Glu Phe Ile
        275                 280                 285

GAA GTC ACA CCG TTG GAA AGT TAT GAA TGC TTC GAA TTG TTG GAA TCA          912
Glu Val Thr Pro Leu Glu Ser Tyr Glu Cys Phe Glu Leu Leu Glu Ser
        290                 295                 300

TAT GGC ATG CCG GTG CCT GCT ATT GAG AGA GAC GAG GAT ATC TTA CAC          960
Tyr Gly Met Pro Val Pro Ala Ile Glu Arg Asp Glu Asp Ile Leu His
305                 310                 315                 320

AAA ACC ATT GAT CTA ACG AGC GGA AAT CCA GCA GCT CTC ATG ATG ATT         1008
Lys Thr Ile Asp Leu Thr Ser Gly Asn Pro Ala Ala Leu Met Met Ile
                325                 330                 335

TTC AAG TCA TGC GAA CCG AAA ACA TTC GAG AAG ATG GCC CAG CTG AAC         1056
Phe Lys Ser Cys Glu Pro Lys Thr Phe Glu Lys Met Ala Gln Leu Asn
        340                 345                 350

AGT AAA CTG GAA ACT CGT GGA TTA TCT GCA ATT GAA TGT ATC ACT CCC         1104
Ser Lys Leu Glu Thr Arg Gly Leu Ser Ala Ile Glu Cys Ile Thr Pro
        355                 360                 365

TAC TGT TAT AAG TCA CTA TCT AGT TCT CTC CAA CGA TGT GTC GAA GTT         1152
Tyr Cys Tyr Lys Ser Leu Ser Ser Ser Leu Gln Arg Cys Val Glu Val
        370                 375                 380

CTT TCG GAT GAA GAT CGC AGC GCT TTG GCT TTT GCT GTT ATC ATG CCT         1200
Leu Ser Asp Glu Asp Arg Ser Ala Leu Ala Phe Ala Val Ile Met Pro
385                 390                 395                 400

CCA GGA ATA GAC ATT CCT GTC AAA ATA TGG TCT TGC GTC ATT CCA GTG         1248
Pro Gly Ile Asp Ile Pro Val Lys Ile Trp Ser Cys Val Ile Pro Val
                405                 410                 415

GAT ATA TGT TCC AAC GAA GAA GAT CAG TTA GAT GAC GAA GTG GCG GAT         1296
Asp Ile Cys Ser Asn Glu Glu Asp Gln Leu Asp Asp Glu Val Ala Asp
        420                 425                 430

CGG TTG AAG AGA TTA AGC AAA AGA GGA GCT CTG CTC AGT GGA AAA CGG         1344
Arg Leu Lys Arg Leu Ser Lys Arg Gly Ala Leu Leu Ser Gly Lys Arg
        435                 440                 445

TCC CCC GTT TTG ACC TAT AAA ATA GAT CAT GTC ATT CAT CTA TTC CTG         1392
Ser Pro Val Leu Thr Tyr Lys Ile Asp His Val Ile His Leu Phe Leu
450                 455                 460

AAG CAC GTG GTT GAT GTT CAG ACG ATT GCA AAT GGA ATC TCG ATT CTT         1440
Lys His Val Val Asp Val Gln Thr Ile Ala Asn Gly Ile Ser Ile Leu
465                 470                 475                 480

GAA CAA CGT CTT CAT GAG CTT GGA AAT AAC AAC ACG CCT ACA CCA GAA         1488
Glu Gln Arg Leu His Glu Leu Gly Asn Asn Asn Thr Pro Thr Pro Glu
                485                 490                 495

AGA CAT ATG CCA TCA AAA TTC CGT CGT ACA TCT GCT GGT GAC ATG TTT         1536
Arg His Met Pro Ser Lys Phe Arg Arg Thr Ser Ala Gly Asp Met Phe
```

```
                500             505             510
CCA AAA GTG GAA GAT TCT GTT ATA CGC CCA GAA GAT TAT TCA AAA TTC    1584
Pro Lys Val Glu Asp Ser Val Ile Arg Pro Glu Asp Tyr Ser Lys Phe
        515                 520                 525

ATG CAA ATC CAT CGC ACT TTC TAT GAT TCC CTA AAG AAG TTC ACA TCC    1632
Met Gln Ile His Arg Thr Phe Tyr Asp Ser Leu Lys Lys Phe Thr Ser
        530                 535                 540

CAA                                                                1635
Gln
545

TAG                                                                1638
```

(2) INFORMATION FOR SEQ ID NO: 7:

(i) SEQUENCE CHARACTERISTICS:
        (A) LENGTH:30

(B) TYPE:nucleic acid (C) STRANDEDNESS:single (D) TOPOLOGY:linear (xi) SEQUENCE DESCRIPTION: SEQ ID NO: 7:

```
CGAATTCGGA TCCGARCAYG TNACNTCNGT                                     30
```

(2) INFORMATION FOR SEQ ID NO: 8:

(i) SEQUENCE CHARACTERISTICS:
        (A) LENGTH:30

(B) TYPE:nucleic acid (C) STRANDEDNESS:single (D) TOPOLOGY:linear (xi) SEQUENCE DESCRIPTION: SEQ ID NO: 8:

```
CGAATTCGGA TCCGTNCARG ARGARACNAT                                     30
```

(2) INFORMATION FOR SEQ ID NO: 9:

(i) SEQUENCE CHARACTERISTICS:
        (A) LENGTH:30

(B) TYPE:nucleic acid (C) STRANDEDNESS:single (D) TOPOLOGY:linear (xi) SEQUENCE DESCRIPTION: SEQ ID NO: 9:

```
CGAATTCGGA TCCGTNGCNG GRTTNCCRCT                                     30
```

(2) INFORMATION FOR SEQ ID NO: 10:

(i) SEQUENCE CHARACTERISTICS:
        (A) LENGTH:32

(B) TYPE:nucleic acid (C) STRANDEDNESS:single (D) TOPOLOGY:linear (xi) SEQUENCE DESCRIPTION: SEQ ID NO: 10:

CATCGATGGA TCCTTYTTYC TNTTYCTNCY GG                32

(2) INFORMATION FOR SEQ ID NO: 11:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 11:

CGAATTCGGA TCCACNGANG TNACRTGYTC NAC               33

(2) INFORMATION FOR SEQ ID NO: 12:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 12:

CGAATTCGGA TCCTTYTCRA ANGTYTTNGG YTC               33

(2) INFORMATION FOR SEQ ID NO: 13:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 13:

CGAATTCGGA TCCTTYTCRA ANGTYTTNGG YTC               33

(2) INFORMATION FOR SEQ ID NO: 14:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 14:

CATCGATGGA TCCACNGANG TNACRTGYTC NAC               33

(2) INFORMATION FOR SEQ ID NO: 15:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 15:

CATCGATGGA TCCGTNTGGC TNAARGAYAG YGG                33

(2) INFORMATION FOR SEQ ID NO: 16:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 16:

CGAATTCGGA TCCTCRAGNG TYTTNGGYTC RCA                33

(2) INFORMATION FOR SEQ ID NO: 17:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 17:

ACNATHAGRT GGGCNCARGA                               20

(2) INFORMATION FOR SEQ ID NO: 18:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 18:

ACNATHCGNT GGGCNCARGA                               20

(2) INFORMATION FOR SEQ ID NO: 19:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 19:

CATCGATGGA TCCGGNAAYG TNCCNAARCA RAT                33

(2) INFORMATION FOR SEQ ID NO: 20:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 20:

CGAATTCGGA TCCATNCCRT TNGCDATNGT YTG                              33

(2) INFORMATION FOR SEQ ID NO: 21:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 21:

GAYGAYGTNG TNCARGARGA                                              20

(2) INFORMATION FOR SEQ ID NO: 22:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 22:

CGAATTCGGA TCCATRTCNA CNGGDATNAC RCA                              33

(2) INFORMATION FOR SEQ ID NO: 23:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 23:

TGYGARCCNA ARACNTTYGA                                              20

(2) INFORMATION FOR SEQ ID NO: 24:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 24:

CGAATTCGGA TCCTGNGCCC ANCGDATNGT YTC                                        33

(2) INFORMATION FOR SEQ ID NO: 25:

(i) SEQUENCE CHARACTERISTICS:
            (A) LENGTH:33

(B) TYPE:nucleic acid (C) STRANDEDNESS:single (D) TOPOLOGY:linear (xi) SEQUENCE DESCRIPTION: SEQ ID NO: 25:

CGAATTCGGA TCCTGNGCCC AYCTDATNGT YTC                                        33

(2) INFORMATION FOR SEQ ID NO: 26:

(i) SEQUENCE CHARACTERISTICS:
            (A) LENGTH:33

(B) TYPE:nucleic acid (C) STRANDEDNESS:single (D) TOPOLOGY:linear (xi) SEQUENCE DESCRIPTION: SEQ ID NO: 26:

CATCGATGGA TCCACNMGNG AYGTNGARAT HTC                                        33

(2) INFORMATION FOR SEQ ID NO: 27:

(i) SEQUENCE CHARACTERISTICS:
            (A) LENGTH:33

(B) TYPE:nucleic acid (C) STRANDEDNESS:single (D) TOPOLOGY:linear (xi) SEQUENCE DESCRIPTION: SEQ ID NO: 27:

CATCGATGGA TCCACNMGNG AYGTNGARAT HAG                                        33

(2) INFORMATION FOR SEQ ID NO: 28:

(i) SEQUENCE CHARACTERISTICS:
            (A) LENGTH:29

(B) TYPE:nucleic acid (C) STRANDEDNESS:single (D) TOPOLOGY:linear (xi) SEQUENCE DESCRIPTION: SEQ ID NO: 28:

ACACTGCAGT CRAANGTYTT NGGYTCRCA                                             29

(2) INFORMATION FOR SEQ ID NO: 29:

(i) SEQUENCE CHARACTERISTICS:
            (A) LENGTH:28

(B) TYPE:nucleic acid (C) STRANDEDNESS:single (D) TOPOLOGY:linear (xi) SEQUENCE DESCRIPTION: SEQ ID NO: 29:

ACACTGCAGA YTTYGARCCN CGNGAYGC                28

(2) INFORMATION FOR SEQ ID NO: 30:

(i) SEQUENCE CHARACTERISTICS:
        (A) LENGTH:28

(B) TYPE:nucleic acid (C) STRANDEDNESS:single (D) TOPOLOGY:linear (xi) SEQUENCE DESCRIPTION: SEQ ID NO: 30:

ACACTGCAGA YGAYGTNGTN CARGARGA                28

(2) INFORMATION FOR SEQ ID NO:

(i) SEQUENCE CHARACTERISTICS:
        (A) LENGTH:28

(B) TYPE:nucleic acid (C) STRANDEDNESS:single (D) TOPOLOGY:linear (xi) SEQUENCE DESCRIPTION: SEQ ID NO: 31:

ACACTGCAGT NTGGYTNAAR GAYAGYGG                28

(2) INFORMATION FOR SEQ ID NO: 32:

(i) SEQUENCE CHARACTERISTICS:
        (A) LENGTH:34

(B) TYPE:nucleic acid (C) STRANDEDNESS:single (D) TOPOLOGY:linear (xi) SEQUENCE DESCRIPTION: SEQ ID NO: 32:

ATACTCGAGC CACCATGCTT TGTGAAATCG AATG                34

(2) INFORMATION FOR SEQ ID NO: 33:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 33:

ACTCTCGAGC TATTGGGATG TGAACTTCTT TAG                33

(2) INFORMATION FOR SEQ ID NO: 34:

(i) SEQUENCE CHARACTERISTICS:
        (A) LENGTH:29

(B) TYPE:nucleic acid (C) STRANDEDNESS:single (D) TOPOLOGY:linear (xi) SEQUENCE DESCRIPTION: SEQ ID NO: 34:

AACACTGCAG TNTGGYTNAA RGAYTCNGG                     29

(2) INFORMATION FOR SEQ ID NO: 35:

(i) SEQUENCE CHARACTERISTICS:
        (A) LENGTH:30

(B) TYPE:nucleic acid (C) STRANDEDNESS:single (D) TOPOLOGY:linear (xi) SEQUENCE DESCRIPTION: SEQ ID NO: 35:

AACACTCCAG TCYTCYTGNA CNACRTCRTC                    30

(2) INFORMATION FOR SEQ ID NO: 36:

(i) SEQUENCE CHARACTERISTICS:
        (A) LENGTH:30

(B) TYPE:nucleic acid (C) STRANDEDNESS:single (D) TOPOLOGY:linear (xi) SEQUENCE DESCRIPTION: SEQ ID NO: 36:

AACACTCCAG ATYTCNAGRT CYCTNGTNGT                    30

(2) INFORMATION FOR SEQ ID NO: 37:

(i) SEQUENCE CHARACTERISTICS:
        (A) LENGTH:1600

(B) TYPE:nucleic acid (C) STRANDEDNESS:single (D) TOPOLOGY:linear (xi) SEQUENCE DESCRIPTION: SEQ ID NO: 37:

```
  G GAA TGG GAT GGA ATG GAA GAA TAT GAC AAT GAG CAT TAT GAG AAT        46
    Glu Trp Asp Gly Met Glu Glu Tyr Asp Asn Glu His Tyr Glu Asn
     1               5                  10                  15

TAC GAT GTG GAA GCA ACT ACT GGA ATG AAT ATG ATG GAA GAA TGT CAA        94
Tyr Asp Val Glu Ala Thr Thr Gly Met Asn Met Met Glu Glu Cys Gln
                 20                  25                  30

TCA GAG AGA ACA AAT TCG ACG AGC CCG ACG GGA TTT GAC GAT CGG TGT       142
Ser Glu Arg Thr Asn Ser Thr Ser Pro Thr Gly Phe Asp Asp Arg Cys
                 35                  40                  45
```

| | | |
|---|---|---|
| ATT TGC GCT TTC GAT AGA TCA ACT CAT GAT GCG TGG CCC TGT TTT CTG<br>Ile Cys Ala Phe Asp Arg Ser Thr His Asp Ala Trp Pro Cys Phe Leu<br>            50                      55                      60 | 190 |

| | | |
|---|---|---|
| AAC GGA ACC TGG GAA ACC ACC GAA TGT GAT ACT TGC AAT GAA CAT GCT<br>Asn Gly Thr Trp Glu Thr Thr Glu Cys Asp Thr Cys Asn Glu His Ala<br>        65                      70                      75 | 238 |

| | | |
|---|---|---|
|  TTC TGC ACC AAA GAT AAC AAA ACT GCG AAG GGC CAT AGA TCC CCA TGT<br>Phe Cys Thr Lys Asp Asn Lys Thr Ala Lys Gly His Arg Ser Pro Cys<br>80                    85                      90                      95 | 286 |

| | | |
|---|---|---|
| ATT TGT GCT CCA TCT AGA TTC TGT GTA GCA TAC AAC GGA AAG ACG CCA<br>Ile Cys Ala Pro Ser Arg Phe Cys Val Ala Tyr Asn Gly Lys Thr Pro<br>                    100                    105                    110 | 334 |

| | | |
|---|---|---|
| CCA ATT GAA ATT TGG ACA TAT CTT CAA GGA GGA ACT CCA ACT GAA GAT<br>Pro Ile Glu Ile Trp Thr Tyr Leu Gln Gly Gly Thr Pro Thr Glu Asp<br>                115                      120                  125 | 382 |

| | | |
|---|---|---|
| CCA AAC TTC CTT GAA GCT ATG GGA TTT CAG GGA ATG ACA GAT GAA GTT<br>Pro Asn Phe Leu Glu Ala Met Gly Phe Gln Gly Met Thr Asp Glu Val<br>          130                    135                    140 | 430 |

| | | |
|---|---|---|
| GCA ATT GTC ACT AAA GCC AAG GAA AAC ATC ATG TTT GCA ATG GCT ACC<br>Ala Ile Val Thr Lys Ala Lys Glu Asn Ile Met Phe Ala Met Ala Thr<br>          145                    150                    155 | 478 |

| | | |
|---|---|---|
| TTG TCA ATG CAA GAT AGG GAA CGG CTA AGT ACT ACA AAA AGG GAA CTT<br>Leu Ser Met Gln Asp Arg Glu Arg Leu Ser Thr Thr Lys Arg Glu Leu<br>160                  165                    170                    175 | 526 |

| | | |
|---|---|---|
| GTC CAC AAG TGC TCG TTT AAC GGA AAA GCG TGT GAT ATC GAA GCA GAT<br>Val His Lys Cys Ser Phe Asn Gly Lys Ala Cys Asp Ile Glu Ala Asp<br>                    180                    185                    190 | 574 |

| | | |
|---|---|---|
| TTT CTG ACT CAT ATT GAC CCT GCG TTT GGT TCG TGC TTT ACC TTC AAT<br>Phe Leu Thr His Ile Asp Pro Ala Phe Gly Ser Cys Phe Thr Phe Asn<br>                195                      200                  205 | 622 |

| | | |
|---|---|---|
| CAT AAT CGA ACA GTA AAC TTG ACT AGT ATT CGA GCA GGT CCC ATG TAC<br>His Asn Arg Thr Val Asn Leu Thr Ser Ile Arg Ala Gly Pro Met Tyr<br>                    210                    215                    220 | 670 |

| | | |
|---|---|---|
| GGA TTA CGT ATG CTG GTT TAT GTA AAC GCG TCT GAC TAT ATG CCA ACC<br>Gly Leu Arg Met Leu Val Tyr Val Asn Ala Ser Asp Tyr Met Pro Thr<br>          225                    230                    235 | 718 |

| | | |
|---|---|---|
| ACG GAA GCC ACA GGC GTT CGT TTG ACT ATT CAT GAC AAA GAA GAT TTC<br>Thr Glu Ala Thr Gly Val Arg Leu Thr Ile His Asp Lys Glu Asp Phe<br>240                  245                    250                    255 | 766 |

| | | |
|---|---|---|
| CCA TTT CCT GAT ACG TTC GGT TAT TCT GCT CCA ACT GGA TAT GTA TCC<br>Pro Phe Pro Asp Thr Phe Gly Tyr Ser Ala Pro Thr Gly Tyr Val Ser<br>                    260                    265                    270 | 814 |

| | | |
|---|---|---|
| TCA TTT GGA TTA CGA TTG CGA AAG ATG TCA CGT TTG CCA GCA CCT TAT<br>Ser Phe Gly Leu Arg Leu Arg Lys Met Ser Arg Leu Pro Ala Pro Tyr<br>          275                    280                    285 | 862 |

| | | |
|---|---|---|
| GGA GAT TGT GTG CCA GAT GGC AAA ACA TCG GAC TAT ATT TAC AGC AAT<br>Gly Asp Cys Val Pro Asp Gly Lys Thr Ser Asp Tyr Ile Tyr Ser Asn<br>          290                    295                    300 | 910 |

| | | |
|---|---|---|
| TAT GAA TAT TCG GTA GAG GGC TGC TAC CGT TCT TGC TTC CAA CAA CTC<br>Tyr Glu Tyr Ser Val Glu Gly Cys Tyr Arg Ser Cys Phe Gln Gln Leu<br>          305                    310                    315 | 958 |

| | | |
|---|---|---|
| GTG CTG AAA GAG TGC AGA TGT GGA GAT CCA CGT TTC CCA GTC CCT GAA<br>Val Leu Lys Glu Cys Arg Cys Gly Asp Pro Arg Phe Pro Val Pro Glu<br>320                  325                    330                    335 | 1006 |

| | | |
|---|---|---|
| AAT GCA CGG CAT TGC GAT GCA GCA GAC CCT ATT GCA AGA AAA TGT CTT<br>Asn Ala Arg His Cys Asp Ala Ala Asp Pro Ile Ala Arg Lys Cys Leu<br>                    340                    345                    350 | 1054 |

| | | |
|---|---|---|
| GAC GCC AGA ATG AAT GAC TTG GGA GGC CTA CAC GGA TCT TTC CGT TGC<br>Asp Ala Arg Met Asn Asp Leu Gly Gly Leu His Gly Ser Phe Arg Cys<br>                355                      360                  365 | 1102 |

```
AGA TGC CAA CAA CCA TGC CGC CAG TCA ATC TAC TCC GTT ACA TAC TCG    1150
Arg Cys Gln Gln Pro Cys Arg Gln Ser Ile Tyr Ser Val Thr Tyr Ser
            370                 375                 280

CCG GCA AAG TGG CCG TCG TTA TCT TTG CAA ATT CAA CTA GGA TCG TGT    1198
Pro Ala Lys Trp Pro Ser Leu Ser Leu Gln Ile Gln Leu Gly Ser Cys
            385                 390                 395

AAT GGT ACA GCG GTA GAG TGT AAT AAG CAT TAT AAA GAG AAC GGA GCA    1246
Asn Gly Thr Ala Val Glu Cys Asn Lys His Tyr Lys Glu Asn Gly Ala
400                 405                 410                 415

ATG GTG GAA GTG TTC TAC GAG CAG TTG AAT TTT GAA ATG CTC ACT GAA    1294
Met Val Glu Val Phe Tyr Glu Gln Leu Asn Phe Glu Met Leu Thr Glu
            420                 425                 430

TCA GAG GCT TAT GGG TTT GTC AAC TTG CTA GCC GAT TTT GGT GGA CAA    1342
Ser Glu Ala Tyr Gly Phe Val Asn Leu Leu Ala Asp Phe Gly Gly Gln
            435                 440                 445

CTC GGT CTT TGG TGC GGA ATA TCC TTC CTT ACC TGT TGC GAA TTT GTG    1390
Leu Gly Leu Trp Cys Gly Ile Ser Phe Leu Thr Cys Cys Glu Phe Val
            450                 455                 460

TTC CTT TTC TTG GAA ACT GCC TAC ATG AGT GCC GAA CAT AAC TAC TCT    1438
Phe Leu Phe Leu Glu Thr Ala Tyr Met Ser Ala Glu His Asn Tyr Ser
465                 470                 475

CTG TAC AAA AAG AAG AAG GCT GAG AAG GCA AAG AAA ATT GCG TCT GGA   1486
Leu Tyr Lys Lys Lys Lys Ala Glu Lys Ala Lys Lys Ile Ala Ser Gly
480                 485                 490                 495

TCT TTC                                                            1492
Ser Phe

TGAATTTGTT TTTCTTGTT TTAAAGTTAC CATTGCAATG TTGTGTCTTA AAATAAAAAT   1552

TTACATGAGA ATATAAAAAA AAAAAAAAAA AAAAAAAAAA AAAAAAAA               1600

(2) INFORMATION FOR SEQ ID NO: 38:

(i) SEQUENCE CHARACTERISTICS:
        (A) LENGTH:2276

(B) TYPE:nucleic acid (C) STRANDEDNESS:single (D) TOPOLOGY:linear (xi) SEQUENCE DESCRIPTION: SEQ ID NO: 38:

ATG GAT AAG ATT ACT GAT ATT CAG CTA AAA TTT GAT ACT                39
Met Asp Lys Ile Thr Asp Ile Gln Leu Lys Phe Asp Thr
1               5                   10

GGTAAGGTCC TTTTTAAAT AAACGTTCTC AACATTCTAA ATTTA                   84

GCG CCC TTT CCC GCA ATT ACA ATG TGC AAC TTG AAT CCA TAC AAA GAC    132
Ala Pro Phe Pro Ala Ile Thr Met Cys Asn Leu Asn Pro Tyr Lys Asp
    15                  20                  25

AGT CTT CTA AAA GAT GTT GAA GCG GTT AGA AAA ATT                    168
Ser Leu Leu Lys Asp Val Glu Ala Val Arg Lys Ile
30                  35                  40

GTAAGTATTT TTTGAAGTGT AATGCATTGC GTAGCAGCGG TTTTCAAGCT CAGCGTATAC  228

TCAAATGTGA TGGATCGCGC AGGCAAGTTC AACAGCAAG                         267

GAA GAC GAA ATT CGC AGA GTG GCA ACT CTT GAG ACC CGT AAG GCT CTA    315
Glu Asp Glu Ile Arg Arg Val Ala Thr Leu Glu Thr Arg Lys Ala Leu
                45                  50                  55

CAA ACC TCA GAT GTC ACG ACT ACA ATG TCC CCC GCA TCG CCA AGA ATC    363
Gln Thr Ser Asp Val Thr Thr Thr Met Ser Pro Ala Ser Pro Arg Ile
```

```
                     60                 65                 70
AGA CGA GAA TCG TCG AAA AGC ACT TCC TTT GAA CCT CGG TAC GCC GAT       411
Arg Arg Glu Ser Ser Lys Ser Thr Ser Phe Glu Pro Arg Tyr Ala Asp
         75                  80                  85

TGT ACC TGT AGT GGC CGA ATT ACC AGC ATG GAG TGT GAT ACA GAT GTA       459
Cys Thr Cys Ser Gly Arg Ile Thr Ser Met Glu Cys Asp Thr Asp Val
 90                  95                 100                 105

AAC AGC ACA CCG AAA TCT GAA GAA GAA ACA TGT TTA TGC GCG TTT GAT       507
Asn Ser Thr Pro Lys Ser Glu Glu Glu Thr Cys Leu Cys Ala Phe Asp
                 110                 115                 120

CGA GAT AGC GGC GAT GCT TGG CCA TGC TAC CCA AAA GAT AAA TGG GAA       555
Arg Asp Ser Gly Asp Ala Trp Pro Cys Tyr Pro Lys Asp Lys Trp Glu
             125                 130                 135

GAA CAC ACA TGT AAA TTT TGT GAT GAA CAC AAT GTC TGT ACT ATT GAC       603
Glu His Thr Cys Lys Phe Cys Asp Glu His Asn Val Cys Thr Ile Asp
             140                 145                 150

GAA AAA GCT GGC ATA CCT CCA GTA GCT ACG TTA TGT CTT TGC CAA ACT       651
Glu Lys Ala Gly Ile Pro Pro Val Ala Thr Leu Cys Leu Cys Gln Thr
         155                 160                 165

ATC AAT CCA TTC TGT GTT GCT TTC AAC AAA GAA TCG GCT ATA TTG AAG       699
Ile Asn Pro Phe Cys Val Ala Phe Asn Lys Glu Ser Ala Ile Leu Lys
170                 175                 180                 185

CTA TGG GAA TAC TAT GGA TCA GGA ATT CAT GAT CCG AAA GTT GTT GAA       747
Leu Trp Glu Tyr Tyr Gly Ser Gly Ile His Asp Pro Lys Val Val Glu
                 190                 195                 200

GCA TTG GGA TTT GCT                                                   762
Ala Leu Gly Phe Ala
             205

GTAAGTTTTA GTTCTCGCAC CGTTTTTCTA TTATGTTGTT TTAG                      806

AAT ATG AGC GAC GAA GTA GCT ATC GTC ACG AAA GCC AAG GAA AAC ATT       854
Asn Met Ser Asp Glu Val Ala Ile Val Thr Lys Ala Lys Glu Asn Ile
             210                 215                 220

ATT TTT GCT ATG TCA GCA CTT TCC ATA CAA CAA AGA ACA ATG TTA TCT       902
Ile Phe Ala Met Ser Ala Leu Ser Ile Gln Gln Arg Thr Met Leu Ser
         225                 230                 235

ATC CAA AAA CAT CAA CTG ATT CAA AAG TGC TCG TTT AAT GGA ATT GCT       950
Ile Gln Lys His Gln Leu Ile Gln Lys Cys Ser Phe Asn Gly Ile Ala
     240                 245                 250

TGT GAC ATT GAT AAG                                                   965
Cys Asp Ile Asp Lys
255

TAAGTTTAAA CCGATTCGAT TGCAAGTTCA AGAAAGGATG TTTTAGA                  1012

GAC TTT GAA ATC CTA GTA GAT CCA ACC TTT GGA AAT TGC TTC ACT TTC      1060
Asp Phe Glu Ile Leu Val Asp Pro Thr Phe Gly Asn Cys Phe Thr Phe
260                 265                 270                 275

AAC CAC AAT CGC ACC CAA ACA TTG AGC AGC ATT CGC GCA GGT CCC ATG      1108
Asn His Asn Arg Thr Gln Thr Leu Ser Ser Ile Arg Ala Gly Pro Met
                 280                 285                 290

TAC GGT TTA CGC ATG CTT ATT TTC GTC AAT GTA TCA GAA TAT TTG CCC      1156
Tyr Gly Leu Arg Met Leu Ile Phe Val Asn Val Ser Glu Tyr Leu Pro
             295                 300                 305

ACA ACA GAA GCA GTT GGT GTC AGA ATT ACG ATA CAC GAC AAA GAA GAC      1204
Thr Thr Glu Ala Val Gly Val Arg Ile Thr Ile His Asp Lys Glu Asp
         310                 315                 320

TAT CCA TTC CCG                                                      1216
Tyr Pro Phe Pro
    325

GTAATCAATT TCCTTCCATT AAGTCAACAA TGTCTTTCAA TTTGTTATTA CATTTTAATT    1276
```

```
                                                              -continued

TTCCCCAATG ACCTTTCAG                                              1295

GAC ACA TTT GGC TAC AGC GCA CCC ACT GGT TTT ATT TCC TCT TTT GGC   1343
Asp Thr Phe Gly Tyr Ser Ala Pro Thr Gly Phe Ile Ser Ser Phe Gly
    330                 335                 340

ATG CGA ATG ACC CGA ATG TCG CGC CTG CGC GCG TAT GGC GAT TGC ATT   1391
Met Arg Met Thr Arg Met Ser Arg Leu Arg Ala Tyr Gly Asp Cys Ile
345                 350                 355

CCC GAT GGG TTG ACC ACC AAT TAC ATT TAC AAG GGC TAC CGT TAC TCG   1439
Pro Asp Gly Leu Thr Thr Asn Tyr Ile Tyr Lys Gly Tyr Arg Tyr Ser
360                 365                 370                 375

ACA GAG                                                           1445
Thr Glu

GTAATAGTTC TATGATTAAG CCAATTGTCC AGTGACTCTT CAATTGAATG CTTTTAG    1502

GGT TGT TAT CGC ACA TGT TTT CAA GAA TTG GTA CTT AAT GAC TGC GGT   1550
Gly Cys Tyr Arg Thr Cys Phe Gln Glu Leu Val Leu Asn Asp Cys Gly
    380                 385                 390

TGC GGC GAT CCA CGC TTT CCC GTC TTA ACC AAT AAA TCA CAT TGT CAA   1598
Cys Gly Asp Pro Arg Phe Pro Val Leu Thr Asn Lys Ser His Cys Gln
395                 400                 405

GTG TTT GAT CCA GCT GCA CGT AAA TGT CTT GAG CAA CGG ACA AAT GAC   1646
Val Phe Asp Pro Ala Ala Arg Lys Cys Leu Glu Gln Arg Thr Asn Asp
410                 415                 420                 425

CTG AGC AAT GTT CAC GGG AGT TTT CGA TGT AGA TGC CAG CAG CCG TGT   1694
Leu Ser Asn Val His Gly Ser Phe Arg Cys Arg Cys Gln Gln Pro Cys
                430                 435                 440

GAC CAG TCT GTG TAC ACA GTT TCT TAT TCC GAA GCG AAT TGG CCA AGT   1742
Asp Gln Ser Val Tyr Thr Val Ser Tyr Ser Glu Ala Asn Trp Pro Ser
                445                 450                 455

ACT TCG TTG AAT ATT TCA CTG GGA AAC TGT GAT AAG GGG CCG GAT TTG   1790
Thr Ser Leu Asn Ile Ser Leu Gly Asn Cys Asp Lys Gly Pro Asp Leu
                460                 465                 470

TGC AAT GAA CAT TAC ATG                                           1808
Cys Asn Glu His Tyr Met
    475

TAAAACATTG AAAATGCCAA GTTACTGTTT CCACAAATTT AAATTTTAAG G          1859

GAA AAC GGC GCC ATG ATT GAA GTG TTC TAC GAA GCG TTG AAT TTC GAA   1907
Glu Asn Gly Ala Met Ile Glu Val Phe Tyr Glu Ala Leu Asn Phe Glu
480                 485                 490                 495

GTA TTT ACA GAA TCA GAA GCC TAT GGC                               1934
Val Phe Thr Glu Ser Glu Ala Tyr Gly
                    500

GTAAGTCACT CCTCTGTTAT CACAGTTAAT ATCATAAGCA CTTCAAACTT GCAG       1988

ATA GTC AAA ATG CTT GCC GAT TTC GGC GGC CAA CTT GGT CTC TGG TCA   2036
Ile Val Lys Met Leu Ala Asp Phe Gly Gly Gln Leu Gly Leu Trp Ser
505                 510                 515                 520

GGC GTA AGC TTC ATT ACT ATG TGC GAA TTC ACA TTT CTT GCT CTT GAA   2084
Gly Val Ser Phe Ile Thr Met Cys Glu Phe Thr Phe Leu Ala Leu Glu
                525                 530                 535

ATT ATC TAC ATG GTA TTT AAT CAT CAT TAC AAC ATT TAC AAA CGG AAA   2132
Ile Ile Tyr Met Val Phe Asn His His Tyr Asn Ile Tyr Lys Arg Lys
                540                 545                 550

AAA CAA GCC GAA GCA GAA GAG AAT GGC CTT                           2162
Lys Gln Ala Glu Ala Glu Glu Asn Gly Leu
555                 560

TAAACAATTG TATGCCACTC TGAGAGCAAA TGGATACGTG AATTGACATT TAATCAATTA 2222

ATTCAGTATG TTGTTGTATT GTTCAATGAA GGGCATTCGT TTATTCGCAC AAAT       2276
```

(2) INFORMATION FOR SEQ ID NO: 39:

(i) SEQUENCE CHARACTERISTICS:
        (A) LENGTH:36

(B) TYPE:nucleic acid (C) STRANDEDNESS:single (D) TOPOLOGY:linear (xi) SEQUENCE DESCRIPTION: SEQ ID NO: 39:

```
CATCGATGGA TCCCCNTTYC CNGAYACNTT YGGNTA                          36
```

(2) INFORMATION FOR SEQ ID NO: 40:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 40:

```
CGAATTCGGA TCCGGNACNG GRAAYCTNGG RTC                             33
```

(2) INFORMATION FOR SEQ ID NO: 41:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 41:

```
CGAATTCGGA TCCGGNACNG GRAANCGNGG RTC                             33
```

(2) INFORMATION FOR SEQ ID NO: 42:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 42:

```
GCGAATTCGG ATCCTCNGGN ACNGGRAANC KNG                             33
```

(2) INFORMATION FOR SEQ ID NO: 43:

(i) SEQUENCE CHARACTERISTICS:
        (A) LENGTH:34

(B) TYPE:nucleic acid (C) STRANDEDNESS:single (D) TOPOLOGY:linear (xi) SEQUENCE DESCRIPTION: SEQ ID NO: 43:

GCATCGATGG ATCCCCNTTY CCNGAYACNT TYGG                               34

(2) INFORMATION FOR SEQ ID NO: 44:

(i) SEQUENCE CHARACTERISTICS:
        (A) LENGTH:31

(B) TYPE:nucleic acid (C) STRANDEDNESS:single (D) TOPOLOGY:linear (xi) SEQUENCE DESCRIPTION: SEQ ID NO: 44:

GCATCGATGG ATCCCCNGAY ACNTTYGGNT A                                  31

(2) INFORMATION FOR SEQ ID NO: 45:

(i) SEQUENCE CHARACTERISTICS:
        (A) LENGTH:32

(B) TYPE:nucleic acid (C) STRANDEDNESS:single (D) TOPOLOGY:linear (xi) SEQUENCE DESCRIPTION: SEQ ID NO: 45:

GCGAATTCGG ATCCNACNGG RAAYCTNGGR TC                                 32

(2) INFORMATION FOR SEQ ID NO: 46:

(i) SEQUENCE CHARACTERISTICS:
        (A) LENGTH:32

(B) TYPE:nucleic acid (C) STRANDEDNESS:single (D) TOPOLOGY:linear (xi) SEQUENCE DESCRIPTION: SEQ ID NO: 46:

GCGAATTCGG ATCCNACNGG RAANCGNGGR TC                                 32

(2) INFORMATION FOR SEQ ID NO: 47:

(i) SEQUENCE CHARACTERISTICS:
        (A) LENGTH:34

(B) TYPE:nucleic acid (C) STRANDEDNESS:single (D) TOPOLOGY:linear (xi) SEQUENCE DESCRIPTION: SEQ ID NO: 47:

GCATCGATGG ATCCCCNGAY ACNTTYGGNT AYTC                               34

(2) INFORMATION FOR SEQ ID NO: 48:

(i) SEQUENCE CHARACTERISTICS:

(A) LENGTH:34

(B) TYPE:nucleic acid (C) STRANDEDNESS:single (D) TOPOLOGY:linear (xi) SEQUENCE DESCRIPTION: SEQ ID NO: 48:

GCATCGATGG ATCCCCNGAY ACNTTYGGNT AYAG					34

(2) INFORMATION FOR SEQ ID NO: 49:

(i) SEQUENCE CHARACTERISTICS:
        (A) LENGTH:35

(B) TYPE:nucleic acid (C) STRANDEDNESS:single (D) TOPOLOGY:linear (xi) SEQUENCE DESCRIPTION: SEQ ID NO: 49:

GCGAATTCGG ATCCNACNGG RAAYCTNGGR TCNCC					35

(2) INFORMATION FOR SEQ ID NO: 50:

(i) SEQUENCE CHARACTERISTICS:
        (A) LENGTH:35

(B) TYPE:nucleic acid (C) STRANDEDNESS:single (D) TOPOLOGY:linear (xi) SEQUENCE DESCRIPTION: SEQ ID NO: 50:

GCGAATTCGG ATCCNACNGG RAANCGNGGR TCNCC					35

(2) INFORMATION FOR SEQ ID NO: 51:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 51:

CATCGATGGA TCCGAYGARG TNGCNATHGT NAC					33

(2) INFORMATION FOR SEQ ID NO: 52:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 52:

```
CATCGATGGA TCCATHGTNA CNAARGCNAA RGA                               33
```

(2) INFORMATION FOR SEQ ID NO: 53:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 53:

```
CGAATTCGGA TCCCCRTACA TNGGNCCNGC NCG                               33
```

(2) INFORMATION FOR SEQ ID NO: 54:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 54:

```
CGAATTCGGA TCCCCRTACA TNGGNCCNGC YCT                               33
```

(2) INFORMATION FOR SEQ ID NO: 55:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 55:

```
CGAATTCGGA TCCACNTTYG GNTAYTCNGC NCC                               33
```

(2) INFORMATION FOR SEQ ID NO: 56:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 56:

```
CGAATTCGGA TCCACNTTYG GNTAYAGYGC NCC                               33
```

(2) INFORMATION FOR SEQ ID NO: 57:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 57:

CGAATTCGGA TCCGCNGART ANCCRAGNGT RTC                33

(2) INFORMATION FOR SEQ ID NO: 58:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 58:

CGAATTCGGA TCCGCNCTRT ANCCRAANGT RTC                33

(2) INFORMATION FOR SEQ ID NO: 59:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 59:

CATCGATGGA TCCTAAAGAT ACTCTTTGCA ATA                33

(2) INFORMATION FOR SEQ ID NO: 60:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 60:

CGAATTCGGA TCCTCCAACG TTTGGCAACT GTT                33

(2) INFORMATION FOR SEQ ID NO: 61:

(i) SEQUENCE CHARACTERISTICS:
        (A) LENGTH:30

(B) TYPE:nucleic acid (C) STRANDEDNESS:single (D) TOPOLOGY:linear (xi) SEQUENCE DESCRIPTION: SEQ ID NO: 61:

CCGAATTCTG CAGGCNGGNC CNATGTAYGG                    30

(2) INFORMATION FOR SEQ ID NO: 62:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 62:

AAGGATCCTG CAGGCNGART ANCCRAANGT RTC                                33

(2) INFORMATION FOR SEQ ID NO: 63:

(i) SEQUENCE CHARACTERISTICS:
        (A) LENGTH:33

(B) TYPE:nucleic acid (C) STRANDEDNESS:single (D) TOPOLOGY:linear (xi) SEQUENCE DESCRIPTION: SEQ ID NO: 63:

AAGGATCCTG CAGGCRCTRT ANCCRAANGT RTC                                33

(2) INFORMATION FOR SEQ ID NO: 64:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 64:

CCNTTYCCNG AYACNTTYGG                                               20

(2) INFORMATION FOR SEQ ID NO: 65:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 65:

ACNTTYGGNT AYTCNGCNCC                                               20

(2) INFORMATION FOR SEQ ID NO: 66:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 66:

ACNTTYGGNT AYAGYGCNCC                    20

(2) INFORMATION FOR SEQ ID NO: 67:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 67:

TTYCCNGAYA CNTTYGGNTA                    20

(2) INFORMATION FOR SEQ ID NO: 68:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 68:

CCNGAYACNT TYGGNTAYTC                    20

(2) INFORMATION FOR SEQ ID NO: 69:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 69:

CCNGAYACNT TYGGNTAYAG                    20

(2) INFORMATION FOR SEQ ID NO: 70:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 70:

GAYACNTTYG GNTAYTCNGC                    20

(2) INFORMATION FOR SEQ ID NO: 71:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 71:

GAYACNTTYG GNTAYAGYGC                    20

(2) INFORMATION FOR SEQ ID NO: 72:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 72:

ACNGGRAAYC TNGGRTCNCC                    20

(2) INFORMATION FOR SEQ ID NO: 73:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 73:

ACNGGRAANC GNGGRTCNCC                    20

(2) INFORMATION FOR SEQ ID NO: 74:

(i) SEQUENCE CHARACTERISTICS:
        (A) LENGTH:18

(B) TYPE:nucleic acid (C) STRANDEDNESS:single (D) TOPOLOGY:linear (xi) SEQUENCE DESCRIPTION: SEQ ID NO: 74:

GARCAYTAYA GYCCNGAR                      18

(2) INFORMATION FOR SEQ ID NO: 75:

(i) SEQUENCE CHARACTERISTICS:
        (A) LENGTH:18

(B) TYPE:nucleic acid (C) STRANDEDNESS:single (D) TOPOLOGY:linear (xi) SEQUENCE DESCRIPTION: SEQ ID NO: 75:

GARCAYTAYT CNCCNGAR                      18

(2) INFORMATION FOR SEQ ID NO: 76:

(i) SEQUENCE CHARACTERISTICS:
            (A) LENGTH:20

(B) TYPE:nucleic acid (C) STRANDEDNESS:single (D) TOPOLOGY:linear (xi) SEQUENCE DESCRIPTION: SEQ ID NO: 76:

TGYTAYAGYG CNCCNACNGG                                        20

(2) INFORMATION FOR SEQ ID NO: 77:

(i) SEQUENCE CHARACTERISTICS:
            (A) LENGTH:20

(B) TYPE:nucleic acid (C) STRANDEDNESS:single (D) TOPOLOGY:linear (xi) SEQUENCE DESCRIPTION: SEQ ID NO: 77:

TGYTAYTCNG CNCCNACNGG                                        20

(2) INFORMATION FOR SEQ ID NO: 78:

(i) SEQUENCE CHARACTERISTICS:
            (A) LENGTH:20

(B) TYPE:nucleic acid (C) STRANDEDNESS:single (D) TOPOLOGY:linear (xi) SEQUENCE DESCRIPTION: SEQ ID NO: 78:

GAYGARGTNG CNATHGTNAC                                        20

(2) INFORMATION FOR SEQ ID NO: 79:

(i) SEQUENCE CHARACTERISTICS:
            (A) LENGTH:20

(B) TYPE:nucleic acid (C) STRANDEDNESS:single (D) TOPOLOGY:linear (xi) SEQUENCE DESCRIPTION: SEQ ID NO: 79:

ATHGTNACNA ARGCNAARGA                                        20

(2) INFORMATION FOR SEQ ID NO: 80:

(i) SEQUENCE CHARACTERISTICS:
            (A) LENGTH:20

(B) TYPE:nucleic acid (C) STRANDEDNESS:single (D) TOPOLOGY:linear (xi) SEQUENCE DESCRIPTION: SEQ ID NO: 80:

CCRTACATNG GNCCNGCNCG                                           20

(2) INFORMATION FOR SEQ ID NO: 81:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 81:

CCRTACATNG GNCCNGCTCT                                           20

(2) INFORMATION FOR SEQ ID NO: 82:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 82:

TTYAAYCAYA AYAGRACNCA                                           20

(2) INFORMATION FOR SEQ ID NO: 83:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 83:

TTYAAYCAYA AYCGNACNCA                                           20

(2) INFORMATION FOR SEQ ID NO: 84:

(i) SEQUENCE CHARACTERISTICS:
        (A) LENGTH:20

(B) TYPE:nucleic acid (C) STRANDEDNESS:single (D) TOPOLOGY:linear (xi) SEQUENCE DESCRIPTION: SEQ ID NO: 84:

TGYTTYACNT TYAAYCAYAA                                           20

(2) INFORMATION FOR SEQ ID NO: 85:

(i) SEQUENCE CHARACTERISTICS:
        (A) LENGTH:23

(B) TYPE:nucleic acid (C) STRANDEDNESS: single (D) TOPOLOGY: linear (xi) SEQUENCE DESCRIPTION: SEQ ID NO: 85:

TGYTTYACNT TYAAYCAYAA YAG                                                    23

(2) INFORMATION FOR SEQ ID NO: 86:

(i) SEQUENCE CHARACTERISTICS:
        (A) LENGTH: 23

(B) TYPE: nucleic acid (C) STRANDEDNESS: single (D) TOPOLOGY: linear (xi) SEQUENCE DESCRIPTION: SEQ ID NO: 86:

TGYTTYACNT TYAAYCAYAA YCG                                                    23

(2) INFORMATION FOR SEQ ID NO: 87:

(i) SEQUENCE CHARACTERISTICS:
        (A) LENGTH: 18

(B) TYPE: nucleic acid (C) STRANDEDNESS: single (D) TOPOLOGY: linear (xi) SEQUENCE DESCRIPTION: SEQ ID NO: 87:

NGCYTCNGTN GTNGGCAT                                                          18

(2) INFORMATION FOR SEQ ID NO: 88:

(i) SEQUENCE CHARACTERISTICS:
        (A) LENGTH: 20

(B) TYPE: nucleic acid (C) STRANDEDNESS: single (D) TOPOLOGY: linear (xi) SEQUENCE DESCRIPTION: SEQ ID NO: 88:

GCNCCNTTYC CNGCNATAAC                                                        20

(2) INFORMATION FOR SEQ ID NO: 89:

(i) SEQUENCE CHARACTERISTICS:
        (A) LENGTH: 18

(B) TYPE: nucleic acid (C) STRANDEDNESS: single (D) TOPOLOGY: linear (xi) SEQUENCE DESCRIPTION: SEQ ID NO: 89:

TGYAAYCTNA AYCCNTAY                                                          18

(2) INFORMATION FOR SEQ ID NO: 90:

(i) SEQUENCE CHARACTERISTICS:
        (A) LENGTH:18

(B) TYPE:nucleic acid (C) STRANDEDNESS:single (D) TOPOLOGY:linear (xi) SEQUENCE DESCRIPTION: SEQ ID NO: 90:

```
TGYAAYTTYA AYCCNTAY                                                   18
```

(2) INFORMATION FOR SEQ ID NO: 91:

(i) SEQUENCE CHARACTERISTICS:
        (A) LENGTH:298

(B) TYPE:nucleic acid (C) STRANDEDNESS:single (D) TOPOLOGY:linear (xi) SEQUENCE DESCRIPTION: SEQ ID NO: 91:

```
TTT GGG TAT TCG GCA CCG ACA GGC TTT GTT TCG AGT TTT GGG TTG AAA       48
Phe Gly Tyr Ser Ala Pro Thr Gly Phe Val Ser Ser Phe Gly Leu Lys
 1               5                  10                  15

ACG                                                                   51
Thr

GTAAGCAATT ACACTTGTTT AACCTTTCGA AAAAAGGGTT TTCAG                      96

AAA GTG TTG CAT CGA CTA AAC GAA CCA TAT GGC ATG TGT AGT GAT ACC      144
Lys Val Leu His Arg Leu Asn Glu Pro Tyr Gly Met Cys Ser Asp Thr
        20                  25                  30

TTT CGG CCA GAA GGG TAC ATT TAT GCG GAA CAT TAC TCA CCT GAG          189
Phe Arg Pro Glu Gly Tyr Ile Tyr Ala Glu His Tyr Ser Pro Glu
            35                  40                  45

GTAATGTTTT GTTCAATTTG ACCTCTTTAA CATTGATTTT TGCAG                     234

GGT TGT TAT CGA AAC TGT TTC CAA CAC ATG ATT CTC GAC ACG TGT GGC      282
Gly Cys Tyr Arg Asn Cys Phe Gln His Met Ile Leu Asp Thr Cys Gly
     50                  55                  60

TGT GGC GAY CCC MGM                                                  297
Cys Gly Asp Pro Xaa
65

T                                                                    298
```

(2) INFORMATION FOR SEQ ID NO: 92:

(i) SEQUENCE CHARACTERISTICS:
        (A) LENGTH:930

(B) TYPE:nucleic acid (C) STRANDEDNESS:single (D) TOPOLOGY:linear (xi) SEQUENCE DESCRIPTION: SEQ ID NO: 92:

```
TTT GGG TAT AGT GCT CCA ACA GGC TTT ATT TCC TCC TTC GGT CTC AAA       48
Phe Gly Tyr Ser Ala Pro Thr Gly Phe Ile Ser Ser Phe Gly Leu Lys
 1               5                  10                  15
```

```
ACG                                                                  51
Thr

GTAAGTCTTT TGAGAAGAGG GCACTTCGGA TNTTCGTCGA CTTTGTAATG CGATGGTCCA   111

AATCAGACGA TAATCCCAAT CACTTCGACT AGAATGTATT TGTTGCTTTT TGAAGCGTCA   171

GSTTTCAGTG TTGTTCCACA GCTAGCTTCA GTTACTATCA ACATGAAGCC AAGAAGCTAA   231

TTGTACCTCT TACTCTCCAA CTGGATATTA CTTTTATGTC AGTCTAGAAA TATTAACTGT   291

ATAGAGCCTG CATAATAACA CAGTAGAAGA CTGTWWSKGC CATCTCATAA CTCCTTCCCA   351

CCAACTTCAT TGATTTTCCC GTTATGCCTA TACCGAAATC AAAACATTTT AAG         404

AAG GTG CTT CAT CGC CTC GAC GCT CCA TAC GGT CTT TGC AGC GAT ACG    452
Lys Val Leu His Arg Leu Asp Ala Pro Tyr Gly Leu Cys Ser Asp Thr
            20                  25                  30

TTC AGG CCA GAA GGG TAC ATC TAT CAG GAA CAC TAC TCA CCC GAG        497
Phe Arg Pro Glu Gly Tyr Ile Tyr Gln Glu His Tyr Ser Pro Glu
        35                  40                  45

GTGAATTCGA GTTCTTTTGA TGGCAAAATT CAGAGAAGCC ATCGTGCTTA GGTACCTAAG   557

TTGTGCTCGC TTTCATTTGT GGTATTTGAT GAGTCGAAAA TTGACTGCCC AGTTTTGTTT   617

CAAACGGTGG CCATTTCTTT GTTCGTAACC AGCGCAAACT TTTAAATCTA CAAGGCGCTT   677

CTACAGGATT TCATTGCTCA TGTTTCGGCT CTCTGAGTGG GGCATTGCAA ACCACTGGT    737

TCAAAAGGAA CATTTTTTGG GAAGGGAGGG GYGAATNTAA ACTTCAATAT GAGTACAAAT   797

TTAAGCAGGT GATACTACAA TGGTGCTTTG ATATCAATGA GAAAAAACCA GGAATTTCAG   857

GGT TGT TAT CGC AAC TGT TTT CAA CAT ATG GTT CTT GCT CAA TGC GGC    905
Gly Cys Tyr Arg Asn Cys Phe Gln His Met Val Leu Ala Gln Cys Gly
            50                  55                  60

TGT GGC GAC CCC CGC TTC CCC GTC                                    929
Cys Gly Asp Pro Arg Phe Pro Val
65                  70

G                                                                  930

(2) INFORMATION FOR SEQ ID NO: 93:

(i) SEQUENCE CHARACTERISTICS:
        (A) LENGTH:305

(B) TYPE:nucleic acid (C) STRANDEDNESS:single (D) TOPOLOGY:linear (xi) SEQUENCE DESCRIPTION: SEQ ID NO: 93:

TTC GGG TAT AGT GCT CCA ACT GGA TTC ATT TCT TCA TTT GGT CTT AAA    48
Phe Gly Tyr Ser Ala Pro Thr Gly Phe Ile Ser Ser Phe Gly Leu Lys
 1               5                  10                  15

ACG                                                                51
Thr

GTATTTAAAT ACCCTTGAGA ATCTGTTTGC AGAGTTCGAT TTCAG                   96

AAA GAA CTA CAT CGT CTC AGT GCT CCA TGG GGG AAT TGC AGT GAC ACA    144
Lys Glu Leu His Arg Leu Ser Ala Pro Trp Gly Asn Cys Ser Asp Thr
            20                  25                  30

TTC CGA CCG GTT CCA TAC ATT TAC AAC GAA CAC TAT TCT CCT GAA        189
Phe Arg Pro Val Pro Tyr Ile Tyr Asn Glu His Tyr Ser Pro Glu
        35                  40                  45

GTATGTAACA TTTCCCATTC TTAATCAAAC ATTTATATTT TCAG                    233
```

```
GGT TGC CAT CGA AAT TGT TTC CAA TTG AAA GTA CTT GAA ATA TGT GGA         281
Gly Cys His Arg Asn Cys Phe Gln Leu Lys Val Leu Glu Ile Cys Gly
    50                  55                  60

TGT GGC GAT CCT AGG TTC CCC GCT                                         305
Cys Gly Asp Pro Arg Phe Pro Ala
65                  70
```

(2) INFORMATION FOR SEQ ID NO: 94:

(i) SEQUENCE CHARACTERISTICS:
        (A) LENGTH:2400

(B) TYPE:nucleic acid (C) STRANDEDNESS:single (D) TOPOLOGY:linear (xi) SEQUENCE DESCRIPTION: SEQ ID NO: 94:

```
AA ATG CAA CTT AAA TTC GAG CCA GCT CCA TTC CCT GCT GCT ACC GTA          47
   Met Gln Leu Lys Phe Glu Pro Ala Pro Phe Pro Ala Ala Thr Val
   1               5                   10                  15

TGC AAT TTG AAT GCA TTC AAG GCC AGT CAG                                 77
Cys Asn Leu Asn Ala Phe Lys Ala Ser Gln
                20                  25

TTGAAGCAGT ACGAGGAAAT CGAACAGGGT GTACGTTCGA ATGCCAATAT ATTTGTCTTT       137

TATTGCCTTT GATCAAAAAT TTCAGTTCCA AGTCTGGGAG CGCGCTATGA ATACAATAGA       197

CCAAACTCAA CTAAATCCGA ATTCCCATCC GTCGAAAAAG ACACGTAATG TATGAGCCTG       257

TCTACGTAAG A                                                            268

TGC GTC TGT AAC TTA CCT GAT GAC CAA TGT GTG CCA CAA CGC AAC CCC         316
Cys Val Cys Asn Leu Pro Asp Asp Gln Cys Val Pro Gln Arg Asn Pro
                30                  35                  40

CTC ACG AAA AAC ACT TCT GTT TGC ATG TGT TTC GAA GAT GCA ACA ACA         364
Leu Thr Lys Asn Thr Ser Val Cys Met Cys Phe Glu Asp Ala Thr Thr
                    45                  50                  55

GGC GAT ATT TGG CCA TGC TAT CCA ACG ACT GTT TGG AAT GAA AAG             409
Gly Asp Ile Trp Pro Cys Tyr Pro Thr Thr Val Trp Asn Glu Lys
    60                  65                  70

GTTTGTACAC TCCCATTTTT CATTACAAAA ACTAACTTTT TTCCTGTACT CGTACTCGTA       469

TTTTTTGCTA TTTTTTACAT AATTTTTTCT TTAACCCATT CGTGAACGTC CTTCAAGCTC       529

AATTTGTCAA ATCCAATTCT CAAAAGGGCC AAAAACGCAT TCAAATGATA AATTAGTGGC       589

CGCAGTGTCA AAGCTCTGTG GAAGCATCCA TTTGAATCGA TGTCCAGAGC CATTGCATTG       649

TGTCTTTAAA GACAACCGTC ACTCGGGTGG CCATAGCGGG ATGTCTGGCA GTAACTTTTA       709

AAGTAATTAG TTGCATTGCA AACAAAACAA TACATNTTCA G                           750

ACA TGT TAT CAT TGT TCA AAG TCA AAC ACG TGT GAT GAC CCT GAT AGA         798
Thr Cys Tyr His Cys Ser Lys Ser Asn Thr Cys Asp Asp Pro Asp Arg
    75                  80                  85

CCG CCA AAT ATT ACG AGT TTA CTG ACT GAG CCT AAG GCT ACA CCA TGC         846
Pro Pro Asn Ile Thr Ser Leu Leu Thr Glu Pro Lys Ala Thr Pro Cys
    90                  95                  100

CTG TGT CAA AGT GTA TCG CAC TAT TGC GTC ATG AAA CCA ACT GAG GAT         894
Leu Cys Gln Ser Val Ser His Tyr Cys Val Met Lys Pro Thr Glu Asp
105                 110                 115                 120

GTA AAG TGG                                                             903
Val Lys Cys

TGGAATCCAA ACAACTATAC AGTCTTCCCA GTGACCGCTC CACCAACACG TCACCGGAAA       963
```

```
TTGAAAGC                                                                        971

GCT TTT GGG TTA GCA GAT CTG CGC GAT CGT GGT GCA ATT ACA ACA AAA               1019
Ala Phe Gly Leu Ala Asp Leu Arg Asp Arg Gly Ala Ile Thr Thr Lys
    125                 130                 135

ACA AAA GAA AAT TTG ATT TTC TTA GTT GCT GCA ATG CCG ATG GAA ACT               1067
Thr Lys Glu Asn Leu Ile Phe Leu Val Ala Ala Met Pro Met Glu Thr
140                 145                 150                 155

CGA AGA CAG TTG TCG TAT ACG TTG GAT GAG TTT GTA CTA CGA TGT TCA               1115
Arg Arg Gln Leu Ser Tyr Thr Leu Asp Glu Phe Val Leu Arg Cys Ser
                160                 165                 170

TTC AAC AGT GAA GAT TGC GAT CTT CGA CGG GAC TTT CAC ATT CAC ATG               1163
Phe Asn Ser Glu Asp Cys Asp Leu Arg Arg Asp Phe His Ile His Met
            175                 180                 185

GAT CCT GAG TTT GGA AAT TGT TAC ACC TTC AAT TTC AAT GAT TCA GTT               1211
Asp Pro Glu Phe Gly Asn Cys Tyr Thr Phe Asn Phe Asn Asp Ser Val
        190                 195                 200

GAG TTG AAG AAC AGT CGA GCC GGT CCC ATG TAT GGT TTG CGA TTA CTG               1259
Glu Leu Lys Asn Ser Arg Ala Gly Pro Met Tyr Gly Leu Arg Leu Leu
    205                 210                 215

TTG AAT GTT AAT CAG AGT GAC TAC ATG CCG ACA ACA GAA GCT GCT GGT               1307
Leu Asn Val Asn Gln Ser Asp Tyr Met Pro Thr Thr Glu Ala Ala Gly
220                 225                 230                 235

GTG CGG TTG GTT GTT CAT GAA CAG GAT CAG GAA CCT TTT CCG GAC ACA               1355
Val Arg Leu Val Val His Glu Gln Asp Gln Glu Pro Phe Pro Asp Thr
                240                 245                 250

TTT GGT TAT TCG GCA CCG ACA GGC TTT GTT TCG AGT TTT GGG TTG AAA               1403
Phe Gly Tyr Ser Ala Pro Thr Gly Phe Val Ser Ser Phe Gly Leu Lys
            255                 260                 265

ACG                                                                            1406
Thr

GTAAGCAATT ACACTTGTTT AACCTTTCGA AAAAAGGGTT TTCAG                              1451

AAA GTG TTG CAT CGA CTA AAC GAA CCA TAT GGC ATG TGT AGT GAT ACT               1499
Lys Val Leu His Arg Leu Asn Glu Pro Tyr Gly Met Cys Ser Asp Thr
    270                 275                 280

TTC GGC CCA GAA GGG TAC ATT TAT GCG GAA CAT TAC TCA CCT GAG                   1544
Phe Gly Pro Glu Gly Tyr Ile Tyr Ala Glu His Tyr Ser Pro Glu
285                 290                 295

GTAATGTTTT GTTCAATTTG ACCTCTTTAA CATTGATTTT TGCAG                              1589

GGT TGT TAT CGA AAC TGT TTC CAA CAC ATG ATT CTC GAC ACG TGT GGC               1637
Gly Cys Tyr Arg Asn Cys Phe Gln His Met Ile Leu Asp Thr Cys Gly
300                 305                 310                 315

TGT GGT GAC CCT CGG TTC CCC TTA CCT TCT GAC AAG GAA AAA CCC TGC               1685
Cys Gly Asp Pro Arg Phe Pro Leu Pro Ser Asp Lys Glu Lys Pro Cys
                320                 325                 330

GAC GCC CGA AAT GCC CGT GAG CGA ACT TGT TTA ACT AAT TTG ACC ACC               1733
Asp Ala Arg Asn Ala Arg Glu Arg Thr Cys Leu Thr Asn Leu Thr Thr
            335                 340                 345

ATC CTC GGC GGA TTC CAC CAT CTC CAA CAT GAT TGC CAC TGT GTT CAA               1781
Ile Leu Gly Gly Phe His His Leu Gln His Asp Cys His Cys Val Gln
        350                 355                 360

CCA TGT ACG GAA AAT GTC TTT GAA ACG GCG TAT TCA GCA GCT GCA TGG               1829
Pro Cys Thr Glu Asn Val Phe Glu Thr Ala Tyr Ser Ala Ala Ala Trp
    365                 370                 375

CCT GCA ATT AAC TTT AAT ATT GGC GCA GAC TGT CCA GCA GTA TAC CAC               1877
Pro Ala Ile Asn Phe Asn Ile Gly Ala Asp Cys Pro Ala Val Tyr His
380                 385                 390                 395

ATA TCT AAT GAT TCA AAA GCT TGT GCA GAA TAT TAC CGG                           1916
```

```
Ile Ser Asn Asp Ser Lys Ala Cys Ala Glu Tyr Tyr Arg
            400                 405

TAACTTGTCG TTTCCAACAA CTTTTTATGT TTTAATATGC TTAATATGTC TGCTTTTTTA    1976

GA                                                                   1978

CTT AAC ACA GCC TAT ATT GAA ATC TAT TAC GAA CAA CTC AAC TTT GAA     2026
Leu Asn Thr Ala Tyr Ile Glu Ile Tyr Tyr Glu Gln Leu Asn Phe Glu
    410                 415                 420

ACA TTA AAA GAA ACT GCT GGT TAT ACT                                  2053
Thr Leu Lys Glu Thr Ala Gly Tyr Thr
425                 430

GTACGTTTAT TACATATAGC TTTCCAAGAC AAACAAAACC CATGTTTTAG               2103

CTT GTC AAC CTT TTC TCC GAT TTC GGT GGT AAC ATT GGT CTC TGG ATT     2151
Leu Val Asn Leu Phe Ser Asp Phe Gly Gly Asn Ile Gly Leu Trp Ile
        435                 440                 445

GGT TTC TCT GTA ATT ACA ATG TTT GAA GTG GTT GAA GTC TTA TGT GAA     2199
Gly Phe Ser Val Ile Thr Met Phe Glu Val Val Glu Val Leu Cys Glu
450                 455                 460                 465

ATC ATT ATT TAT ATC GGT ACG CAT TCG CTT TTT AAG CTC TTC ATA TCT     2247
Ile Ile Ile Tyr Ile Gly Thr His Ser Leu Phe Lys Leu Phe Ile Ser
                470                 475                 480

AAA TTA CTA CCT TCC CAG GAA AAC AAC CAC ACC GCA TTT ATC AAC GAA     2295
Lys Leu Leu Pro Ser Gln Glu Asn Asn His Thr Ala Phe Ile Asn Glu
                485                 490                 495

AGC GCA GAA AGA ATC GCC AAA ACG AGA ATG AAA                          2328
Ser Ala Glu Arg Ile Ala Lys Thr Arg Met Lys
            500                 505

TGAATGAACT TCCTCCAACG ATAATCGAAC AAAGAGAGAA GAAAGTATCG ACTCGACATT   2388

CGGAAAGCTC AG                                                       2400

(2) INFORMATION FOR SEQ ID NO: 95:

(i) SEQUENCE CHARACTERISTICS:
        (A) LENGTH:1100

(B) TYPE:nucleic acid (C) STRANDEDNESS:single (D) TOPOLOGY:linear (xi) SEQUENCE DESCRIPTION: SEQ ID NO: 95:

TTCCAG                                                                  6

AAC ATG AGC GAT GAG GTG GCC ATT GTA ACG AAG GCA AAG GAA AAT CTC       54
Asn Met Ser Asp Glu Val Ala Ile Val Thr Lys Ala Lys Glu Asn Leu
 1               5                  10                  15

ATA TTT GCG ATG TCT GAG TTA TCA AAG GCT CAA CGT ATC GCG CTC TCT     102
Ile Phe Ala Met Ser Glu Leu Ser Lys Ala Gln Arg Ile Ala Leu Ser
            20                  25                  30

GCT CAA AAA AGA CAA CTC ATT CAA AAA TGT TCA TTC AAC GGC GCT GAA     150
Ala Gln Lys Arg Gln Leu Ile Gln Lys Cys Ser Phe Asn Gly Ala Glu
        35                  40                  45

TGT AAC ATC GAG AAG                                                  165
Cys Asn Ile Glu Lys
     50

TTGGTTCACT CTTCCCTTGA ATAAGGAACT TTTGTTTTTG GATTTCCTTT TCAATGAAGC    225

ATATGCAACA TAAGCGGAGC GCCATTTATT TTCGAATGCA TAAARRGAGC AAAGTGAGAT    285

ATTGGAAAGA GCATTTTTAT GCTTTTTATC CTGTTGGATG GGATGATCAG CGAAGAAGAA    345
```

```
TTTAGACACA AATGTGCAAA AGTGTCCAAA ACGCACGACT TCAAGAAGCA GKGTAGAGRA      405

GGTGGAATGA GTAGGGATAT GTGATCATAA CTCTCTTCGC GCCTCTGCTC AACGTGCCAC      465

TTATTGATCA ATACCGTAAA GAAGCATTGT CGTCGATGCT GGATATGCCA CTATTYAGTG      525

TAAAAGCCAA ATATATTTTT AATTTTTTAG TCAGAAAATC AAGCCCTTGA AGCAACCGAG      585

GAAAATAGAT AGGACTCTAC CAGCTTCATG CGAATTCTTT ATTCCTTTTC TGTTTCAGGG      645

ATTGTAATTG AATCTAAAAT AGCTAAAATG CTTAACCCTT GAGGAAGGAG CTCATTTAGG      705

TCTAGCTCTG ACTCCAGTGA TATAGTCATG TGTAATGACA GGAGAAAACT GCAGCAAGTG      765

GACTCAATTC TATAATAAAA GCAGAGGATC GAGAGTTCAA ATCCGTCGCC ATAGACGATG      825

AGACTGCAGT GTAATGATGA AGATTTTTTG GCTATCAGAT TTTGTAACGA AAGTTTCTTG      885

CACGAGGGCG ACATTATAAA TAGTTGCACG CAAGGATTTA TTGTTGAGTT GTGGACGTAA      945

AGCAGTTAAA TTTGCAGA                                                    963

GAC TTC CTT GTT GTT GCC GAT CCA ACG TTT GGC AAC TGT TTC ACA TTC       1011
Asp Phe Leu Val Val Ala Asp Pro Thr Phe Gly Asn Cys Phe Thr Phe
             55                  60                  65

AAC CAC AAT CGA ACA GAG AAT AAA AGT AGC ATT CGC GCT GGT CCA ATG       1059
Asn His Asn Arg Thr Glu Asn Lys Ser Ser Ile Arg Ala Gly Pro Met
 70                  75                  80                  85

TAT                                                                   1062
Tyr

GGTTAGCGCC CTTAAATCAG CATATTATTG ATGAGGAT                             1100

(2) INFORMATION FOR SEQ ID NO: 96:

(i) SEQUENCE CHARACTERISTICS:
        (A) LENGTH:1614

(B) TYPE:nucleic acid (C) STRANDEDNESS:single (D) TOPOLOGY:linear (xi) SEQUENCE DESCRIPTION: SEQ ID NO: 96:

ACA TAT TTG AAA GAT CAA AAC ATT TTT ACG GAA GAC CAT CTA GAC CTC        48
Thr Tyr Leu Lys Asp Gln Asn Ile Phe Thr Glu Asp His Leu Asp Leu
 1               5                  10                  15

ATA AGC TCT ATG CCT ACT CGA CCA GAA AGG ATT GCT CAG TTT CTA CGA        96
Ile Ser Ser Met Pro Thr Arg Pro Glu Arg Ile Ala Gln Phe Leu Arg
             20                  25                  30

GCT TAT CGA AAA CAA GCT TCA GCT TTG GCA CCA CTC ATC GAC TTC TTT       144
Ala Tyr Arg Lys Gln Ala Ser Ala Leu Ala Pro Leu Ile Asp Phe Phe
         35                  40                  45

GTC TAC AAT AGT CAA TTT CAT TTG TCA GAT TTC TTT GAA GAA CGC CTA       192
Val Tyr Asn Ser Gln Phe His Leu Ser Asp Phe Phe Glu Glu Arg Leu
     50                  55                  60

AGT ACC GCA ATT GAG AAT CCC GAG TTG TTA CGG TCG GTA TTG ATA TCT       240
Ser Thr Ala Ile Glu Asn Pro Glu Leu Leu Arg Ser Val Leu Ile Ser
 65                  70                  75                  80

CCC ATT TTT GGA AAA CAA ATG CTG GAA CGA AAA CTG TTA TTG GGG AAC       288
Pro Ile Phe Gly Lys Gln Met Leu Glu Arg Lys Leu Leu Leu Gly Asn
             85                  90                  95

GTT CCG AAA CAA ATG GAT TGT TAC TGT AGA GCA TAT AAC GTT GAA GGG       336
Val Pro Lys Gln Met Asp Cys Tyr Cys Arg Ala Tyr Asn Val Glu Gly
        100                 105                 110
```

```
RTT ATC GAA AAG TTG AGC GAT ATG TGT AAT CTC GGT TCC TTT TTT CTG      384
Xaa Ile Glu Lys Leu Ser Asp Met Cys Asn Leu Gly Ser Phe Phe Leu
        115                 120                 125

TTC CTT CAT GGT CGA GCT GGA TCC GGA AAA TCG GTC ATA GCA TCT CAA      432
Phe Leu His Gly Arg Ala Gly Ser Gly Lys Ser Val Ile Ala Ser Gln
    130                 135                 140

GCG TTA TCG ATA TCG GAT CAA CTT ATT GGC ATA TGC TAC GAC TCG GTT      480
Ala Leu Ser Ile Ser Asp Gln Leu Ile Gly Ile Cys Tyr Asp Ser Val
145                 150                 155                 160

GTA TGG CTA AAG GAT AGC GGT ACC ACA TCG AAA TCT ACA TTC GAC TTG      528
Val Trp Leu Lys Asp Ser Gly Thr Thr Ser Lys Ser Thr Phe Asp Leu
                165                 170                 175

TTC ACA GAT CTG CTT CTC ATG TTG AAG AGC GAA GAA GAT CTT CTG AAG      576
Phe Thr Asp Leu Leu Leu Met Leu Lys Ser Glu Glu Asp Leu Leu Lys
            180                 185                 190

TTC CCT TCT GTC GAA CAC TTA ACA TCA GTT GTT CTC AAG CGA ATG TTG      624
Phe Pro Ser Val Glu His Leu Thr Ser Val Val Leu Lys Arg Met Leu
        195                 200                 205

GCC AGT GCT CTG ATT GAA AGA CCA AAC ACT CTA TTC GTC TTC GAT GAT      672
Ala Ser Ala Leu Ile Glu Arg Pro Asn Thr Leu Phe Val Phe Asp Asp
    210                 215                 220

GTA GTT CAA GAG GAG ACG ATA CGC TGG GCT CAA GAA CTC CGT CTA CGA      720
Val Val Gln Glu Glu Thr Ile Arg Trp Ala Gln Glu Leu Arg Leu Arg
225                 230                 235                 240

TGT CTT GTA ACA ACT CGA GAC GTG GAA ATT TCT AAT GTT GCC TCA TCA      768
Cys Leu Val Thr Thr Arg Asp Val Glu Ile Ser Asn Val Ala Ser Ser
                245                 250                 255

ACA TGC GAT TTT GTC GAG GTT ACA TCT CTG GAA GAC GAC GAG TGC TAC      816
Thr Cys Asp Phe Val Glu Val Thr Ser Leu Glu Asp Asp Glu Cys Tyr
            260                 265                 270

GAT ATG TTG GAA GCA TAT GGG ATG CCT ATG CCC ATT GAT CAA AGA GAA      864
Asp Met Leu Glu Ala Tyr Gly Met Pro Met Pro Ile Asp Gln Arg Glu
        275                 280                 285

GAA GAC ATA TTA AGT AAG ACA CTG AAG TTG ACT AGT GGA AAT CCG GCT      912
Glu Asp Ile Leu Ser Lys Thr Leu Lys Leu Thr Ser Gly Asn Pro Ala
    290                 295                 300

GCT TTG ATG ATG GTG TTC AAA TCG TGC GAG CCA AAA ACT TTC GAT AAA      960
Ala Leu Met Met Val Phe Lys Ser Cys Glu Pro Lys Thr Phe Asp Lys
305                 310                 315                 320

ATG GCA CAG CTG AAC AAC AAA CTG GAA ACA CGT GGA CTG TTA GGA ATA     1008
Met Ala Gln Leu Asn Asn Lys Leu Glu Thr Arg Gly Leu Leu Gly Ile
                325                 330                 335

GAA TGC GTG ACA CCG TAT TGC TAC ACT TCA ATC TCA AAG GCC CTT CAG     1056
Glu Cys Val Thr Pro Tyr Cys Tyr Thr Ser Ile Ser Lys Ala Leu Gln
            340                 345                 350

CGA TGT GTT GAA GTT CTG TCT GAT GAA GAC CGT AAT GCT CTG GCA CTC     1104
Arg Cys Val Glu Val Leu Ser Asp Glu Asp Arg Asn Ala Leu Ala Leu
        355                 360                 365

GCT GTC ATT ATG CCG CCT GAA GTC GAT ATA CCT CTG AAG ATA TGG TCG     1152
Ala Val Ile Met Pro Pro Glu Val Asp Ile Pro Leu Lys Ile Trp Ser
    370                 375                 380

CTT GTT ATT CCA GTA AAT ATA TGT TCA AAC GAG GCA GAG TTG TTA GAT     1200
Leu Val Ile Pro Val Asn Ile Cys Ser Asn Glu Ala Glu Leu Leu Asp
385                 390                 395                 400

AAT GAA GTT GCA GAT CGA TTG AAA CGG TTG ACT AAA CGT GGT GCG CTT     1248
Asn Glu Val Ala Asp Arg Leu Lys Arg Leu Thr Lys Arg Gly Ala Leu
                405                 410                 415

CTT AGT GGG AAA CGA GCA CCG GCG TTA ACA TTC AAA ATC GAC CAT ATC     1296
Leu Ser Gly Lys Arg Ala Pro Ala Leu Thr Phe Lys Ile Asp His Ile
            420                 425                 430
```

```
ATT CAC ATT TTC TTG AAG CAT GTT GTT GAT ACT CAA ACT ATT GCA TGT        1344
Ile His Ile Phe Leu Lys His Val Val Asp Thr Gln Thr Ile Ala Cys
        435                 440                 445

GGT ATC GCG ATG CTC GAA CAG AAC CTT CGT GAG ATT AAC AAC AAC GTA        1392
Gly Ile Ala Met Leu Glu Gln Asn Leu Arg Glu Ile Asn Asn Asn Val
        450                 455                 460

GCT TCC CCA GAA CGA AAT TTA CCC CCA CAT CAT CAG AAA TTC AGG CGC        1440
Ala Ser Pro Glu Arg Asn Leu Pro Pro His His Gln Lys Phe Arg Arg
465                 470                 475                 480

ATA TCT GCA AGT GNN ATG TAT CCG ATT TCA GAT GAA CAA GTC ATT CGT        1488
Ile Ser Ala Ser Xaa Met Tyr Pro Ile Ser Asp Glu Gln Val Ile Arg
                485                 490                 495

CCT GAA GAT TAC CAT AAA TTT ATG ATA ATT CAC AGC CAG TTC TAT GAA        1536
Pro Glu Asp Tyr His Lys Phe Met Ile Ile His Ser Gln Phe Tyr Glu
                500                 505                 510

TCG CTT AAG AAG TTT GTT TCT TCC                                        1560
Ser Leu Lys Lys Phe Val Ser Ser
                515             520

TAAATAGCCA TGTATATTTC ATCCTGTTAT TTTGTCTAGA TTATCTGCAT GTCT            1614

(2) INFORMATION FOR SEQ ID NO: 97:

(i) SEQUENCE CHARACTERISTICS:
        (A) LENGTH:977

(B) TYPE:nucleic acid (C) STRANDEDNESS:single (D) TOPOLOGY:linear (xi) SEQUENCE DESCRIPTION: SEQ ID NO: 97:

CT GCA GAT TTT GAG CCG CGR TAT CCG ACA TAT TTA GAA GCT CTA ATG        47
     Ala Asp Phe Glu Pro Arg Tyr Pro Thr Tyr Leu Glu Ala Leu Met
     1               5                   10                  15

ATT TTT TCT GAA GAC CAT ACC GAC CAA ATC AAA GCC ATG ACT ACT CGA        95
Ile Phe Ser Glu Asp His Thr Asp Gln Ile Lys Ala Met Thr Thr Arg
                20                  25                  30

TGC GGA AGA ATA GCT GAA TTT CTT CGG TCA TAC AGG AGA CAA GCT TCC       143
Cys Gly Arg Ile Ala Glu Phe Leu Arg Ser Tyr Arg Arg Gln Ala Ser
                35                  40                  45

GAA TTG GCT CCA TTA ATT GAG TTT TTC AAA TAT AAT CAT CAA ACT CAT       191
Glu Leu Ala Pro Leu Ile Glu Phe Phe Lys Tyr Asn His Gln Thr His
        50                  55                  60

CTA TCG GAC TTT TTC GAG AAT TAC ATA GAA GAA GCG ATT CAC CAC CCC       239
Leu Ser Asp Phe Phe Glu Asn Tyr Ile Glu Glu Ala Ile His His Pro
65                  70                  75

GAA CTG TTA GAC TCG AGA CTA ATT TCC ATG TTT GAG AGA CAA AAA TTG       287
Glu Leu Leu Asp Ser Arg Leu Ile Ser Met Phe Glu Arg Gln Lys Leu
80                  80                  90                  95

GAT CGG AAA CTT TTA TCT GGA AAT GTT CCC AGA CAG ATG GAT GCG TTC       335
Asp Arg Lys Leu Leu Ser Gly Asn Val Pro Arg Gln Met Asp Ala Phe
                100                 105                 110

TGT CGT GAT TAC CAC GTT AAA CAA GTT ATT GGA AAA TTG GAG GCT TTG       383
Cys Arg Asp Tyr His Val Lys Gln Val Ile Gly Lys Leu Glu Ala Leu
                115                 120                 125

GGG AAT TTA GAT TCG TTT TTT CTT TTT CTT CAT GGC CGT GCA GGA TCC       431
Gly Asn Leu Asp Ser Phe Phe Leu Phe Leu His Gly Arg Ala Gly Ser
        130                 135                 140

GGA AAA TCA GTA ATT GCA CCT CAA GCT CTG TCT AGA TCT GAT CAT CTT       479
```

```
Gly Lys Ser Val Ile Ala Pro Gln Ala Leu Ser Arg Ser Asp His Leu
    145                 150                 155

TTC GCA GTA AGT TAT GAC TCA GTT GTG TGG CTT AAG GAC AGC GGT ACA      527
Phe Ala Val Ser Tyr Asp Ser Val Val Trp Leu Lys Asp Ser Gly Thr
160                 165                 170                 175

ACG GCG AAA TCT ACA TTT GAC TTG TTT ACT GRT CTT TTG TTG ATG TTG      575
Thr Ala Lys Ser Thr Phe Asp Leu Phe Thr Xaa Leu Leu Leu Met Leu
                180                 185                 190

AAA AGC GAA GAC GAC CTC CTC AAC TTC CCA TCA GTG GAA CGC GTA ACA      623
Lys Ser Glu Asp Asp Leu Leu Asn Phe Pro Ser Val Glu Arg Val Thr
            195                 200                 205

TCA GTT GTA CTC AAA AGA ATG ATC GTC AAC GCT TTG ATY GAT AGA CCA      671
Ser Val Val Leu Lys Arg Met Ile Val Asn Ala Leu Ile Asp Arg Pro
        210                 215                 220

AAC ACT CTA TTC GTC TTT GAC GAT GTA GTT CAA GAG GAG ACG ATA CGT      719
Asn Thr Leu Phe Val Phe Asp Asp Val Val Gln Glu Glu Thr Ile Arg
    225                 230                 235

TGG GCT CAA GAA CTC CGT CTA CGG TGT CTC GTA ACT ACC AGG GAT GTA      767
Trp Ala Gln Glu Leu Arg Leu Arg Cys Leu Val Thr Thr Arg Asp Val
240                 245                 250                 255

GAA ATA TGC AAC GTC GCC TCA TCA ACA TGT GAA TTC GTG GAA GTT ACA      815
Glu Ile Cys Asn Val Ala Ser Ser Thr Cys Glu Phe Val Glu Val Thr
                260                 265                 270

TCT CTA GAA GAC GAT GAA TGC TAT GAT TTG ATA GAA GCG TTT AGA ATG      863
Ser Leu Glu Asp Asp Glu Cys Tyr Asp Leu Ile Glu Ala Phe Arg Met
            280                 285                 290

CCT ATG CCA ACA GGG GAG AGA GAA GAA GAT ATT CTG AGG AAT ACG ATC      911
Pro Met Pro Thr Gly Glu Arg Glu Glu Asp Ile Leu Arg Asn Thr Ile
        295                 300                 305

AAG TTA ACC AGT GGA AGT CCA GCT GCT TTG ATG ATG GTT TTC AAA TCG      959
Lys Leu Thr Ser Gly Ser Pro Ala Ala Leu Met Met Val Phe Lys Ser
    310                 315                 320

TGT GAA CCC AAG ACC TTT                                              977
Cys Glu Pro Lys Thr Phe
325                 330
```

(2) INFORMATION FOR SEQ ID NO: 98:

(i) SEQUENCE CHARACTERISTICS:
        (A) LENGTH:753

(B) TYPE:amino acid (D) TOPOLOGY:linear (xi) SEQUENCE DESCRIPTION: SEQ ID NO: 98:

```
Met Asn Ile Ser Val Gln Thr Asn Asp Asp Gly Asp Tyr Val Ser Phe
                 5                  10                  15

Ser Asp Cys Arg Thr Gln Ser Lys Phe Pro Phe Gln Ser Glu Phe Pro
                20                  25                  30

Val Pro Glu Gln Phe Lys Thr Thr Phe Val Asn Gly Lys Leu Val Thr
            35                  40                  45

Val Val Ser Asp Ile Met Ser Trp Met Gln Asn Leu Lys Asn Tyr Gln
        50                  55                  60

His Leu Arg Asp Pro Ser Glu Tyr Met Ser Gln Val Tyr Gly Asp Pro
65                  70                  75                  80

Leu Ala Tyr Leu Gln Glu Thr Thr Lys Phe Val Thr Glu Arg Glu Tyr
                85                  90                  95

Tyr Glu Asp Phe Gly Tyr Gly Glu Cys Phe Asn Ser Thr Glu Ser Glu
```

```
                    100                 105                 110
        Val Gln Val Thr Pro Asn Val Tyr Tyr Arg Ala Val Trp Val Leu
                115                 120                 125

Phe Leu Gly Cys Met Ile Met Leu Tyr Leu Asn Ala Gln Ser Val Leu
        130                 135                 140

Asp Lys Tyr Asn Arg Asn Glu Lys Ile Val Asp Ile Gln Leu Lys Phe
        145                 150                 155                 160

Asp Thr Ala Pro Phe Pro Ala Ile Thr Leu Cys Asn Leu Asn Pro Tyr
                    165                 170                 175

Lys Ala Ser Leu Ala Thr Ser Val Asp Leu Val Lys Arg Thr Leu Ser
                180                 185                 190

Ala Phe Asp Gly Ala Met Gly Lys Ala Gly Asn Lys Asp His Glu
                195                 200                 205

Glu Glu Arg Glu Pro Gly Phe Ala Arg Cys Leu Cys Gly Ser Gln Gly
                210                 215                 220

Ser Ser Glu Gln Glu Asp Lys Asp Glu Glu Lys Glu Glu Leu Leu
        225                 230                 235                 240

Glu Thr Thr Thr Lys Lys Val Phe Asn Ile Asn Gly Glu Cys Cys Met
                    245                 250                 255

Asn Gly Met Glu Trp Lys Asn Met Thr Met Ser Ile Met Arg Ile Thr
                    260                 265                 270

Met Trp Lys Gln Leu Leu Glu Met Asn Met Met Glu Glu Cys Gln Ser
                275                 280                 285

Glu Arg Thr Asn Ser Thr Ser Pro Thr Gly Phe Asp Asp Arg Cys Ile
                290                 295                 300

Cys Ala Phe Asp Arg Ser Thr His Asp Ala Trp Pro Cys Phe Leu Asn
        305                 310                 315                 320

Gly Thr Trp Glu Thr Thr Glu Cys Asp Thr Cys Asn Glu His Ala Phe
                    325                 330                 335

Cys Thr Lys Asp Asn Lys Thr Ala Lys Gly His Arg Ser Pro Cys Ile
                    340                 345                 350

Cys Ala Pro Ser Arg Phe Cys Val Ala Tyr Asn Gly Lys Thr Pro Pro
                    355                 360                 365

Ile Glu Ile Trp Thr Tyr Leu Gln Gly Gly Thr Pro Thr Glu Asp Pro
                370                 375                 380

Asn Phe Leu Glu Ala Met Gly Phe Gln Gly Met Thr Asp Glu Val Ala
        385                 390                 395                 400

Ile Val Thr Lys Ala Lys Glu Asn Ile Met Phe Ala Met Ala Thr Leu
                    405                 410                 415

Ser Met Gln Asp Arg Glu Arg Leu Ser Thr Thr Lys Arg Glu Leu Val
                    420                 425                 430

His Lys Cys Ser Phe Asn Gly Lys Ala Cys Asp Ile Glu Ala Asp Phe
                435                 440                 445

Leu Thr His Ile Asp Pro Ala Phe Gly Ser Cys Phe Thr Phe Asn His
            450                 455                 460

Asn Arg Thr Val Asn Leu Thr Ser Ile Arg Ala Gly Pro Met Tyr Gly
        465                 470                 475                 480

Leu Arg Met Leu Val Tyr Val Asn Ala Ser Asp Tyr Met Pro Thr Thr
                    485                 490                 495

Glu Ala Thr Gly Val Arg Leu Thr Ile His Asp Lys Glu Asp Phe Pro
                    500                 505                 510

Phe Pro Asp Thr Phe Gly Tyr Ser Ala Pro Thr Gly Tyr Val Ser Ser
                515                 520                 525
```

-continued

```
Phe Gly Leu Arg Leu Arg Lys Met Ser Arg Leu Pro Ala Pro Tyr Gly
    530                 535                 540
Asp Cys Val Pro Asp Gly Lys Thr Ser Asp Tyr Ile Tyr Ser Asn Tyr
545                 550                 555                 560
Glu Tyr Ser Val Glu Gly Cys Tyr Arg Ser Cys Phe Gln Gln Leu Val
                565                 570                 575
Leu Lys Glu Cys Arg Cys Gly Asp Pro Arg Phe Pro Val Pro Glu Asn
            580                 585                 590
Ala His Arg Cys Asp Ala Ala Asp Pro Ile Ala Arg Lys Cys Leu Asp
        595                 600                 605
Ala Arg Met Asn Asp Leu Gly Gly Leu His Gly Ser Phe Arg Cys Arg
    610                 615                 620
Cys Gln Gln Pro Cys Arg Gln Ser Ile Tyr Ser Val Thr Tyr Ser Pro
625                 630                 635                 640
Ala Lys Trp Pro Ser Leu Ser Leu Gln Ile Gln Leu Gly Ser Cys Asn
                645                 650                 655
Gly Thr Ala Val Glu Cys Asn Lys His Tyr Lys Glu Asn Gly Ala Met
            660                 665                 670
Val Glu Val Phe Tyr Glu Gln Leu Asn Phe Glu Leu Met Thr Glu Ser
        675                 680                 685
Glu Ala Tyr Gly Phe Val Asn Leu Leu Ala Asp Phe Gly Gly Gln Leu
    690                 695                 700
Gly Leu Trp Cys Gly Ile Ser Phe Leu Thr Cys Cys Glu Phe Val Phe
705                 710                 715                 720
Leu Phe Leu Glu Thr Ala Tyr Met Ser Ala Glu His Asn Tyr Ser Leu
                725                 730                 735
Tyr Lys Lys Lys Ala Glu Lys Ala Lys Lys Ile Ala Ser Gly Ser
            740                 745                 750
Phe
```

(2) INFORMATION FOR SEQ ID NO: 99:

(i) SEQUENCE CHARACTERISTICS:
        (A) LENGTH:755

(B) TYPE:amino acid (D) TOPOLOGY:linear (xi) SEQUENCE DESCRIPTION: SEQ ID NO: 99:

```
Met Asn Ile Ser Leu Gln Thr Thr Asp Gly Glu Tyr Val Arg Phe
                5                  10                  15
Ser Asp Phe Arg Tyr Gln Thr Ile Leu Asn Phe Gln Ser Glu Phe Pro
                 20                  25                  30
Val Pro Glu Gln Phe Lys Thr Thr Phe Val Asn Gly Lys Leu Val Thr
             35                  40                  45
Val Val Ser Asp Ile Met Ser Trp Met Gln Asn Leu Lys Asn Tyr Gln
         50                  55                  60
His Leu Arg Asp Pro Ser Glu Tyr Met Ser Gln Val Tyr Gly Asp Pro
65                  70                  75                  80
Leu Ala Tyr Leu Gln Glu Asn Thr Lys Phe Val Thr Glu Arg Glu Tyr
                 85                  90                  95
Tyr Glu Asp Phe Gly Tyr Gly Cys Phe Asn Ser Ser Glu Ser Glu
                100                 105                 110
```

-continued

```
Val Gln Val Thr Pro Asn Val Tyr Tyr Arg Ala Val Trp Val Met Leu
    115                 120                 125
Phe Leu Gly Cys Met Ile Met Leu Tyr Leu Asn Ala Gln Ser Val Leu
130                 135                 140
Asp Lys Tyr Asn Arg Asn Glu Lys Ile Val Asp Ile Gln Leu Lys Phe
145                 150                 155                 160
Asp Thr Ala Pro Phe Pro Ala Ile Thr Leu Cys Asn Leu Asn Pro Tyr
                165                 170                 175
Lys Ala Ser Leu Ala Thr Ser Val Asp Leu Val Lys Arg Thr Leu Ser
                180                 185                 190
Ala Phe Asp Gly Ala Met Gly Lys Ala Gly Gly Asn Lys Glu His Asp
        195                 200                 205
Gly Glu Lys Glu Pro Gly Phe Ala Arg Cys Leu Cys Gly Ser Gln Gly
        210                 215                 220
Ser Ser Glu Gln Glu Asp Lys Asp Glu Lys Glu Glu Met His
225                 230                 235                 240
Glu Thr Thr Thr Arg Lys Pro Phe Asn Ile Asn Gly Lys Cys Cys Met
                245                 250                 255
Asn Gly Met Glu Trp Lys Ser Met Thr Thr Met Ser Ile Met Arg Ile
                260                 265                 270
Thr Met Ser Lys Arg Arg Leu Glu Met Asn Met Met Glu Glu Cys Gln
        275                 280                 285
Ser Glu Arg Thr Asn Ser Thr Ser Pro Thr Gly Phe Asp Asp Arg Cys
        290                 295                 300
Ile Cys Ala Phe Asp Arg Ser Thr His Asp Asp Ala Trp Pro Cys Phe
305                 310                 315                 320
Leu Asn Gly Thr Trp Glu Thr Thr Glu Cys Asp Thr Cys Asn Glu His
                325                 330                 335
Ala Phe Cys Thr Lys Asp Asn Lys Thr Ala Lys Ser His Arg Ser Pro
                340                 345                 350
Cys Ile Cys Ala Pro Ser Lys Phe Cys Val Ala Tyr Asn Gly Lys Thr
        355                 360                 365
Pro Pro Ile Glu Ile Trp Thr Tyr Leu Gln Gly Gly Thr Pro Thr Glu
        370                 375                 380
Asp Pro Asn Phe Leu Glu Ala Met Gly Phe Gln Gly Met Thr Asp Glu
385                 390                 395                 400
Val Ala Ile Val Thr Lys Ala Lys Glu Asn Ile Met Phe Ala Met Ala
                405                 410                 415
Thr Leu Ser Met Gln Asp Arg Glu Arg Leu Ser Thr Thr Lys Arg Glu
                420                 425                 430
Leu Met His Lys Cys Ser Phe Asn Gly Lys Ala Cys Asp Ile Asp Ala
        435                 440                 445
Glu Phe Leu Thr His Ile Asp Pro Val Phe Gly Ser Cys Phe Thr Phe
        450                 455                 460
Asn His Asn Arg Thr Ala Ile Leu Thr Ser Ile Arg Ala Gly Pro Met
465                 470                 475                 480
Tyr Gly Leu Arg Met Leu Val Tyr Val Asn Ala Ser Asp Tyr Met Pro
                485                 490                 495
Thr Thr Glu Ala Thr Gly Val Arg Leu Thr Ile His Asp Lys Glu Asp
                500                 505                 510
Phe Pro Phe Pro Asp Thr Phe Gly Tyr Ser Ala Pro Thr Gly Tyr Val
        515                 520                 525
Ser Ser Phe Gly Leu Arg Leu Arg Lys Met Ser Arg Leu Pro Ala Pro
```

```
                530                 535                 540
Tyr Gly Asp Cys Val Pro Asp Gly Lys Thr Ser Asp Tyr Met Tyr Ser
545                 550                 555                 560

Asn Tyr Glu Tyr Ser Val Glu Gly Cys Tyr Arg Ser Cys Phe Gln Gln
                565                 570                 575

Leu Val Leu Lys Glu Cys Arg Cys Gly Asp Pro Gly Phe Pro Val Pro
                580                 585                 590

Glu Gly Ala Arg His Cys Ala Pro Ala Asp Pro Val Ala Arg Arg Ser
                595                 600                 605

Leu Asp Ala Arg Met Asn Asp Leu Gly Gly Leu His Gly Ser Phe Arg
                610                 615                 620

Tyr Arg Cys Gln Gln Pro Cys Ser Gln Ser Ile Tyr Ser Val Thr Tyr
625                 630                 635                 640

Ser Pro Ala Lys Trp Pro Ser Leu Ser Leu Gln Ile Gln Leu Gly Ser
                645                 650                 655

Cys Asn Gly Thr Ala Val Glu Cys Asn Lys His Tyr Lys Glu Asn Gly
                660                 665                 670

Ala Met Val Glu Val Phe Tyr Glu Gln Leu Asn Phe Glu Met Leu Thr
                675                 680                 685

Glu Ser Glu Ala Tyr Gly Phe Val Asn Leu Leu Ala Asp Phe Gly Gly
                690                 695                 700

Gln Leu Gly Leu Trp Cys Gly Ile Ser Phe Leu Thr Cys Cys Glu Phe
705                 710                 715                 720

Val Phe Leu Phe Leu Glu Thr Ala Tyr Met Ser Ala Glu His Asn Tyr
                725                 730                 735

Ser Leu Tyr Lys Lys Lys Ala Glu Lys Ala Lys Lys Val Ala Ser
                740                 745                 750

Gly Ser Phe
        755

(2) INFORMATION FOR SEQ ID NO: 100:

(i) SEQUENCE CHARACTERISTICS:
        (A) LENGTH:520

(B) TYPE:amino acid (D) TOPOLOGY:linear (xi) SEQUENCE DESCRIPTION: SEQ ID NO: 100:

Met Gln Leu Lys Phe Glu Pro Ala Pro Phe Ala Ala Thr Val Cys
                5                   10                  15

Asn Leu Asn Ala Phe Lys Ala Ser Gln Cys Val Cys Asn Leu Pro Asp
                20                  25                  30

Asp Gln Cys Val Pro Gln Arg Asn Pro Leu Thr Lys Asn Thr Ser Val
                35                  40                  45

Cys Met Cys Phe Glu Asp Ala Thr Thr Gly Asp Ile Trp Pro Cys Tyr
        50                  55                  60

Pro Thr Thr Val Trp Asn Glu Lys Thr Cys Tyr His Cys Ser Lys Ser
65                  70                  75                  80

Asn Thr Cys Asp Asp Pro Asp Arg Pro Pro Asn Ile Thr Ser Leu Leu
                85                  90                  95

Thr Glu Pro Lys Ala Thr Pro Cys Leu Cys Gln Ser Val Ser His Tyr
                100                 105                 110

Cys Val Met Lys Pro Thr Glu Asp Val Lys Cys Asp Arg Ser Thr Asn
```

-continued

```
            115                 120                 125
Thr Ser Pro Glu Ile Glu Ser Ala Phe Gly Leu Ala Asp Leu Arg Asp
        130                 135                 140

Arg Gly Ala Ile Thr Thr Lys Thr Lys Glu Asn Leu Ile Phe Leu Val
145                 150                 155                 160

Ala Ala Met Pro Met Glu Thr Arg Arg Gln Leu Ser Tyr Thr Leu Asp
                165                 170                 175

Glu Phe Val Leu Arg Cys Ser Phe Asn Ser Glu Asp Cys Asp Leu Arg
                180                 185                 190

Arg Asp Phe His Ile His Met Asp Pro Glu Phe Gly Asn Cys Tyr Thr
                195                 200                 205

Phe Asn Phe Asn Asp Ser Val Glu Leu Lys Asn Ser Arg Ala Gly Pro
        210                 215                 220

Met Tyr Gly Leu Arg Leu Leu Leu Asn Val Asn Gln Ser Asp Tyr Met
225                 230                 235                 240

Pro Thr Thr Glu Ala Ala Gly Val Arg Leu Val Val His Glu Gln Asp
                245                 250                 255

Gln Glu Pro Phe Pro Asp Thr Phe Gly Tyr Ser Ala Pro Thr Gly Phe
                260                 265                 270

Val Ser Ser Phe Gly Leu Lys Thr Lys Val Leu His Arg Leu Asn Glu
        275                 280                 285

Pro Tyr Gly Met Cys Ser Asp Thr Phe Gly Pro Glu Gly Tyr Ile Tyr
        290                 295                 300

Ala Glu His Tyr Ser Pro Glu Gly Cys Tyr Arg Asn Cys Phe Gln His
305                 310                 315                 320

Met Ile Leu Asp Thr Cys Gly Cys Gly Asp Pro Arg Phe Pro Leu Pro
                325                 330                 335

Ser Asp Lys Glu Lys Pro Cys Asp Ala Arg Asn Ala Arg Glu Arg Thr
                340                 345                 350

Cys Leu Thr Asn Leu Thr Thr Ile Leu Gly Gly Phe His His Leu Gln
        355                 360                 365

His Asp Cys His Cys Val Gln Pro Cys Thr Glu Asn Val Phe Glu Thr
        370                 375                 380

Ala Tyr Ser Ala Ala Trp Pro Ala Ile Asn Phe Asn Ile Gly Ala
385                 390                 395                 400

Asp Cys Pro Ala Val Tyr His Ile Ser Asn Asp Ser Lys Ala Cys Ala
                405                 410                 415

Glu Tyr Tyr Arg Leu Asn Thr Ala Tyr Ile Glu Ile Tyr Tyr Glu Gln
                420                 425                 430

Leu Asn Phe Glu Thr Leu Lys Glu Thr Ala Gly Tyr Thr Leu Val Asn
        435                 440                 445

Leu Phe Ser Asp Phe Gly Gly Asn Ile Gly Leu Trp Ile Gly Phe Ser
        450                 455                 460

Val Ile Thr Met Phe Glu Val Val Glu Val Leu Cys Glu Ile Ile Ile
465                 470                 475                 480

Tyr Ile Gly Thr His Ser Leu Phe Lys Leu Phe Ile Ser Lys Leu Leu
                485                 490                 495

Pro Ser Gln Glu Asn Asn His Thr Ala Phe Ile Asn Glu Ser Ala Glu
                500                 505                 510

Arg Ile Ala Lys Thr Arg Met Lys
                515                 520
```

(2) INFORMATION FOR SEQ ID NO: 101:

(i) SEQUENCE CHARACTERISTICS:
    (A) LENGTH:77

(B) TYPE:amino acid (D) TOPOLOGY:linear (xi) SEQUENCE DESCRIPTION: SEQ ID NO: 101:

Asp Phe Gly Gly Gln Leu Gly Leu Trp Cys Gly Ile Ser Phe Ile Thr
 1               5                  10                  15

Xaa Cys Glu Phe Val Phe Leu Xaa Leu Glu Xaa Ile Xaa Xaa Tyr Met
                20                  25                  30

Ser Ala Glu His Asn Tyr Xaa Leu Tyr Xaa Xaa Xaa Xaa Xaa Lys Lys
            35                  40                  45

Lys Xaa Xaa Xaa Xaa Xaa Xaa Xaa Ala Glu Xaa Ala Xaa Lys Ile Ala
        50                  55                  60

Ser Gly Ser Phe Xaa Xaa Xaa Xaa Xaa Xaa Xaa Xaa
 65              70                  75

(2) INFORMATION FOR SEQ ID NO: 102:

(i) SEQUENCE CHARACTERISTICS:
        (A) LENGTH:26

(B) TYPE:amino acid (D) TOPOLOGY:linear (xi) SEQUENCE DESCRIPTION: SEQ ID NO: 102:

Asp Ile Gln Leu Lys Phe Asp Thr Ala Pro Phe Pro Ala Ile Thr Leu
 1               5                  10                  15

Cys Asn Leu Asn Pro Tyr Lys Ala Ser Leu
                20                  25

(2) INFORMATION FOR SEQ ID NO: 103:

(i) SEQUENCE CHARACTERISTICS:
        (A) LENGTH:10

(B) TYPE:amino acid (D) TOPOLOGY:linear (xi) SEQUENCE DESCRIPTION: SEQ ID NO: 103:

Arg Ala Gly Pro Met Tyr Gly Leu Arg Met
 1               5                  10

(2) INFORMATION FOR SEQ ID NO: 104:

(i) SEQUENCE CHARACTERISTICS:
        (A) LENGTH:19

(B) TYPE:amino acid (D) TOPOLOGY:linear (xi) SEQUENCE DESCRIPTION: SEQ ID NO: 104:

Pro Phe Pro Asp Thr Phe Gly Tyr Ser Ala Pro Thr Gly Phe Val Ser Ser
 1               5                  10                  15

Phe Gly (2) INFORMATION FOR SEQ ID NO: 105:

(i) SEQUENCE CHARACTERISTICS:
        (A) LENGTH:6

(B) TYPE:amino acid (D) TOPOLOGY:linear (xi) SEQUENCE DESCRIPTION: SEQ ID NO: 105:

Gly Asp Pro Arg Phe Pro
 1            5

(2) INFORMATION FOR SEQ ID NO: 106:

(i) SEQUENCE CHARACTERISTICS:
        (A) LENGTH:11

(B) TYPE:amino acid (D) TOPOLOGY:linear (xi) SEQUENCE DESCRIPTION: SEQ ID NO: 106:

Ile Glu Val Phe Tyr Glu Gln Leu Asn Phe Glu
 1           5                  10

(2) INFORMATION FOR SEQ ID NO: 107:

(i) SEQUENCE CHARACTERISTICS:
        (A) LENGTH:7

(B) TYPE:amino acid (D) TOPOLOGY:linear (xi) SEQUENCE DESCRIPTION: SEQ ID NO: 107:

Cys Ile Cys Ala Phe Asp Arg
 1            5

(2) INFORMATION FOR SEQ ID NO: 108:

(i) SEQUENCE CHARACTERISTICS:
        (A) LENGTH:6

(B) TYPE:amino acid (D) TOPOLOGY:linear (xi) SEQUENCE DESCRIPTION: SEQ ID NO: 108:

Phe Cys Val Ala Tyr Asn
 1            5

(2) INFORMATION FOR SEQ ID NO: 109:

(i) SEQUENCE CHARACTERISTICS:
        (A) LENGTH:17

(B) TYPE:amino acid (D) TOPOLOGY:linear (xi) SEQUENCE DESCRIPTION: SEQ ID NO: 109:

Asp Glu Val Ala Ile Val Thr Lys Ala Lys Glu Asn Ile Met Phe Ala
 1           5                10              15

```
Met (2) INFORMATION FOR SEQ ID NO: 110:

(i) SEQUENCE CHARACTERISTICS:
        (A) LENGTH:11

(B) TYPE:amino acid (D) TOPOLOGY:linear (xi) SEQUENCE DESCRIPTION: SEQ ID NO: 110:

Cys Ser Phe Asn Gly Lys Ala Cys Asp Ile Asp
 1               5                   10

(2) INFORMATION FOR SEQ ID NO: 111:

(i) SEQUENCE CHARACTERISTICS:
        (A) LENGTH:9

(B) TYPE:amino acid (D) TOPOLOGY:linear (xi) SEQUENCE DESCRIPTION: SEQ ID NO: 111:

Cys Phe Thr Phe Asn His Asn Arg Thr
 1               5

(2) INFORMATION FOR SEQ ID NO: 112:

(i) SEQUENCE CHARACTERISTICS:
        (A) LENGTH:16

(B) TYPE:amino acid (D) TOPOLOGY:linear (xi) SEQUENCE DESCRIPTION: SEQ ID NO: 112:

Ser Ile Arg Ala Gly Pro Met Tyr Gly Leu Arg Met Leu Val Val Asn
 1               5                   10                  15

(2) INFORMATION FOR SEQ ID NO: 113:

(i) SEQUENCE CHARACTERISTICS:
        (A) LENGTH:9

(B) TYPE:amino acid (D) TOPOLOGY:linear (xi) SEQUENCE DESCRIPTION: SEQ ID NO: 113:

Ser Asp Tyr Met Pro Thr Thr Glu Ala
 1               5

(2) INFORMATION FOR SEQ ID NO: 114:

(i) SEQUENCE CHARACTERISTICS:
        (A) LENGTH:29

(B) TYPE:amino acid (D) TOPOLOGY:linear (xi) SEQUENCE DESCRIPTION: SEQ ID NO: 114:
```

```
Thr Ile His Asp Lys Glu Asp Pro Phe Pro Asp Thr Phe Gly Tyr Ser
 1               5                  10                  15

Ala Pro Thr Gly Phe Val Ser Ser Phe Gly Leu Arg Leu
            20                  25
```

(2) INFORMATION FOR SEQ ID NO: 115:

(i) SEQUENCE CHARACTERISTICS:
        (A) LENGTH:8

(B) TYPE:amino acid (D) TOPOLOGY:linear (xi) SEQUENCE DESCRIPTION: SEQ ID NO: 115:

```
Tyr Gly Asp Cys Val Pro Asp Gly
 1               5
```

(2) INFORMATION FOR SEQ ID NO: 116:

(i) SEQUENCE CHARACTERISTICS:
        (A) LENGTH:9

(B) TYPE:amino acid (D) TOPOLOGY:linear (xi) SEQUENCE DESCRIPTION: SEQ ID NO: 116:

```
Glu Gly Cys Tyr Arg Ser Cys Phe Gln
 1               5
```

(2) INFORMATION FOR SEQ ID NO: 117:

(i) SEQUENCE CHARACTERISTICS:
        (A) LENGTH:8

(B) TYPE:amino acid (D) TOPOLOGY:linear (xi) SEQUENCE DESCRIPTION: SEQ ID NO: 117:

```
Arg Cys Arg Cys Gln Gln Pro Cys
 1               5
```

(2) INFORMATION FOR SEQ ID NO: 118:

(i) SEQUENCE CHARACTERISTICS:
        (A) LENGTH:40

(B) TYPE:amino acid (D) TOPOLOGY:linear (xi) SEQUENCE DESCRIPTION: SEQ ID NO: 118:

```
Glu Asn Gly Ala Met Ile Glu Val Phe Tyr Glu Gln Leu Asn Phe Glu
 1               5                  10                  15

Met Leu Thr Glu Ser Glu Ala Tyr Gly Ile Val Asn Leu Leu Ala Asp
            20                  25                  30

Phe Gly Gly Gln Leu Gly Leu Trp
            35                  40
```

(2) INFORMATION FOR SEQ ID NO: 119:

(i) SEQUENCE CHARACTERISTICS:
            (A) LENGTH:18

(B) TYPE:amino acid (D) TOPOLOGY:linear (xi) SEQUENCE DESCRIPTION: SEQ ID NO: 119:

Phe Gly Tyr Ser Ala Pro Thr Gly Phe Ile Ser Ser Phe Gly Leu Lys
 1               5                  10                  15
Thr Lys (2) INFORMATION FOR SEQ ID NO: 120:

(i) SEQUENCE CHARACTERISTICS:
            (A) LENGTH:7

(B) TYPE:amino acid (D) TOPOLOGY:linear (xi) SEQUENCE DESCRIPTION: SEQ ID NO: 120:

Cys Ser Asp Thr Phe Arg Pro
 1               5

(2) INFORMATION FOR SEQ ID NO: 121:

(i) SEQUENCE CHARACTERISTICS:
            (A) LENGTH:8

(B) TYPE:amino acid (D) TOPOLOGY:linear (xi) SEQUENCE DESCRIPTION: SEQ ID NO: 121:

Glu His Tyr Ser Pro Glu Gly Cys
 1               5

(2) INFORMATION FOR SEQ ID NO: 123:

(i) SEQUENCE CHARACTERISTICS:
            (A) LENGTH:7

(B) TYPE:amino acid (D) TOPOLOGY:linear (xi) SEQUENCE DESCRIPTION: SEQ ID NO: 123:

Glu Ile Glu Cys Arg Ala Leu
 1               5

(2) INFORMATION FOR SEQ ID NO: 124:

(i) SEQUENCE CHARACTERISTICS:
            (A) LENGTH:11

(B) TYPE:amino acid (D) TOPOLOGY:linear (xi) SEQUENCE DESCRIPTION: SEQ ID NO: 124:

Asp Phe Glu Pro Arg Asp Ala Leu Thr Tyr Leu
 1               5                  10

(2) INFORMATION FOR SEQ ID NO: 125:

(i) SEQUENCE CHARACTERISTICS:
        (A) LENGTH:9

(B) TYPE:amino acid (D) TOPOLOGY:linear (xi) SEQUENCE DESCRIPTION: SEQ ID NO: 125:

Ser Phe Phe Leu Phe Leu His Gly Arg
 1               5

(2) INFORMATION FOR SEQ ID NO: 126:

(i) SEQUENCE CHARACTERISTICS:
        (A) LENGTH:8

(B) TYPE:amino acid (D) TOPOLOGY:linear (xi) SEQUENCE DESCRIPTION: SEQ ID NO: 126:

Gly Ser Gly Lys Ser Val Ile Ala
 1               5

(2) INFORMATION FOR SEQ ID NO: 127:

(i) SEQUENCE CHARACTERISTICS:
        (A) LENGTH:8

(B) TYPE:amino acid (D) TOPOLOGY:linear (xi) SEQUENCE DESCRIPTION: SEQ ID NO: 127:

Val Trp Leu Lys Asp Ser Gly Thr
 1               5

(2) INFORMATION FOR SEQ ID NO: 128:

(i) SEQUENCE CHARACTERISTICS:
        (A) LENGTH:7

(B) TYPE:amino acid (D) TOPOLOGY:linear (xi) SEQUENCE DESCRIPTION: SEQ ID NO: 128:

Thr Phe Asp Leu Phe Thr Asp
 1               5

(2) INFORMATION FOR SEQ ID NO: 129:

(i) SEQUENCE CHARACTERISTICS:
        (A) LENGTH:7

(B) TYPE:amino acid (D) TOPOLOGY:linear (xi) SEQUENCE DESCRIPTION: SEQ ID NO: 129:

Leu Leu Met Leu Lys Ser Glu 1           5

(2) INFORMATION FOR SEQ ID NO: 130:

(i) SEQUENCE CHARACTERISTICS:
        (A) LENGTH:8

(B) TYPE:amino acid (D) TOPOLOGY:linear (xi) SEQUENCE DESCRIPTION: SEQ ID NO: 130:

Thr Ser Val Val Leu Lys Arg Met
1               5

(2) INFORMATION FOR SEQ ID NO: 131:

(i) SEQUENCE CHARACTERISTICS:
        (A) LENGTH:7

(B) TYPE:amino acid (D) TOPOLOGY:linear (xi) SEQUENCE DESCRIPTION: SEQ ID NO: 131:

Arg Pro Asn Thr Leu Phe Val
1               5

(2) INFORMATION FOR SEQ ID NO: 132:

(i) SEQUENCE CHARACTERISTICS:
        (A) LENGTH:30

(B) TYPE:amino acid (D) TOPOLOGY:linear (xi) SEQUENCE DESCRIPTION: SEQ ID NO: 132:

Asp Asp Val Val Gln Glu Glu Thr Ile Arg Trp Ala Gln Glu Leu Arg
1               5                   10                  15

Leu Arg Cys Leu Val Thr Thr Arg Asp Val Glu Ile Ser Asn
            20                  25                  30

(2) INFORMATION FOR SEQ ID NO: 133:

(i) SEQUENCE CHARACTERISTICS:
        (A) LENGTH:30

(B) TYPE:amino acid (D) TOPOLOGY:linear (xi) SEQUENCE DESCRIPTION: SEQ ID NO: 133:

Asp Asp Val Val Gln Asp Glu Thr Ile Arg Trp Ala Gln Glu Leu Arg
1               5                   10                  15

Leu Arg Cys Leu Ile Thr Thr Arg Asp Val Glu Ile Cys Asn
            20                  25                  30

(2) INFORMATION FOR SEQ ID NO: 134:

(i) SEQUENCE CHARACTERISTICS:
        (A) LENGTH:16

(B) TYPE:amino acid (D) TOPOLOGY:linear (xi) SEQUENCE DESCRIPTION: SEQ ID NO: 134:

Phe Lys Ser Cys Glu Pro Lys Thr Phe Glu Lys Met Ala Gln Leu Asn
 1               5                  10                  15

(2) INFORMATION FOR SEQ ID NO: 135:

(i) SEQUENCE CHARACTERISTICS:
        (A) LENGTH:16

(B) TYPE:amino acid (D) TOPOLOGY:linear (xi) SEQUENCE DESCRIPTION: SEQ ID NO: 135:

Phe Lys Ser Cys Glu Pro Lys Thr Phe Asp Lys Met Ala Gln Leu Asn
 1               5                  10                  15

(2) INFORMATION FOR SEQ ID NO: 136:

(i) SEQUENCE CHARACTERISTICS:
        (A) LENGTH:13

(B) TYPE:amino acid (D) TOPOLOGY:linear (xi) SEQUENCE DESCRIPTION: SEQ ID NO: 136:

Leu Gln Arg Cys Val Glu Val Leu Ser Asp Glu Asp Arg
 1               5                  10

(2) INFORMATION FOR SEQ ID NO: 137:

(i) SEQUENCE CHARACTERISTICS:
        (A) LENGTH:20

(B) TYPE:amino acid (D) TOPOLOGY:linear (xi) SEQUENCE DESCRIPTION: SEQ ID NO: 137:

Glu Val Ala Asp Arg Leu Lys Arg Leu Ser Lys Arg Gly Ala Leu Leu
 1               5                  10                  15
Ser Gly Lys Arg
                20

(2) INFORMATION FOR SEQ ID NO: 138:

(i) SEQUENCE CHARACTERISTICS:
        (A) LENGTH:20

(B) TYPE:amino acid (D) TOPOLOGY:linear (xi) SEQUENCE DESCRIPTION: SEQ ID NO: 138:

Glu Val Ala Asp Arg Leu Lys Arg Leu Thr Lys Arg Gly Ala Leu Leu
 1               5                  10                  15
Ser Gly Lys Arg
                20

(2) INFORMATION FOR SEQ ID NO: 139:

(i) SEQUENCE CHARACTERISTICS:
        (A) LENGTH:7

(B) TYPE:amino acid (D) TOPOLOGY:linear (xi) SEQUENCE DESCRIPTION: SEQ ID NO: 139:

```
Phe Leu Lys His Val Val Asp
 1               5
```

(2) INFORMATION FOR SEQ ID NO: 140:

(i) SEQUENCE CHARACTERISTICS:
        (A) LENGTH:33

(B) TYPE:nuceic acid (C) STRANDEDNESS:single (D) TOPOLOGY:linear (xi) SEQUENCE DESCRIPTION: SEQ ID NO: 140:

```
CCN TTY CCN GAY ACN TTY GGN TAY WSN GCN CCN                33
Pro Phe Pro Asp Thr Phe Gly Tyr Ser Ala Pro
 1               5                       10
```

(2) INFORMATION FOR SEQ ID NO: 141:

(i) SEQUENCE CHARACTERISTICS:
        (A) LENGTH:10

(B) TYPE:amino acid (D) TOPOLOGY:linear (xi) SEQUENCE DESCRIPTION: SEQ ID NO: 141:

```
Cys Gly Asp Pro Arg Phe Pro Val Pro Glu
 1               5                   10
```

(2) INFORMATION FOR SEQ ID NO: 142:

(i) SEQUENCE CHARACTERISTICS:
        (A) LENGTH:69

(B) TYPE:amino acid (D) TOPOLOGY:linear (xi) SEQUENCE DESCRIPTION: SEQ ID NO: 142:

```
Glu Gln Xaa Leu Xaa Glu Xaa Xaa Asn Asn Xaa Xaa Xaa Pro Glu
 1               5                   10                  15

Xaa Xaa Xaa Pro Xaa Xaa Xaa Xaa Lys Phe Arg Arg Xaa Ser Ala Xaa
                20                  25                  30

Xaa Met Tyr Pro Xaa Xaa Xaa Glu Glu Xaa Val Ile Arg Pro Glu Asp
            35                  40                  45

Tyr Xaa Lys Phe Met Xaa Xaa His Xaa Xaa Phe Tyr Asp Ser Leu Lys
        50                  55                  60

Xaa Phe Xaa Xaa Xaa
65
```

(2) INFORMATION FOR SEQ ID NO: 143:

(i) SEQUENCE CHARACTERISTICS:
        (A) LENGTH:12

(B) TYPE:amino acid (D) TOPOLOGY:linear (xi) SEQUENCE DESCRIPTION: SEQ ID NO: 143:

```
Gly Gly Asn Thr Gly Gly Ala Thr Gly Gly Ala Thr
  1               5                  10
```